(12) United States Patent
Lau

(10) Patent No.: US 10,186,169 B2
(45) Date of Patent: Jan. 22, 2019

(54) SYSTEM AND METHODS FOR ASSESSING A PERSON'S ORAL FEEDING SKILLS DURING ORAL FEEDING

(71) Applicant: Chantal Lau, Santa Fe, NM (US)

(72) Inventor: Chantal Lau, Santa Fe, NM (US)

( * ) Notice: Subject to any disclaimer, the term of this patent is extended or adjusted under 35 U.S.C. 154(b) by 0 days.

(21) Appl. No.: 15/412,027

(22) Filed: Jan. 22, 2017

(65) Prior Publication Data

US 2018/0211558 A1    Jul. 26, 2018

(51) Int. Cl.
| | |
|---|---|
| *G09B 19/00* | (2006.01) |
| *A61J 9/00* | (2006.01) |
| *A61J 9/04* | (2006.01) |
| *A61J 11/00* | (2006.01) |
| *A61B 5/00* | (2006.01) |

(52) U.S. Cl.
CPC ............ *G09B 19/0092* (2013.01); *A61B 5/68* (2013.01); *A61J 9/00* (2013.01); *A61J 9/04* (2013.01); *A61J 11/00* (2013.01); *G09B 19/003* (2013.01); *A61J 2200/30* (2013.01); *A61J 2200/70* (2013.01)

(58) Field of Classification Search
CPC ...... A61J 9/00; A61J 2200/76; A61J 15/0084; A61J 9/04; A61J 11/00; A61J 2200/30; A61J 2200/70; A61B 5/038; A61B 5/682; A61B 2562/0247; A61B 5/68; G09B 23/281; G09B 19/0092; G09B 19/003
USPC ........................................................ 434/247
See application file for complete search history.

(56) References Cited

U.S. PATENT DOCUMENTS

| | | | |
|---|---|---|---|
| 3,790,016 | A | 2/1974 | Kron |
| 3,895,533 | A | 7/1975 | Steier |
| 4,232,687 | A | 11/1980 | Anderson-Shanklin |
| 6,033,367 | A | 3/2000 | Goldfield |
| 6,109,100 | A | 8/2000 | Buckley et al. |
| 6,693,285 | B1 | 2/2004 | Weiss |
| 6,966,904 | B2 | 11/2005 | Ruth et al. |
| 6,991,122 | B2 | 1/2006 | Holley |
| 7,887,507 | B2 | 2/2011 | Shemesh et al. |

(Continued)

FOREIGN PATENT DOCUMENTS

NL    2013050418    12/2013

OTHER PUBLICATIONS

C. Laua, S. Fucile and E.G. Gisel, "Impact of nonnutritive oral motor stimulation and infant massage therapy on oral feeding skills of pre term infants", Oct. 22, 2012, Journal of Neonatal-Perinatal Medicine 5 (2012), pp. 311-317.*

(Continued)

*Primary Examiner* — Jack Yip
(74) *Attorney, Agent, or Firm* — Robert D. Watson

(57) ABSTRACT

The present invention relates to systems and methods for assessing and improving an infant's oral feeding skills. The system comprises a "smart" baby feeding device comprising an instrumented baby bottle with a removable, battery-powered monitoring module wirelessly connected to a remote device (e.g., smart phone, tablet, laptop, PC). The purpose of the remote device is to monitor (in real time) and measure the frequency and quality of feedings of new-born babies to help optimize feeding development by providing real-time feeding performance information back to the caregiver. The information collected is of assistance in minimizing feeding difficulties and correcting feeding deficiencies.

26 Claims, 42 Drawing Sheets

(56) References Cited

U.S. PATENT DOCUMENTS

| | | | |
|---|---|---|---|
| 7,896,835 | B2 | 3/2011 | Dahan et al. |
| 8,144,030 | B1 | 3/2012 | Lipke |
| 8,413,502 | B2 | 4/2013 | Zemel et al. |
| 8,473,219 | B2 | 6/2013 | Kaplan et al. |
| 8,482,416 | B2 | 7/2013 | Krans et al. |
| 8,568,352 | B2 | 10/2013 | Thalab |
| 8,663,131 | B2 | 3/2014 | Cunningham et al. |
| 8,979,896 | B2 | 3/2015 | Barlow et al. |
| 2005/0283327 | A1 | 1/2005 | Bowman et al. |
| 2008/0039778 | A1 | 2/2008 | Goldie et al. |
| 2010/0145166 | A1 | 1/2010 | Pickler et al. |
| 2010/0131454 | A1 | 5/2010 | Kaplan et al. |
| 2011/0153365 | A1 | 6/2011 | Meier et al. |
| 2011/0251510 | A1 | 10/2011 | Zemel |
| 2012/0302924 | A1 | 11/2012 | Cunningham et al. |
| 2013/0073211 | A1 | 3/2013 | Hershkovich |
| 2013/0096461 | A1 | 4/2013 | Sella |
| 2013/0319915 | A1* | 12/2013 | Gellibolian ............ C02F 1/002 210/87 |
| 2014/0207024 | A1 | 7/2014 | Aron et al. |
| 2014/0242213 | A1* | 8/2014 | McCarty ............... A61J 9/00 426/2 |
| 2015/0196247 | A1* | 7/2015 | Lau ....................... A61J 11/00 600/301 |

OTHER PUBLICATIONS

Picker RH, Reyna BA, Effects of non-nutritive sucking on nutritive sucking, breathing and behavior during bottle feedings of preterm infants, Advances in Neonatal Care, vol. 4, No. 4 (Aug. 2004), pp. 226-234.
Lau C, Henning SJ, A noninvasive method for determining patterns of milk intake in the breast-fed infant, Jn. of Pediatric Gastroenterology and Nutrition 9:481-487 (1989).
Lau C, Hurst N, Oral Feeding in Infants, Curr Probl Pediatr, Apr. 1999, pp. 105-124.
Lau C, Kusnierczyk I, Quantitative evaluation of infant's nonnutritive and nutritive sucking, Dysphagia 16:58-67 (2001).
Sameroff AJ, The Components of Sucking in the Human Newborn, Jnl. of Experimental Child Psychology 6, (1998) pp. 607-623.
Tamura Y, Horikawa Y, Yoshida S, Co-ordination of tongue movements and peri-oral muscle activities during nutritive sucking, Developmental Medicine and Child Neurology, 1996 38, pp. 503-510.
Da Costa SP, Van der Schans CP, The reliability of the neonatal oral-motor assessment sale, Acta Paediatrica, Oct. 2007, (2008) 97, pp. 21-26.
Da Costa SP, Van der Schans CP, The reliability of the neonatal oral-motor assessment sale, Acta Paediatrica, Oct. 2007, (2008) 97, pp. 21-26, Supplementary Tables.
American Academy of Pediatrics. Hospital discharge of the high-risk neonate. Pediatrics 2008; 122:1119-1126.
Lau C, Hurst N. Oral feeding in infants. Curr Probl Pediatr 1999; 29:105-24.
Burklow KA, McGrath AM, Kaul A. Management and prevention of feeding problems in young children with prematurity and very low birth weight. Inf Young Children 2002; 14:19-30.
Palmer MM, Crawley K, Blanco IA. Neonatal Oral-Motor Assessment scale: a reliability study. J Perinatol 1993; 13:28-35.
Thoyre SM, Shaker CS, Pridham KF. The early feeding skills assessment for preterm infants. Neonatal Netw 2005; 24:7-16.
Da Costa SP, van der Schans CP. The reliability of the Neonatal Oral-Motor Assessment Scale. Acta Paediatr 2008; 97:21-26.
Da Costa SP, van dE-H, Bos AF. Sucking and swallowing in infants and diagnostic tools. J Perinatol 2008; 28:247-257.
Als H, Lawhon G, Duffy FH, McAnulty GB, Gibes-Grossman R, Blickman JG. Individualized developmental care for the very low-birth-weight preterm infant. Medical and neurofunctional effects [see comments]. JAMA 1994; 272:853-858.
Rommel N, De Meyer AM, Feenstra L, Veereman-Wauters G. The complexity of feeding problems in 700 infants and young children presenting to a tertiary care institution. J Pediatr Gastroenterol Nutr 2003; 37:75-84.
Premji SS, McNeil DA, Scotland J. Regional neonatal oral feeding protocol: changing the ethos of feeding preterm infants. J Perinat Neonatal Nurs 2004; 18:371-384.
Medoff-Cooper B, Rankin K, Zhuoying L, Liu L, White-Traut R, Multisensory Intervention for Preterm Infants Improves sucking Organization, Advances in Neonatal Care, vol. 15, No. 2 (2015) pp. 142-149.
Lau C, Alagugurusamy R, Schanler RJ, Smith EO, Shulman RJ. Characterization of the developmental stages of sucking in preterm infants during bottle feeding . Acta Paediatr 2000; 89:846-852.
Poore M, Zimmerman E, Barlow SM, Wang J, Gu F. Patterned orocutaneous therapy improves sucking and oral feeding in preterm infants. Acta Paediatr 2008; 97:920-927.
Gewolb IH, Vice FL. Maturational changes in the rhythms, patterning, and coordination of respiration and swallow during feeding in preterm and term infants. Dev Med Child Neurol 2006; 48:589-594.
Lau C, Smith EO, Schanler RJ. Coordination of suck-swallow and swallow respiration in preterm infants. Acta Paediatr 2003; 92:721-727.
Lau C, Sheena HR, Shulman RJ, Schanler RJ. Oral feeding in low birth weight infants. J Pediatr 1997; 130:561-569.
McCain GC. An evidence-based guideline for introducing oral feeding to healthy preterm infants. Neonatal Netw 2003; 22:45-50.
Scheel CE, Schanler RJ, Lau C. Does the choice of bottle nipple affect the oral feeding performance of very-low-birthweight (VLBW) infants? Acta Paediatr 2005; 94:1266-1272.
Fucile S, Gisel E, Lau C. Oral stimulation accelerates the transition from tube to oral feeding in preterm infants. J Pediatr 2002; 141:230-236.
Fucile S, Gisel EG, Lau C. Effect of an oral stimulation program on sucking skill maturation of preterm infants. Dev Med Child Neurol 2005; 47:158-62.
Rocha AD, Moreira ME, Pimenta HP, Ramos JR, Lucena SL. A randomized study of the efficacy of sensory-motor-oral stimulation and non-nutritive sucking in very low birthweight infant. Early Hum Dev 2007; 83:385-388.
Lau C. Oral Feeding in the Preterm Infant. NeoReviews 2006; 7:e19-e27.
Lau C., Smith EO. A Novel Approach to Assess Oral Feeding Skills of Preterm Infants, Neonatology 2011;100:64-70.
Lau C., et. al. A self-paced oral feeding system that enhances preterm infants' oral feeding skills, J Neonatal Nursing 2014;08.004.
Lau C., Smith EO. Interventions to improve the oral feeding performance of premature infants, Acta Paediatrica 2012;101:e269-e274.
Fucile S, Gisel EG, Mcfarland DH, and Lau C, Oral and non-oral sensorimotor interventions enhance oral feeding performance in preterm infants, Dev. Med. Child Neurology, 2011;53:829-835.
Field T, et al., Tactile/kinesthetic stimulation effects on preterm neonates. Pediatrics 1986;77:654-658.
Lau C., Fucile S., Gisel EG, Impact of nonnutritive oral motor stimulation and infant massage therapy on oral feeding skills of preterm infants, J Neonatal-Perinatal Medicine 2012;5:311-317.
Jain, Lucky, et. al, Energetics and mechanics of nutritive sucking in the preterm and term neonate, J of Pediatrics 1987;111:6,part 1, 894-898.
Rasch S, Sangild PT, Gregersen H, Schmidt M, Omani T, Lau C., The preterm piglet—a model in the study of esophageal development in preterm neonates. Acta Paediatr 2010; 99: 201-208 (doi:10.1111/i.1651-2227.2009.01564.x).
Lau C, Bhat J, Potak D, Schanler RJ., Oral Feeding Skills of Late Preterm Infants are correlated with Hospital Length of Stay. J Ped Moth Care 2015; 1:102.
Nyengele G, Zemel J, The Neonur: a Mobile System to Monitor Neonatal Nursing Characteristics, U. Penn, "SUNFEST", Jul. 2013.
Nyengele G, Zemel J, A Mobile System to Monitor Neonatal Nursing Characteristics, U. Penn, "SUNFEST", Jul. 2013.

(56) References Cited

OTHER PUBLICATIONS

Amaizu N, Shulman RJ, Schanler RJ, Lau C, Maturation of oral feeding skills in preterm infants, Acta Paediatrica Aug. 2007, 97, pp. 61-67.

Fusile S, Gisel E, Schanler RJ, A controlled-flow vacuum free bottle system enhances preterm infants' nutritive sucking skills, Dysphagia (2009) 24:145-151.

Lau C, Smith EO, Interventions to improve the oral feeding performance of preterm infants, Acta Paediatrica, Feb. 2012, 101, pp. e269-274.

Lau C, Is there an advantage for preterm infants to feed orally in an upright or sidelying position?, Neonatal Nurses Association, Apr. 2012, pp. 28-32.

Lau C, Fucile S, Schanler RJ, A self-paced oral feeding system that enhances preterm infants' oral feeding skills, Jnl. Neonatal Nursing, Aug. 2014, http://dx.doi.org/10.1016/j.jnn.2014.08.004.

Lau C, Smith EO, A novel approach to assess oral feeding skills of preterm infants, Neonatology, Jan. 2011;100:64-70.

Kron RE, Ipsen J, Goddard KE, Consistent Individual Differences in the Nutritive Sucking Behavior of the Human Newborn, Psychosomatic Medicine, vol. XXX, No. 2, 1968, pp. 151-161.

Lau C, Bhat K, Potak D, Schanler RJ, Oral feeding assessment predicts length of hospital stay in late preterm infants, J. Ped. Moth. Care, vol. 1, Issue 1:102, Apr. 2015, pp. 1-4.

Wicklund E, New sensors help NICU clinicians measure an infant's feeding ability, http://www.nfant.com/#about, Oct. 20, 2015.

Fucile S, McFarland DH, Gisel EG, Lau C, Oral and nonoral sensorimotor interventions facilitate suck-swallow-respiration functions and their coordination in preterm infants, Early Human Development 88 (2012) 345-350.

Lau C, Schanler RJ, Oral Motor Function in the Neonate, Neonatal Gastroenterology, vol. 23, No. 2, Jun. 1996. pp. 161-178.

Waterland A, Berkowitz RI, Stunkard AJ, Stallings VA, Calibrated-orifice nipples for measurement of infant nutritive sucking, J. Pediatrics Mar. 1998;132:523-526.

Tamilia E, Taffoni F, Formica D, Ricci L, Schena E, Keller F, Guglielmelli E, Technological solutions and main indices for the assessment of newborns' nutritive sucking: A Review, Sensors Jan. 2014, 14, 634-658; doi:10.3390/s140100634.

Wang YL, Hung JS, Wang LY, Ko MJ, Chou W, Kuo HC, Lin BS, Development of a wireless oral-feeding monitoring system for preterm infants, IEEE Jnl. Biomedical and Health Informatics, Vo. 19, No. 3, May 2015, pp. 866-873.

Wang YH, Lee CY, Chiang CM, A MEMS-based air flow sensor with a free-standing micro-cantilever structure, Sensors 2007, 7, 2389-2401.

Selley WG, Ellis RE, Flack FC, Brooks WA, Coordination of sucking, swallowing and breathing in the newborn: Its relationship to infant feeding and normal development, British Jnl. of Disorders of Communication, 25, 311-327 (1990).

Goldfield EC, Wolff PH, Schmidt RC, Dynamics of oral-respiratory coordination in full-term and preterm infants: 1. Comparisons at 38-40 weeks postconceptual age, Developmental Science 2:3 (1999), pp. 363-373.

\* cited by examiner

Table 5: Nine Scenarios

| Scenario | FR(0-5) | FR(6-10) | FR(11-15) | FR(16-20) | OFS | Range OT | Comments | Recommendations |
|---|---|---|---|---|---|---|---|---|
| 1 | ≥ 10ml/min green | ≥ 10ml/min green | ≥ 10ml/min green | ≥ 10ml/min green | 4 | 100% | No intervention | None |
| 2 | ≥ 10ml/min green | = 5-9ml/min yellow | = 5-9ml/min yellow | = 5-9ml/min yellow | 3-4 | 63%-93% | Adequate Skills Inadequate endurance | Allow 2 days to mature No progress →Skill & Training |
| 3 | ≥ 10ml/min green | = 5-9ml/min yellow | = 5-9ml/min yellow | = 0-4 ml/min red | 3 | 85%-50% | Adequate Skills Inadequate endurance | Training |
| 4 | ≥ 10ml/min green | = 5-9ml/min yellow | = 0-4 ml/min red | STOP | 3 | 60%-37% | Adequate Skills Inadequate endurance | Training |
| 5 | ≥ 10ml/min green | = 0-4 ml/min red | STOP | | 3 | 37%-25% | Adequate Skills Inadequate endurance | Training |
| 6 | = 5-9ml/min yellow | = 5-9ml/min yellow | = 5-9ml/min yellow | = 5-9ml/min yellow | 3-4 | 90-50% | Give time to mature | Allow 2 days to mature No progress →Skill & Training |
| 7 | = 5-9ml/min yellow | = 5-9ml/min yellow | = 0-4 ml/min red | STOP | 1-2 | 57%-25% | Inadequate Skills Inadequate endurance | Skill & Training |
| 8 | = 5-9ml/min yellow | = 0-4 ml/min red | STOP | | 1-2 | 35%-13% | Inadequate Skills Inadequate endurance | Skill & Training |
| 9 | = 0-4 ml/min red | STOP | | | 1-2 | 13%-0% | Inadequate Skills Inadequate endurance | Skill & Training |

FIG. 14

SYSTEM AND METHODS FOR ASSESSING A PERSON'S ORAL FEEDING SKILLS DURING ORAL FEEDING

CROSS-REFERENCE TO RELATED APPLICATIONS

None

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

This invention pertains to the oral feeding of all infants, be they born term or preterm, when bottle- and breast-fed.

Description of Related Art

There are no well-defined objective means to identify the level of oral feeding skills (OFS) in newborn infants, be they born prematurely or at term. Assessing infants' oral feeding skills is difficult due to the lack of well-defined outcomes and available technology. The main dilemma that caregivers face when addressing oral feeding difficulties pertains to an infant's ability to complete his/her feedings safely and efficiently. Term infants are expected to feed by mouth readily. However, some of them do encounter oral feeding difficulties, be it breast or bottle, which lead their caregivers to seek medical advices, e.g., pediatricians, feeding therapists, feeding disorders clinics. The existence of bottle feeding difficulties is reflected by the existence of 'special' bottles in the general marketplace labeled as reducing 'colic', closest to mother's breast, etc.

For infants born prematurely in hospitals, bottle-feeding is a more complex problem. Due to their immaturity, they are generally tube-fed at first. They are transitioned to oral feeding at a later time when their oral feeding skills are believed to be adequate to ensure safety and competency. Attainment of independent oral feeding being one of the criteria recommended by the American Academy of Pediatrics for hospital discharge [1], their inability to feed by mouth safely and competently will understandably delay their hospital discharge and mother-infant reunification, while increasing medical cost and maternal stress [2, 3]. For all infants who demonstrate oral feeding difficulties, be they term or preterm, it is difficult to identify the causes for such difficulties due to the lack of evidence-based objective tool(s) that assesses their oral feeding skills.

A variety of descriptive and objective scales for both categories of infants have been developed. A descriptive scale uses sensory, e.g., visual, and behavioral observations to assess the appropriateness of oral feeding skills, e.g., the Neonatal Oral-Motor Assessment Scale (NOMAS) developed by Palmer; and the Early Feeding Skill assessment (EFS) by Thoyre, et. al [4, 5]. The accuracy of this type of approach has been debated due to their subjective nature and lack of direct measure of objective outcomes. Multidisciplinary assessments of an infant's potential ability to oral feed are used on the basis that it would be more accurate if feedback from the varied caregivers involved in his/her care were taken into account [9, 10]. For instance, Als [8] has recommended the use of a developmental care approach incorporating feedback from the different members of an infant's caregivers' team would optimize infant's oral feeding on the basis that if an infant's clinical stability, organization, and competence could be enhanced, his/her physiologic and behavioral expression would be optimized.

More objective and quantitative evaluations of oral feeding skills are illustrated by tools that have been developed to measure outcomes, such as: nutritive and nonnutritive sucking patterns and their rhythmicity, sucking force, and coordination of suck-swallow-respiration, and esophageal function [11-15, 30]. However, these approaches necessitate the use of specialized research equipment not readily available to health professionals. Therefore, due to the difficulty in identifying the maturity level of infant oral feeding skills (OFS), oral feeding assessments remain in the hands of caregivers, feeding therapists and physicians who rely primarily on subjective scales, many lacking evidence-base support.

In an earlier study [16] conducted by the Inventor (Chantal Lau) at the first oral feeding of infants born prematurely between 26 and 30 weeks gestation (GA), she defined an infant's OFS as a function of two parameters: (1) their combined proficiency (PRO(5)), calculated as the ratio (%) of volume (ml) taken (ingested, transferred) during the first 5 min divided by total volume of liquid prescribed (ml), and (2) the overall (average) rate of milk transfer ($RT_{20}$, ml/min), calculated as the volume of liquid taken over an entire feeding period (ml) divided by the total length of the feeding period, which generally is 20 minutes (min). The first parameter, PRO(5), being monitored during the first 5 minutes of a feeding, was used as an index of infants' true (intrinsic) feeding ability (i.e., when fatigue is minimal). The second parameter, (Rate of Transfer), RT(20), (=overall average flow rate) being monitored over an entire 20-min feeding duration, was used as an indirect measure of infant's lack of endurance as his OFS skills would weaken with fatigue.

In two studies by Lau [16, 23], it was reasoned that during a feeding session the average rate of milk transfer (i.e., ml/min) would decrease over time if infants' true skills were held back due to increasing fatigue. The overall feeding performance or competency (overall percentage of fluid transferred, OT), is calculated as the ratio (%) of actual total volume (ml) taken by the infant at the end of a feeding session, $V_{total}$, divided by the volume of formula initially prescribed, $V_{prescribed}$. Feeding was defined as being "successful" if infants completed greater than or equal to 80% of their prescribed feeding volume (i.e., OT 80%). Note that OT is equivalent to PRO(20) measured at the end of a feeding session. Based on their performance, Lau distinguished four levels of Oral Feeding Skills (OFS) for Very Low Birth Weight (VLBW) infants (i.e. those born less than 2.5 Kg), "Level 1, 2, 3, and 4" as delineated by two cutoff thresholds: (a) $RT_{20}$ greater or less than 1.5 ml/min and (b) $PRO_5$ greater or less than 30% for premature infants (<34 weeks gestation; and greater or less than 40% for late preterm and term infants (≥34 weeks gestation). [23, 31]. The cutoff levels for these two parameters, $PRO_5$ and $RT_{20}$, were based on the observations that VLBW infants demonstrating $RT_{20}$ 1.5 ml/min and $PRO_5$ 30% (or 40%, depending on gestational age) were most likely to be successful at feeding, i.e., having an overall transfer (OT)≥80% of their initial prescribed volume; as well as attaining independent oral feeding faster than counterparts whose $PRO_5$ were <30% and/or $RT_{20}$<1.5 ml/min [23]. Compared to this first group, infants with $RT_{20}$≥1.5 ml/min and PRO<30%, or $RT_{20}$<1.5 ml/min and PRO 30% also fed successfully (OT≥80%), but attained independent oral feeding at a slower pace. Infants with $RT_{20}$<1.5 ml/min and $PRO_5$<30% were not successful at feeding (OT<80%) and were the slowest group to reach independent oral feeding during their hospitalization thereby prolonging their stay in the neonatal intensive care unit (NICU).

The goal of the study done by the Inventor [23] was to determine whether the defined OFS levels can be used as an objective tool for assessing preterm infants' oral feeding skills; in particular to determine if OFS, as reflected by the combination of proficiency (PRO(5), % ml taken the first 5 min/ml prescribed) and rate of milk transfer during a 20-min feeding session (RT(20), ml/min), correlates with gestational age (GA), oral feeding performance (OT, % ml taken during a feeding/ml prescribed), or days from start to independent oral feeding (SOF-IOF). Lau's working premise was that $PRO_5$ is reflective of infants' true or actual feeding skills when fatigue is minimal and $RT_{20}$, monitored over an entire feeding session, is reflective of their overall skills when fatigue comes into play. Lau hypothesized that: (1) the more mature an infant's OFS level, the better his/her OT (Overall Transfer, %) at that feeding; (2) the more premature an infant (earlier GA), the more immature his/her OFS level; and (3) the better the OFS level is, the faster independent oral feeding will be attained.

Methods [23]:

Infants (26 to 36 weeks GA) with prematurity as their principal diagnosis were recruited and monitored at their $1^{st}$ oral feeding. GA was divided into 3 strata, 26-29, 30-33, and 34-36 weeks GA. OFS was divided into 4 levels delineated by $PRO_5$ or <30% or 40%) and $RT_{20}$ or <1.5 ml/min). ANOVA with post-hoc Bonferroni and multiple regression analyses were used.

Results [23]:

Lau's hypotheses were confirmed. OFS levels were: (a) positively correlated with an infant's feeding performance; i.e., the better the OFS levels, the greater the OT and the shorter the feeding duration; (b) positively correlated with GA strata, i.e., the less premature the infant, the more mature his/her skills; and (c) inversely associated with days from SOF to IOF, i.e., the better the skills, the faster the attainment of independent oral feeding. In summary, OFS levels were correlated with GA, OT, $PRO_5$; and days from SOF-IOF were associated with OFS and GA; whereas $RT_{20}$ was only with OFS levels. The correlations of OT and $PRO_5$ with GA can be explained by the greater proportion of infants at the older GA strata, who being more developmentally mature, naturally demonstrated more mature OFS levels. The observation that $RT_{20}$ was associated with OFS, but not GA, suggests that rate of milk transfer is primarily regulated by an infant's feeding aptitude, e.g., sucking skills, swallowing skills, suck-swallow-respiration coordination, and/or endurance.

Conclusions [23]:

OFS is a novel objective indicator of infants' feeding ability that takes into account infants' skills and endurance. Its use does not require any special equipment or tool but, rather, the simple monitoring of volume taken at different times during a feeding session. As a clinical tool, it can help caretakers to monitor infants' skills as they transition to oral feeding, and to identify oral feeding issues arising from immature skills and/or poor endurance. Infants with high $PRO_5$ (≥30%)n and $RT_{20}$ (≥1.5 ml/min), i.e. OFS level 4 perform better than their counterparts with low $PRO_5$ (<30%, OFS levels 1 and 2) or low $RT_{20}$ (<1.5 ml/min, OFS levels 1 and 3). The observation that infants at OFS levels 2 and 3 had similar OT suggests that both true feeding skills and endurance are equally important in determining oral feeding success. From this, one may speculate that enhancing both factors would optimize overall feeding. This is supported by the observations that OT, $PRO_5$, $RT_{20}$, and feeding duration of infants at OFS level 4, were superior to those of their counterparts at OFS levels 1 to 3.

In summary, we propose that the use of OFS levels is a useful indicator to assist caregivers in determining infants' oral feeding aptitude. It is novel and offers an objective assessment of oral feeding skills whether they are monitored at a $1^{st}$ oral feeding experience, or on a regular basis as infants mature and advance towards independent oral feeding (i.e., no tube feeding). Against this background, the present invention was developed.

Note: all References listed herein are hereby incorporated by reference in their entirety.

SUMMARY OF THE INVENTION

The present invention comprises a system and methods for assessing infant oral feeding (OFS) skills during oral feeding. It is also a "Smart" baby feeding system comprising a smart baby bottle wirelessly connected to a smart device (e.g., smart phone, tablet, laptop, etc.). "Smart" means that it provides feedback (both immediate and retrospective analytical) to the caregiver: (1) as to when to stop feeding the baby; (2) as to the quality/efficiency and success of the feeding; (3) as to the optimum way to feed this particular baby with his/her unique strengths and weaknesses; and (4) as to the likelihood that the baby would benefit from professional attention. It is also capable of yielding analytical data for the use of caregivers, professionals, and clinicians within the clinical context if desired. The invention will help optimize the feeding performance, safety, and competency of the baby while protecting him/her from harmful feeding practices that might be detrimental to (impact negatively on) his/her long-term mental and motor development and/or to mother-infant dyad.

The chain of technologies that make this work starts with a notification display on the bottle (and/or on a remote device) that is akin to a smartphone screen and/or vibration or auditory sound (e.g., a chime sound) when it receives a signal. This is the immediate feedback method to the caregiver and is based on the real time OFS level used by the infant during a feeding (OFS scale levels 1, 2, 3, 4). Signals may comprise information/message such as: "Feeding is Adequate", or "Stop Feeding", or "Feeding is Inadequate" (e.g., see "yellow light" in FIG. 14). The display screen is controlled by a micro-computer processing data from one or more sensors located in the feeding bottle or bottle nipple. The logic driving the display notifications comprises innovative algorithms that are unique to babies.

The data feeding the decision algorithms are derived from one or more sensors located anywhere on the bottle (teat, collar, body, base) and/or nipple. The whole assembly is self-contained and separable from the feeding bottle body (i.e., an independent instrumentation module) and may be transferred between bottles; or it may be a permanent feature of the bottle. The data collected can be uploaded to a remote processing device (a hand-held computer, e.g., smartphone, iPad, iPhone, Android, laptop, etc.) via a proprietary software program or "App" for storage and processing. The App includes algorithms that can analyze the history of a feeding in order to provide caregivers real time feedback on infant performance during a feeding, as well as long-term feedback through retrospective analyses of an infant's feeding history over time, thereby offering guidance as to differing oral feeding approaches that may be envisioned. These feeding approaches relate to the various evidence-based interventions that have been developed, which are based on where the difficulties lie, e.g., along the oro-gastric pathway (oral cavity, pharynx, lungs, esophageal, etc.). Different algorithms are provided that are customized for different infants based on their level of maturity, i.e., very premature, late preterm, term, and also infants with chronic conditions.

BRIEF DESCRIPTION OF THE SEVERAL VIEWS OF THE DRAWING(S)

FIG. 1 shows a map of an example of the partitioning of four oral feeding skill (OFS) levels according to a pair of performance parameters: (1) proficiency ($PRO_5$) and (2) rate of milk transfer ($RT_{20}$) used for very low birth weight infants. Cut-off values of 1.5 ml/min for $RT_{20}$; and 30% or 40% for $PRO_5$ are identified for infants born <34 weeks gestation and between 34-36 weeks gestation, respectively [23]

Figure 7:
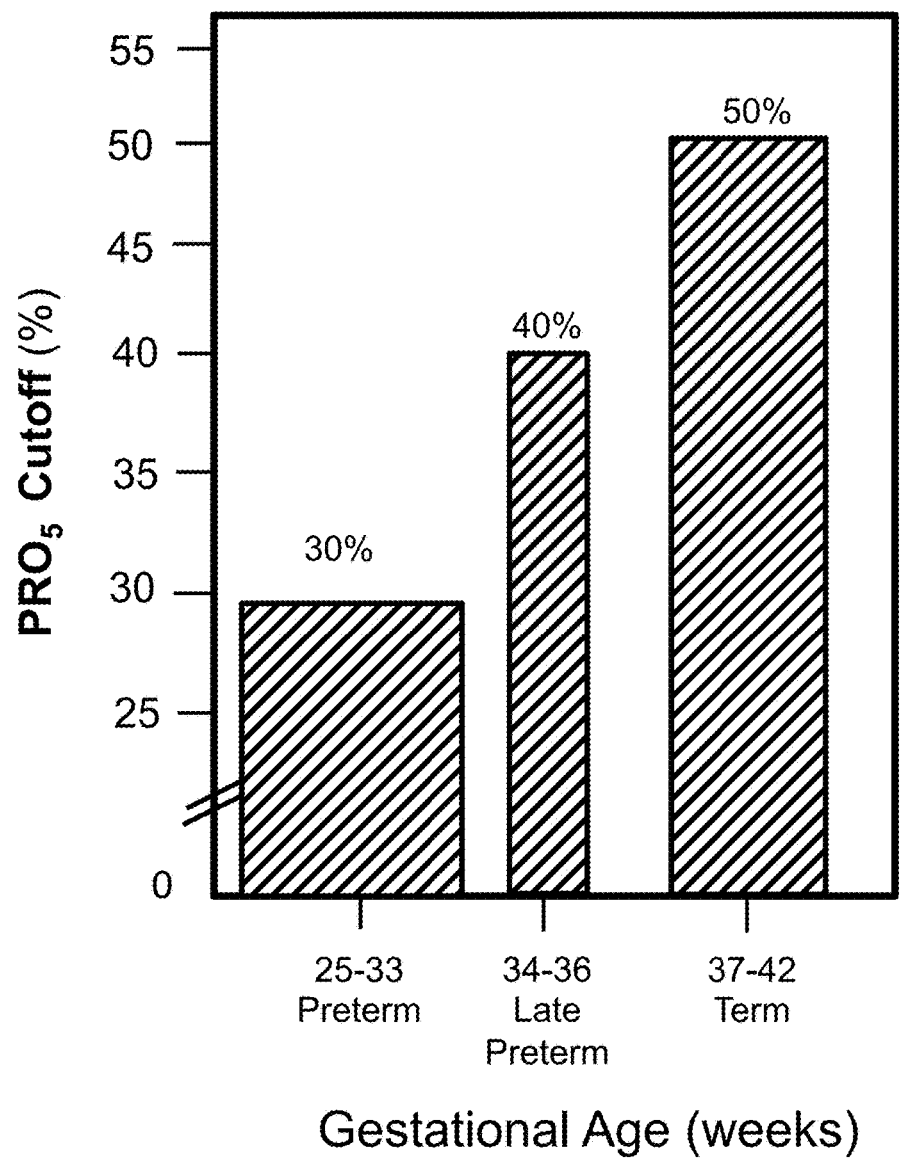

FIG. 7 plots the proficiency cutoff value, $PRO_5$, as a function of gestational age.

Figure 8:
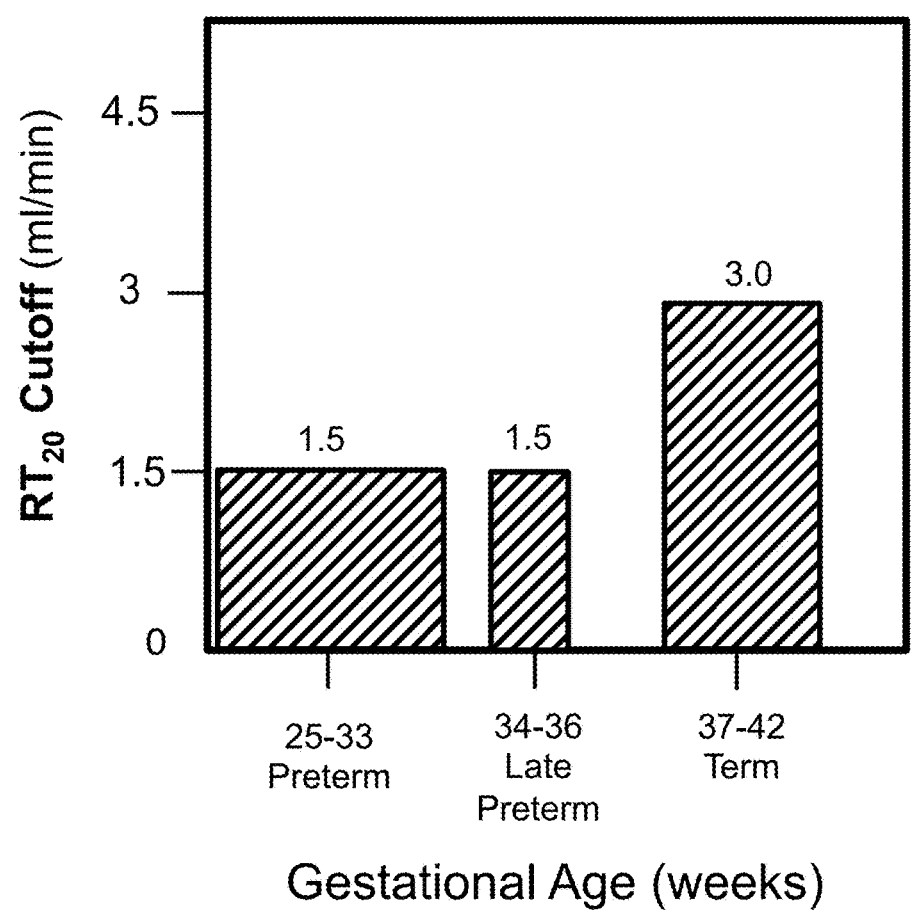

FIG. 8 plots the transfer rate cutoff value, $RT_{20}$ (ml/min), as a function of gestational age in weeks.

Figure 9:
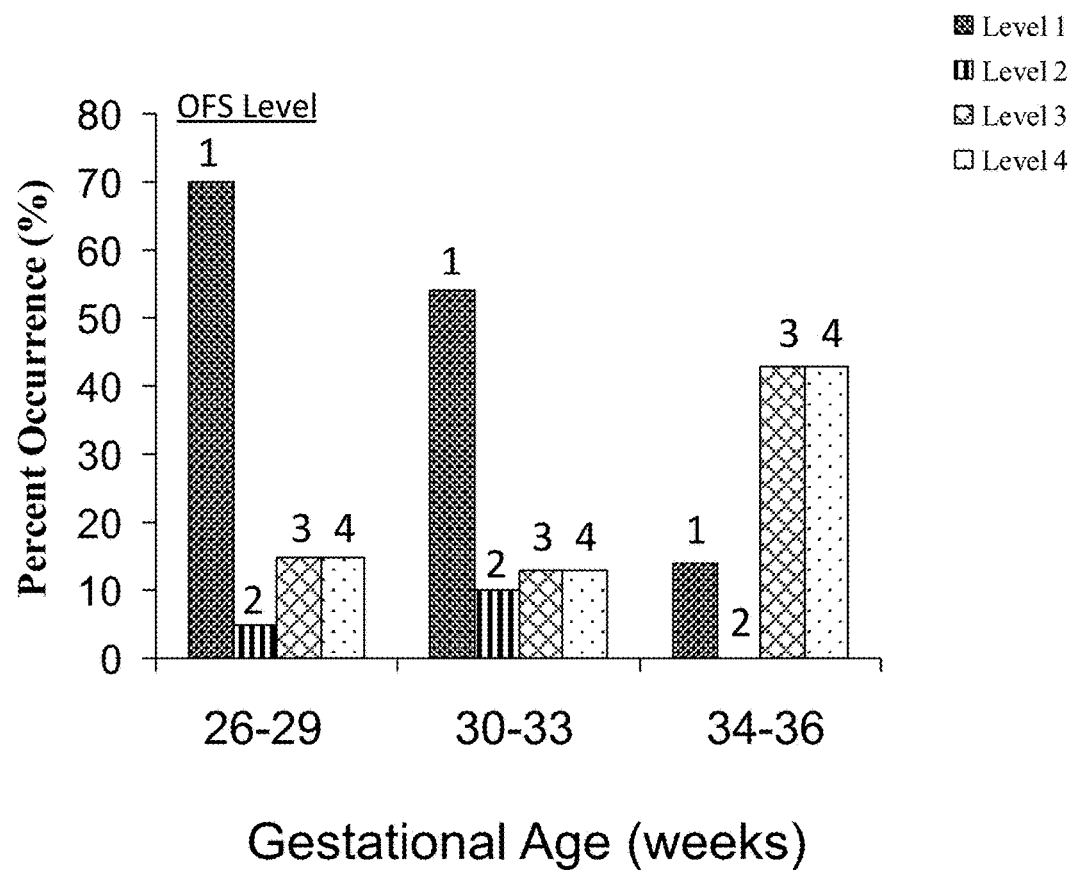

FIG. 9 shows the percent distribution (percent occurrence) of oral feeding skill (OFS) levels by gestational age GA stratum in infants born between 26 and 36 weeks gestation at their very first oral feeding experience [23].

Figure 10:
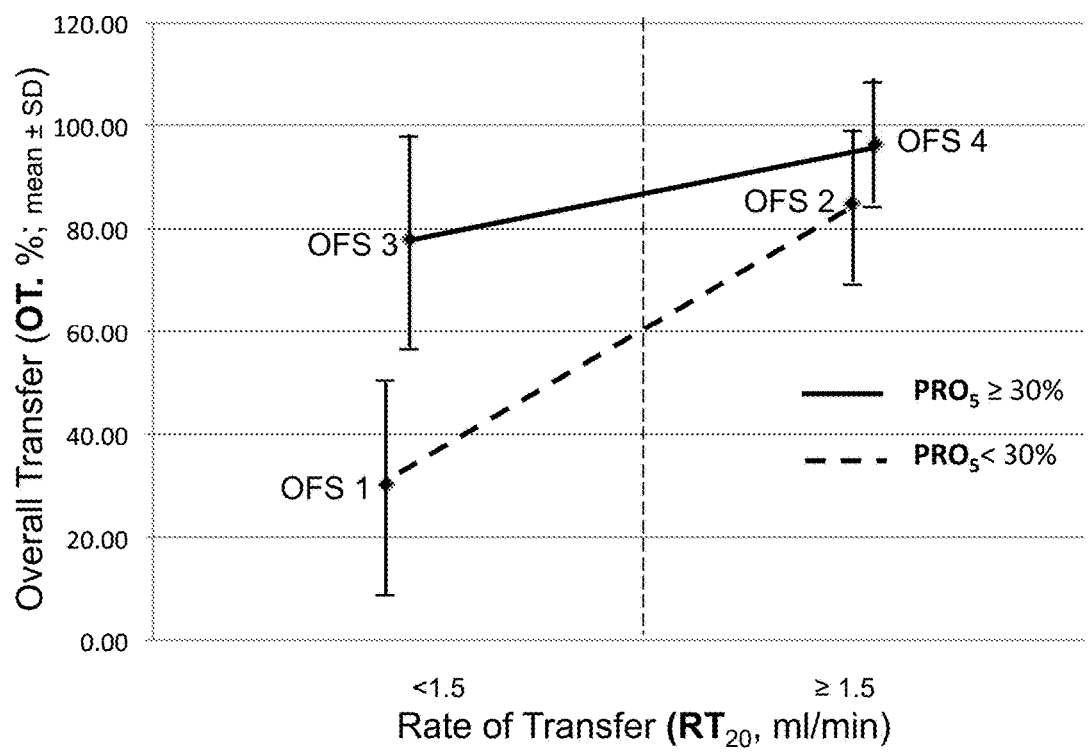

FIG. 10 shows Overall Transfer (OT, %) of infants with high vs low actual feeding skills ($PRO_5$ greater/less than 30%) vs. endurance ($RT_{20}$ greater/less than 1.5 ml/min) for very low birth weight (VLBW) infants born between 26 and 36 weeks gestation at their very first oral feeding experience [23].

Figure 11:
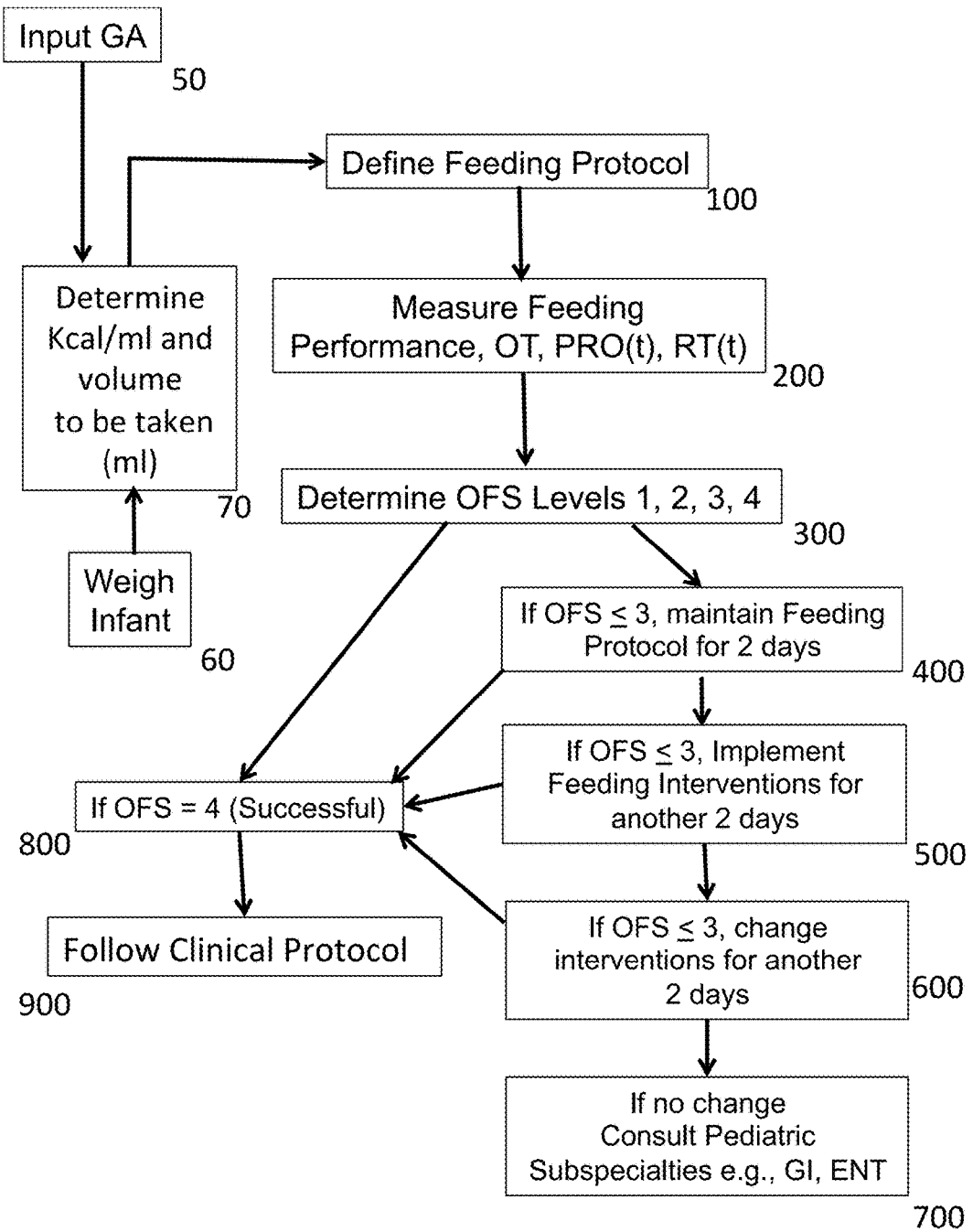

FIG. 11 shows a high-level algorithm for using the smart baby bottle with a smart device and embedded application.

Figure 12:
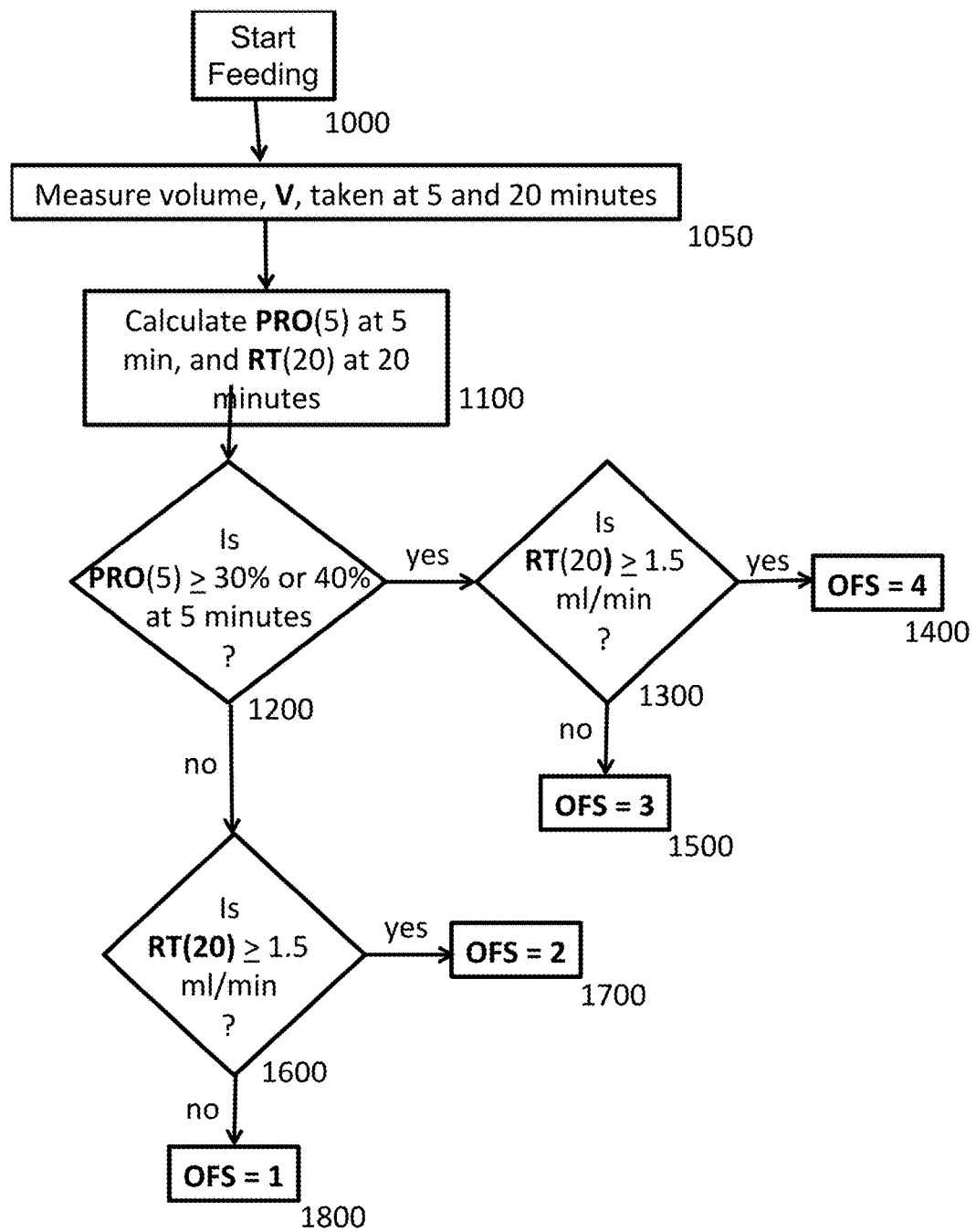

FIG. 12 shows an example of a first algorithm for determining OFS levels.

Figure 13:
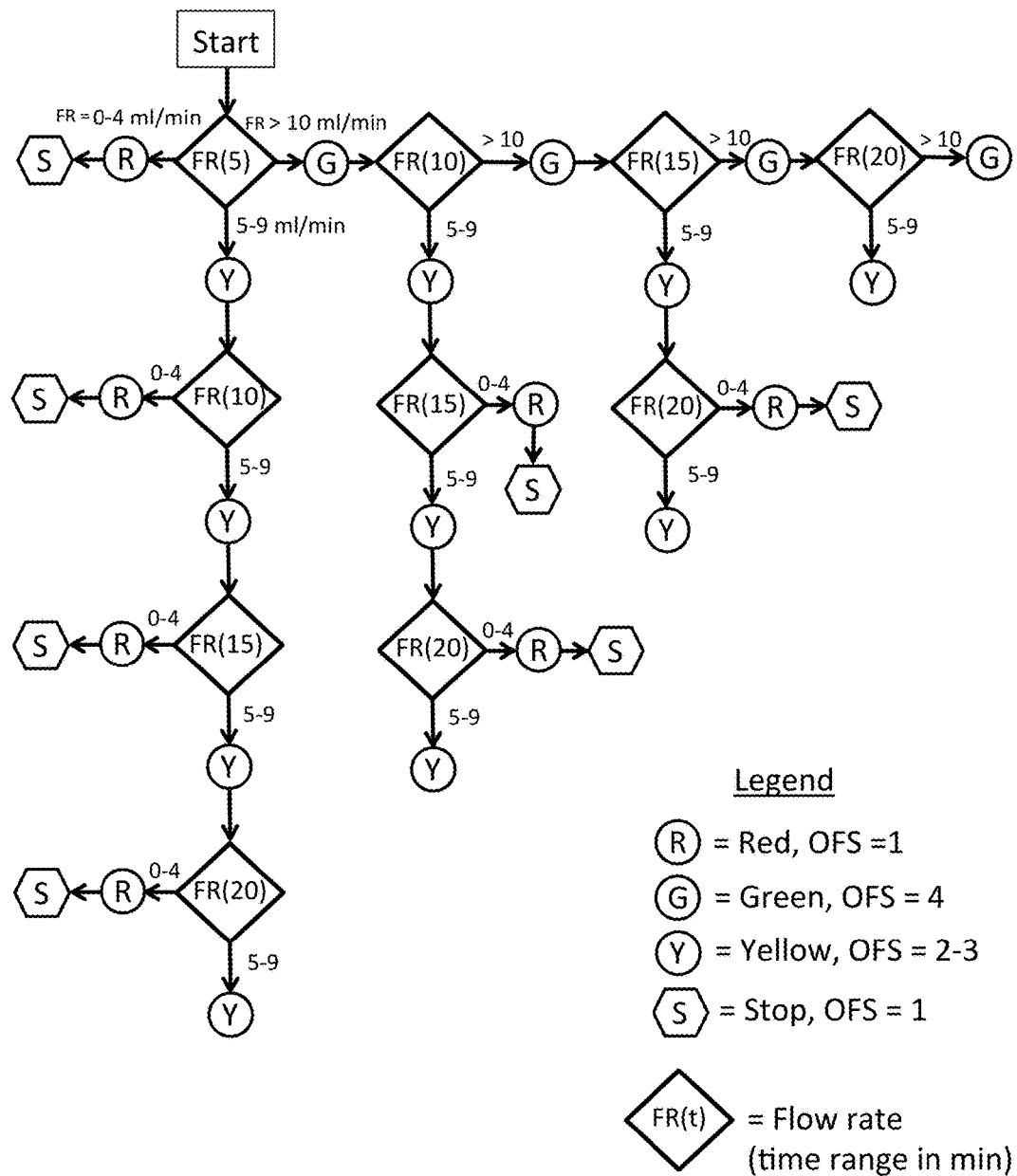

FIG. 13 shows a flow chart of a second example of an algorithm for sorting feeding performance into the four OFS levels 1, 2, 3, 4.

FIG. 14 shows Table 5 with 9 different scenarios, based on the flow chart of FIG. 13.

Figure 15:
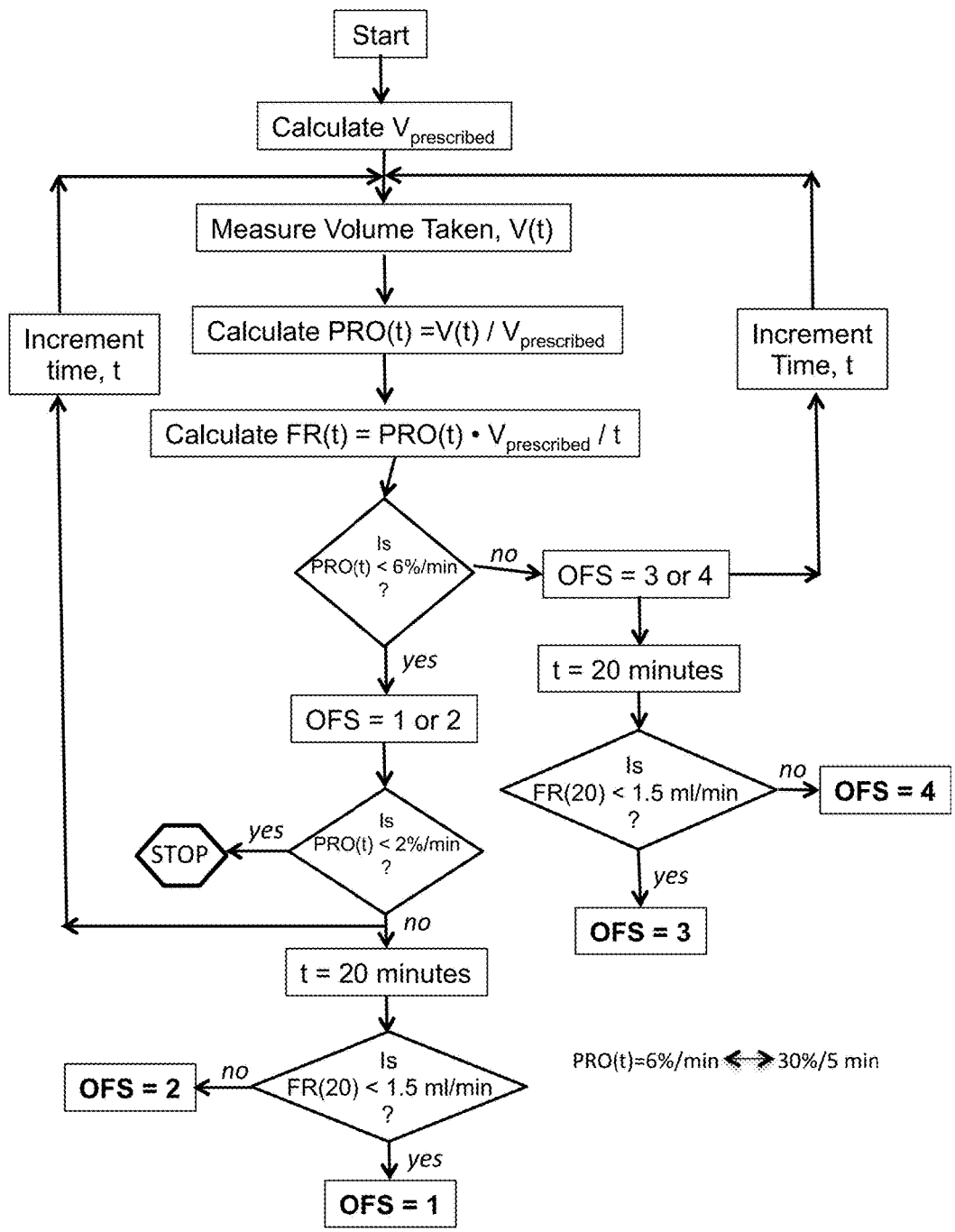

FIG. 15 shows an example of a third algorithm for determining OFS levels.

Figure 16:
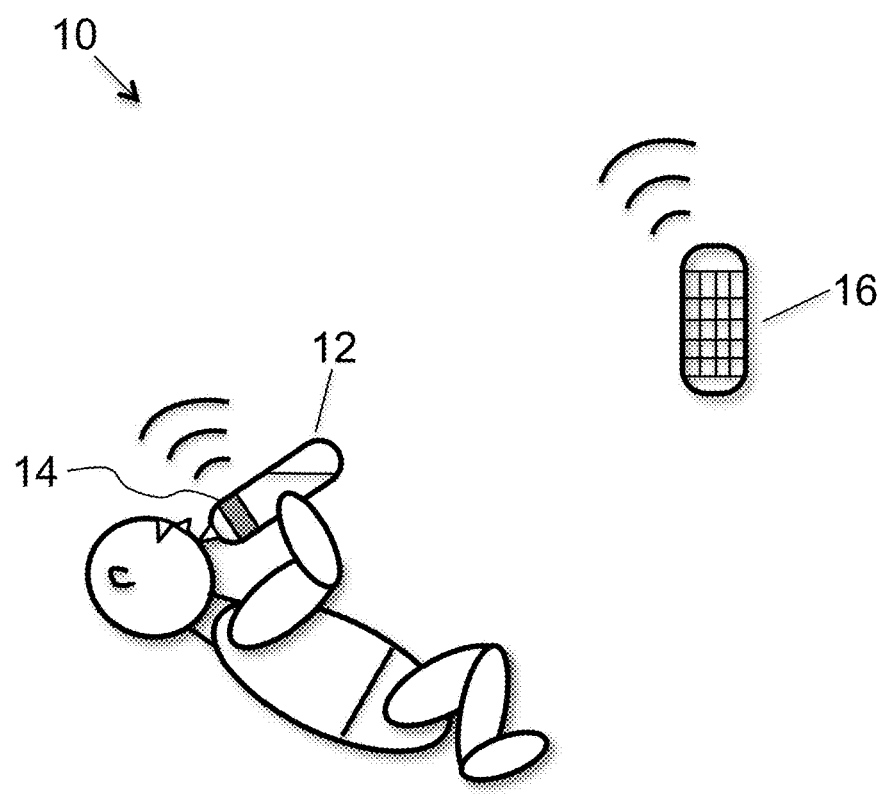

FIG. 16 shows a schematic perspective view of a smart infant feeding bottle system communicating wirelessly with a smart phone (e.g., smart tablet, or personal computer).

Figure 17A:
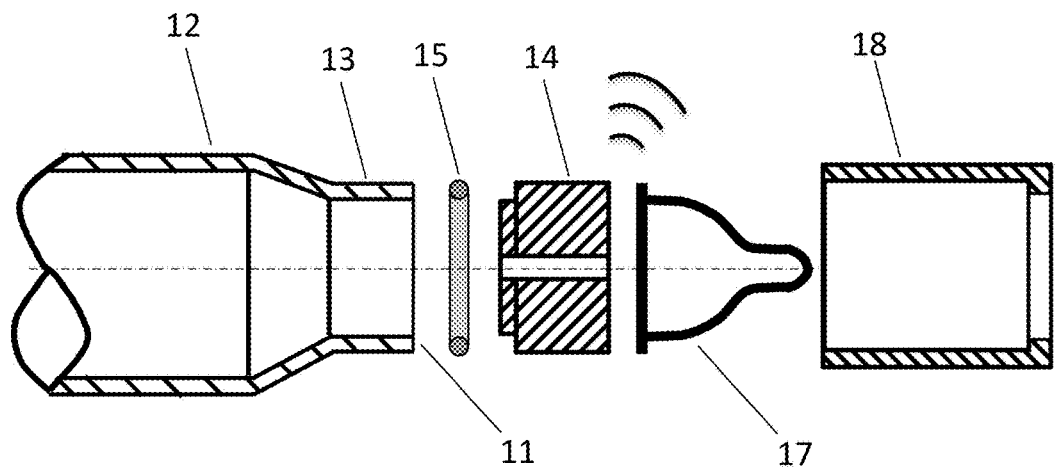

FIG. 17A shows a cross-section, exploded view of an embodiment of a flow rate module for an OMK system, according to the present invention.

Figure 17B:
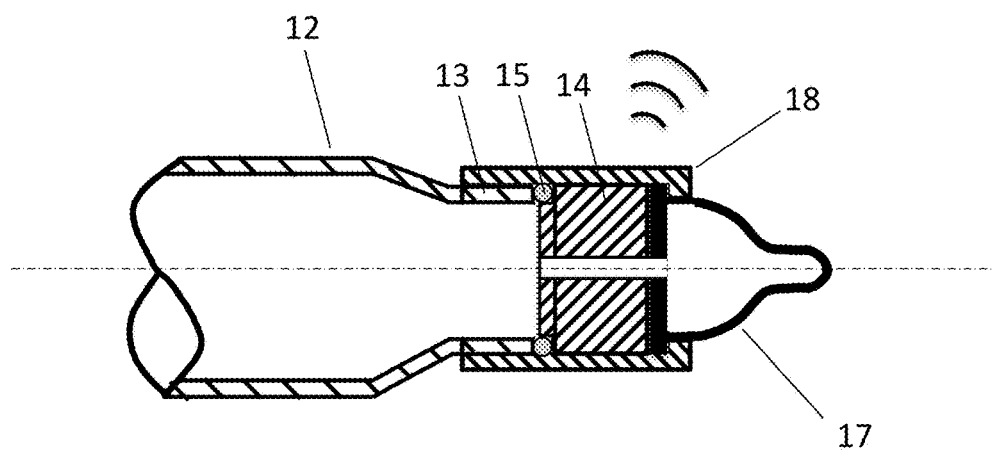

FIG. 17B shows a cross-section view of an assembly of FIG. 17A.

Figure 18A:
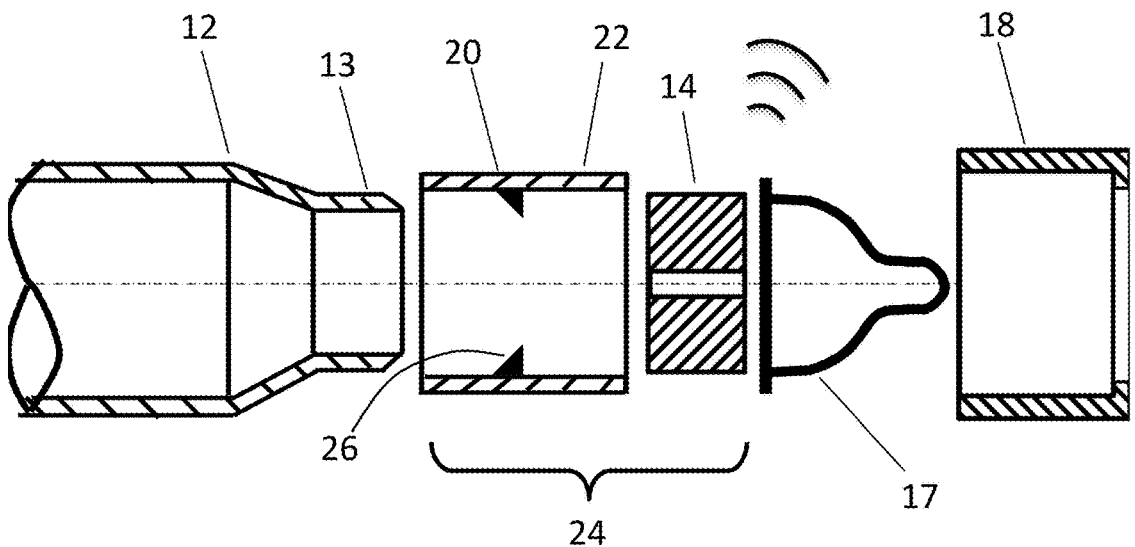

FIG. 18A shows a cross-section, exploded view of another embodiment of a flow rate module for an OMK system.

Figure 18B:
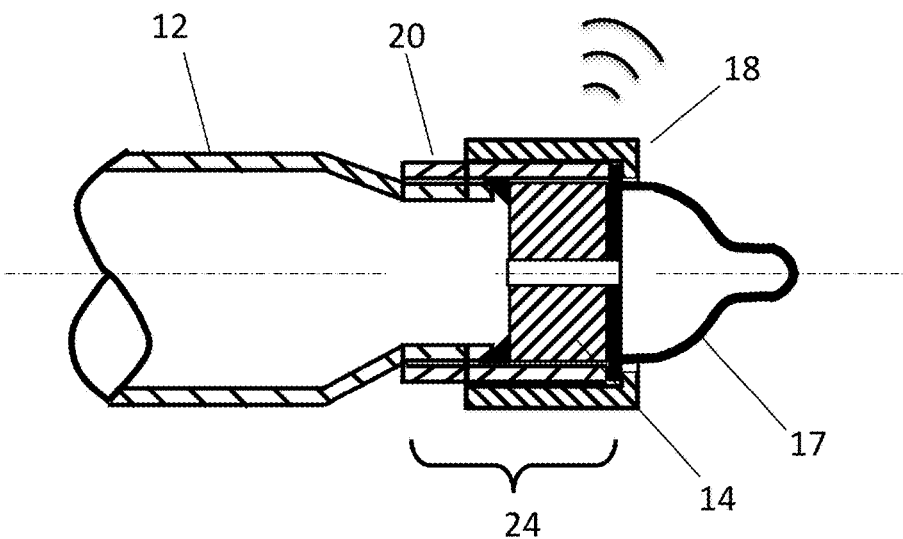

FIG. 18B shows a cross-section view of an assembly of FIG. 18A.

Figure 19A:
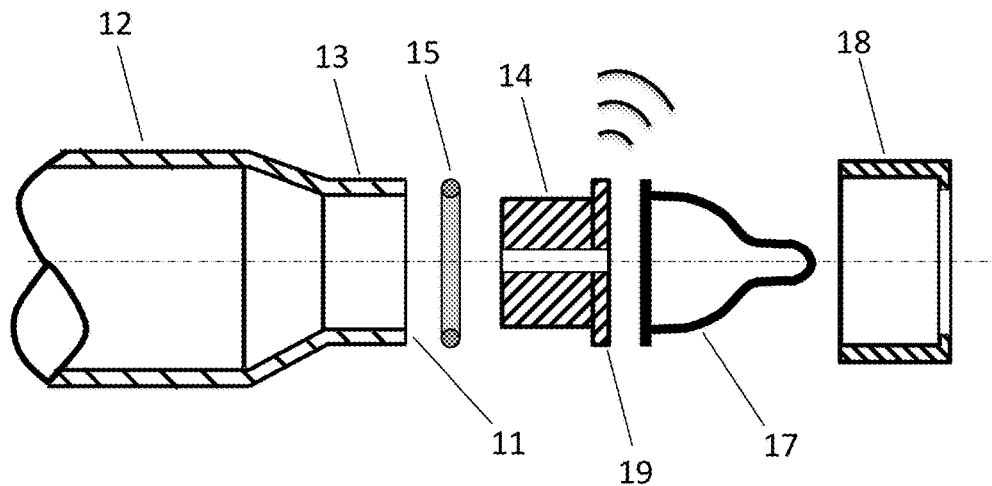

FIG. 19A shows a cross-section, exploded view of another embodiment of a flow rate module for an OMK system.

Figure 19B:
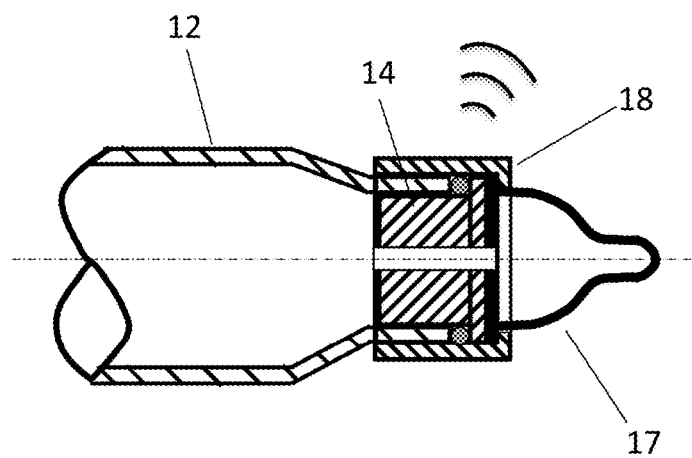

FIG. 19B shows a cross-section view of an assembly of FIG. 19A.

Figure 20:
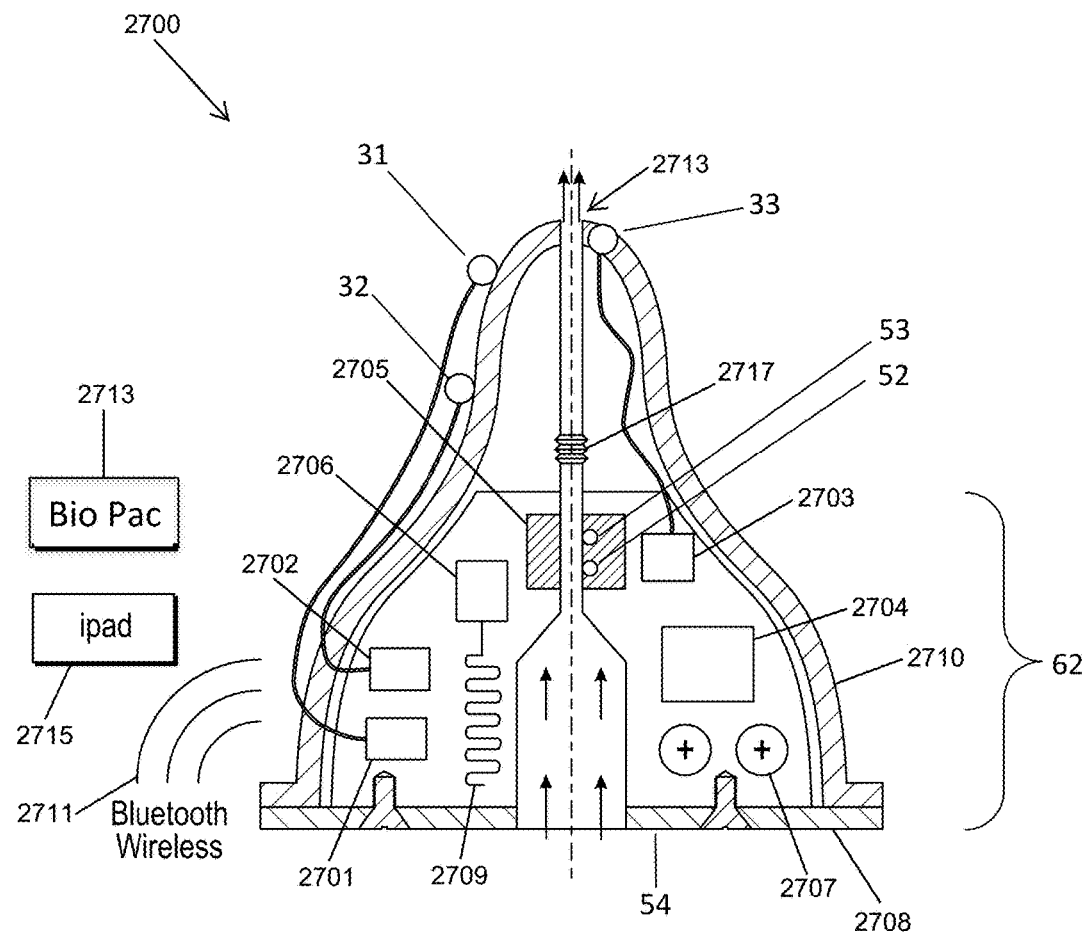

FIG. 20 shows a schematic micro flow rate sensor printed circuit board assembly for use inside of an infant feeding bottle (cover removed for clarity).

Figure 21A:
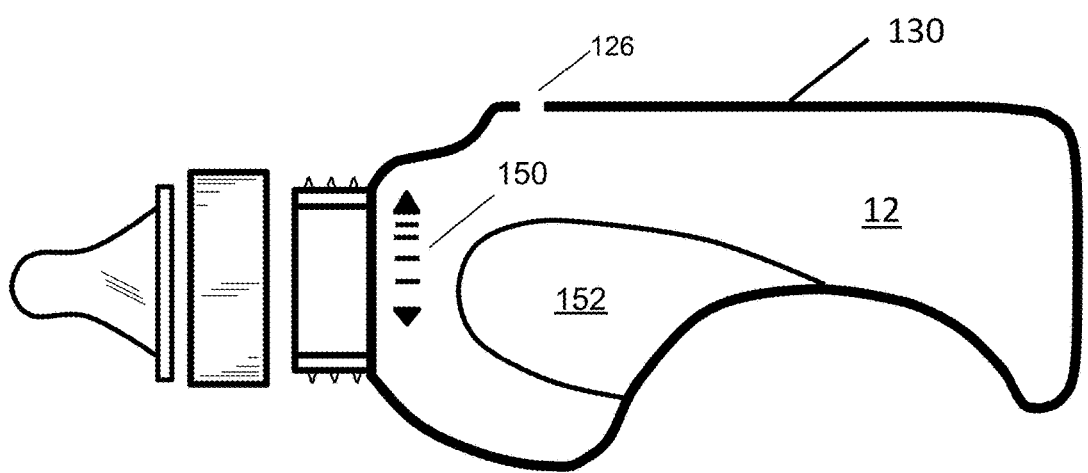
Figure 21B:
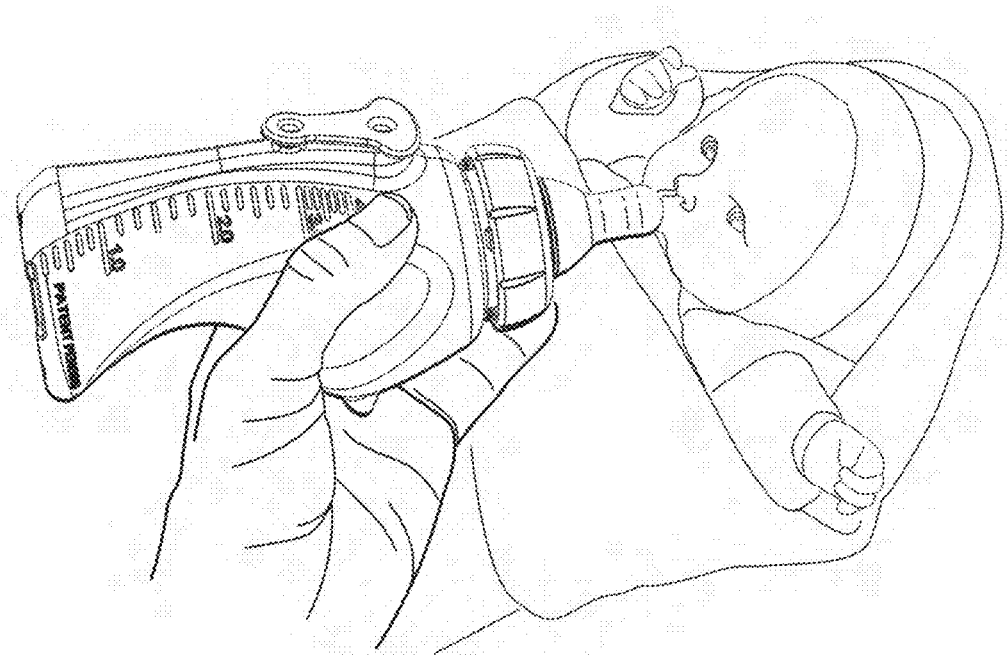

FIGS. 21-A,B,C show a cross-sectional view (FIG. 21A) and two overall views (FIG. 21B,C) of a self-paced ergonomic feeding bottle, according to the patent application mentioned above. The present invention can use this type of feeding bottle.

Figure 22:
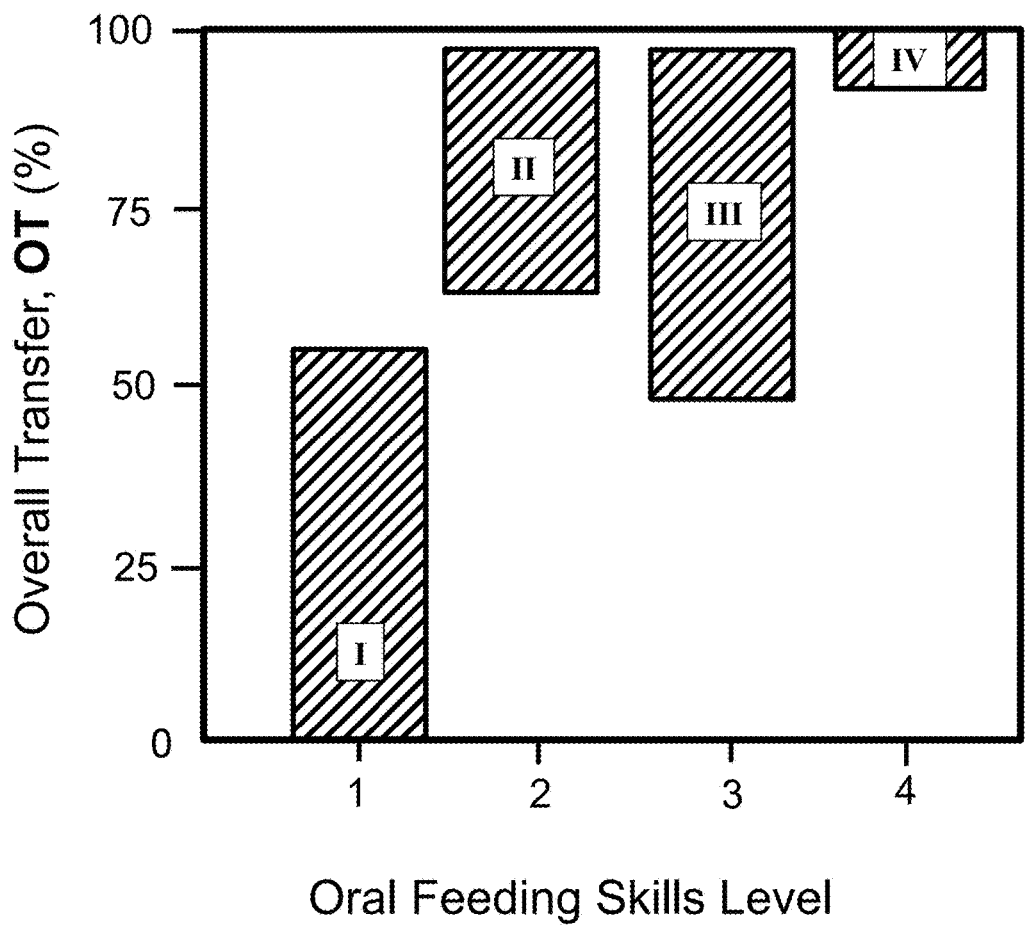

FIG. 22 shows a performance map for the OFS scale based on OT (%) from an earlier study [23]

Figure 23:
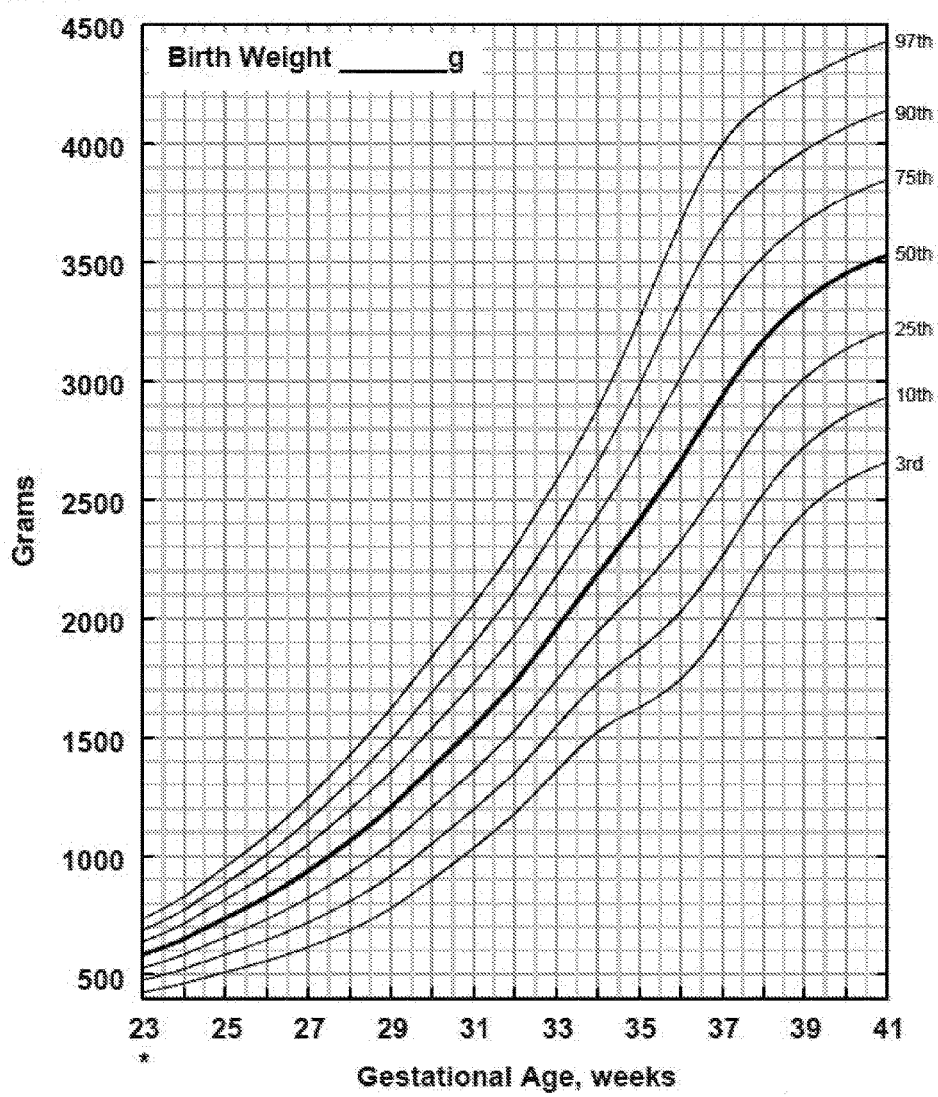

FIG. 23 shows a plot of infant birth weight (Kg) versus Gestational Ages (weeks) for female infants, including percentile ranges.

Figure 24:
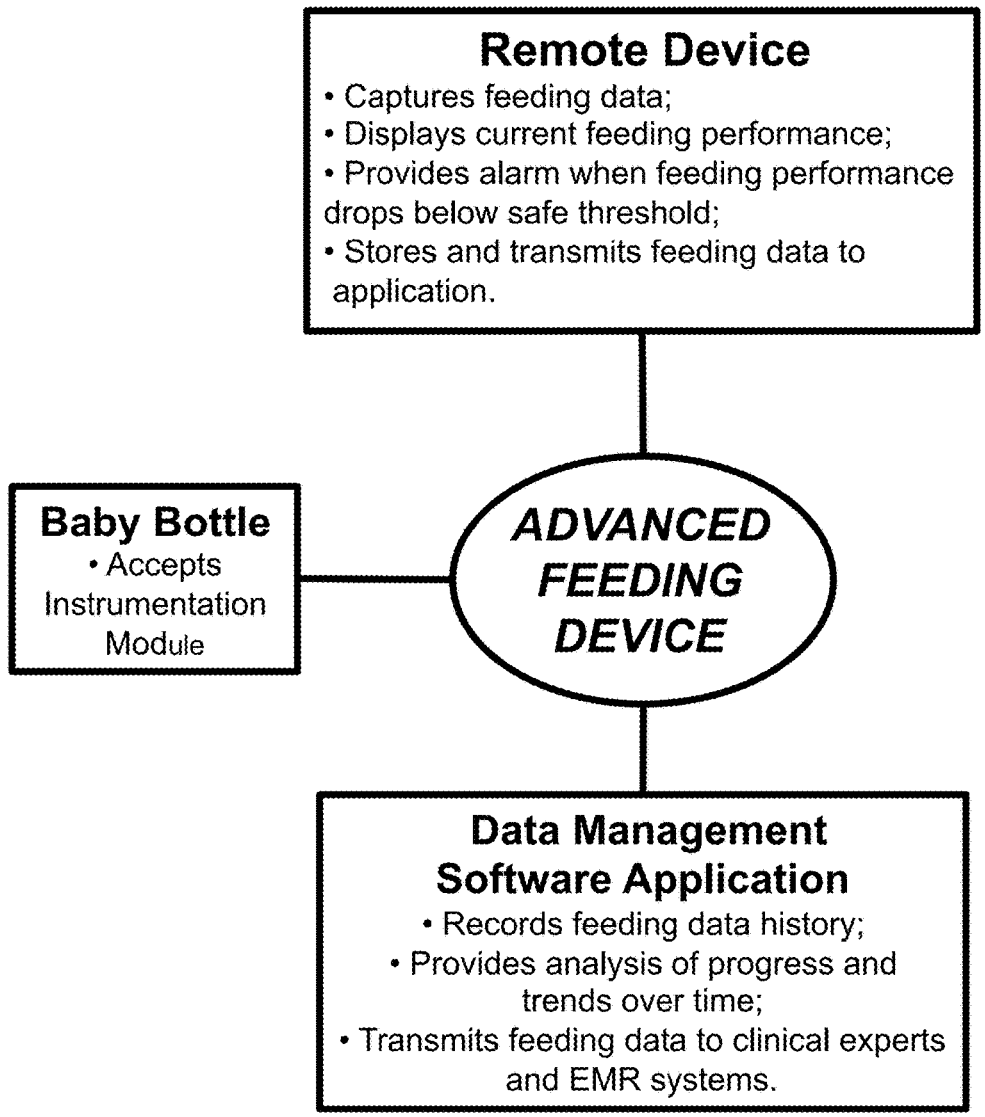

FIG. 24 shows a chart detailing the components of an Advanced Feeding Device, according to the present invention.

Figure 25:
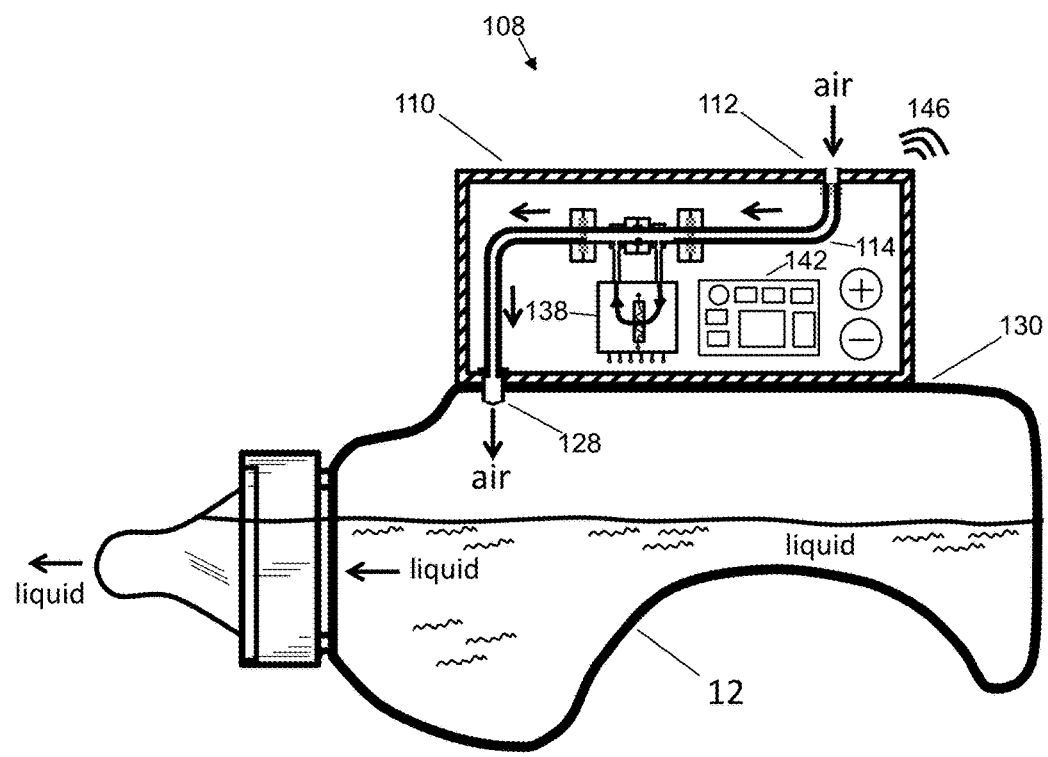

FIG. 25 shows a side cross-section view of an example of a flow rate sensor disposed inside of an instrumentation module that is mounted to the outside of the bottle, on the bottle's side.

Figure 26:
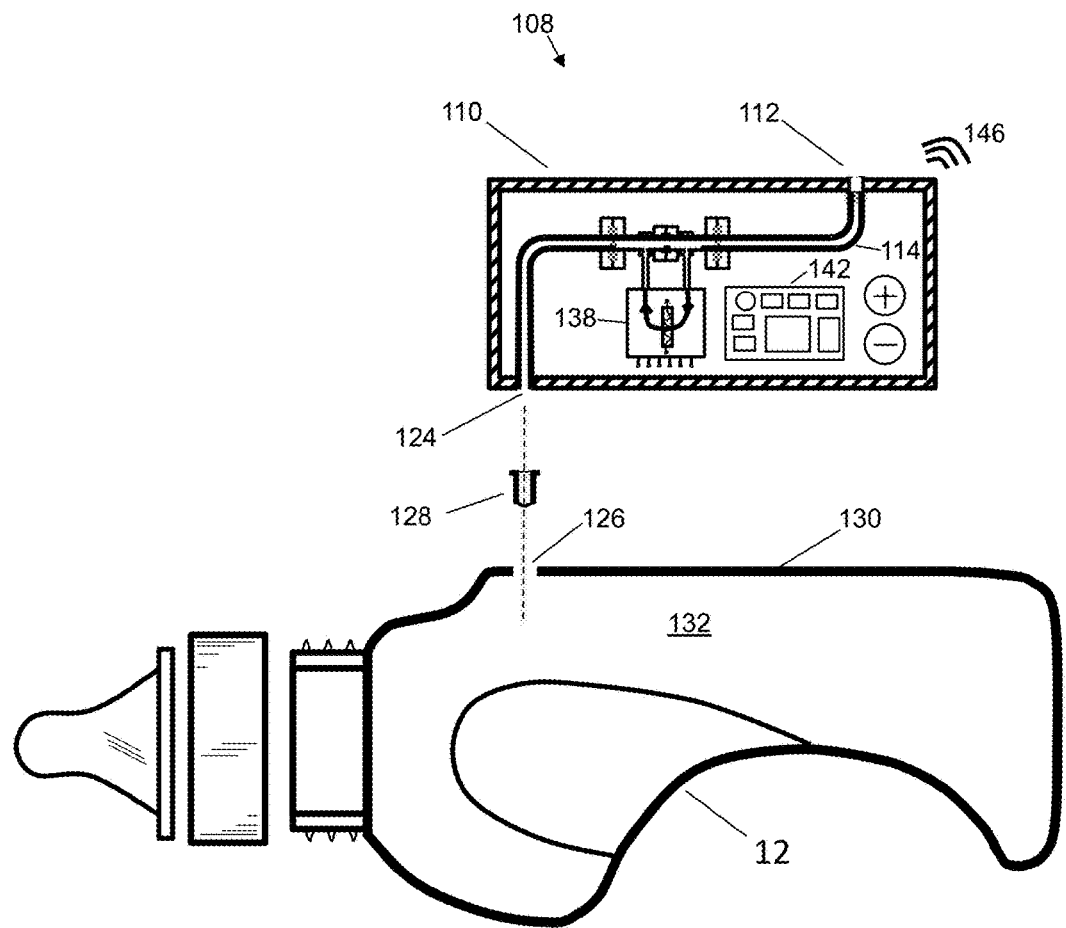

FIG. 26 shows an exploded side cross-section view of an example of a flow rate sensor disposed inside of an instrumentation module that is mounted to the outside of the bottle, on the bottle's side.

Figure 27:
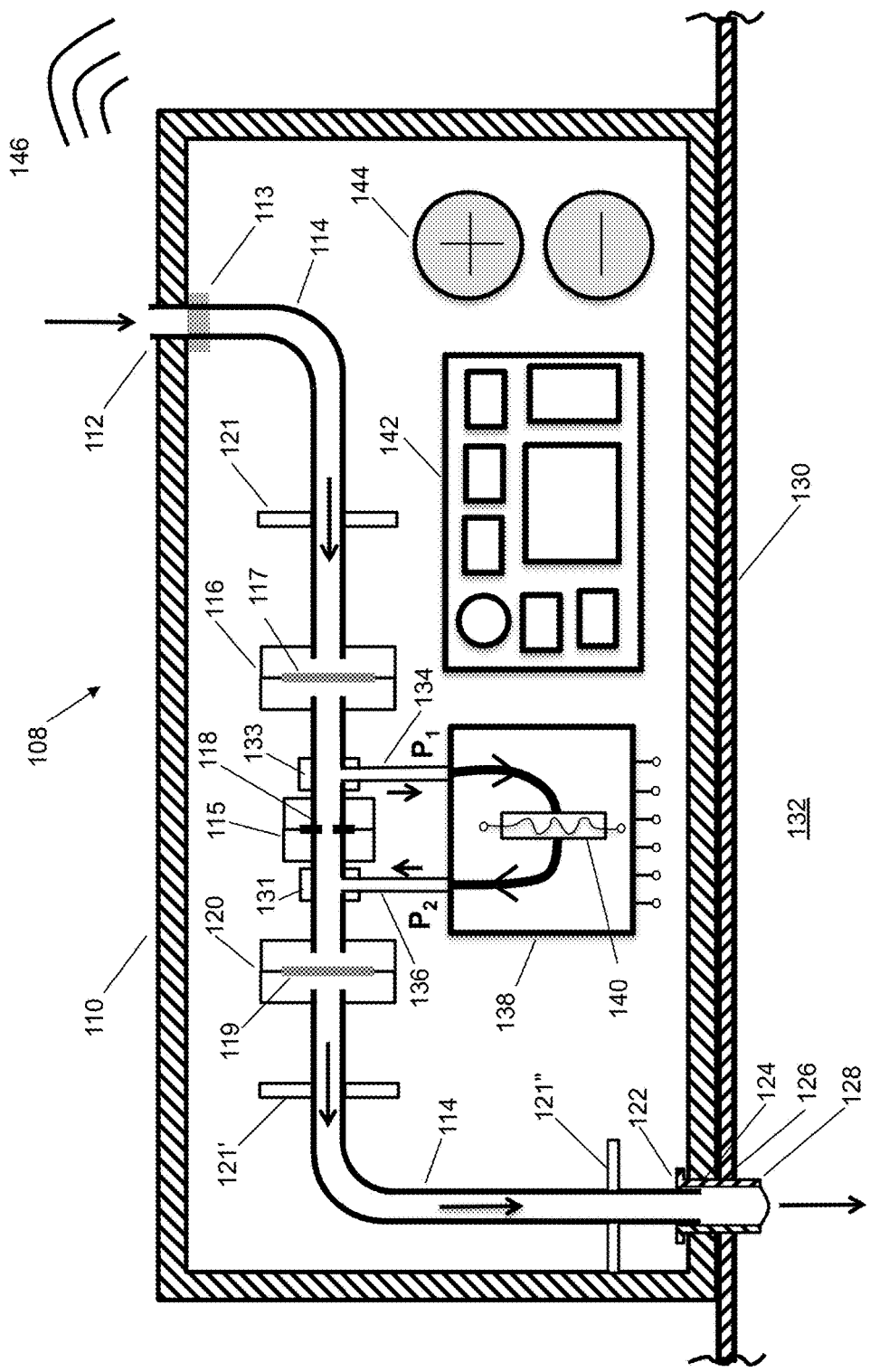

FIG. 27 shows a side cross-section view of an example of a flow rate sensor disposed inside of an instrumentation module that is mounted to the outside of the bottle, on the bottle's side.

Figure 28:
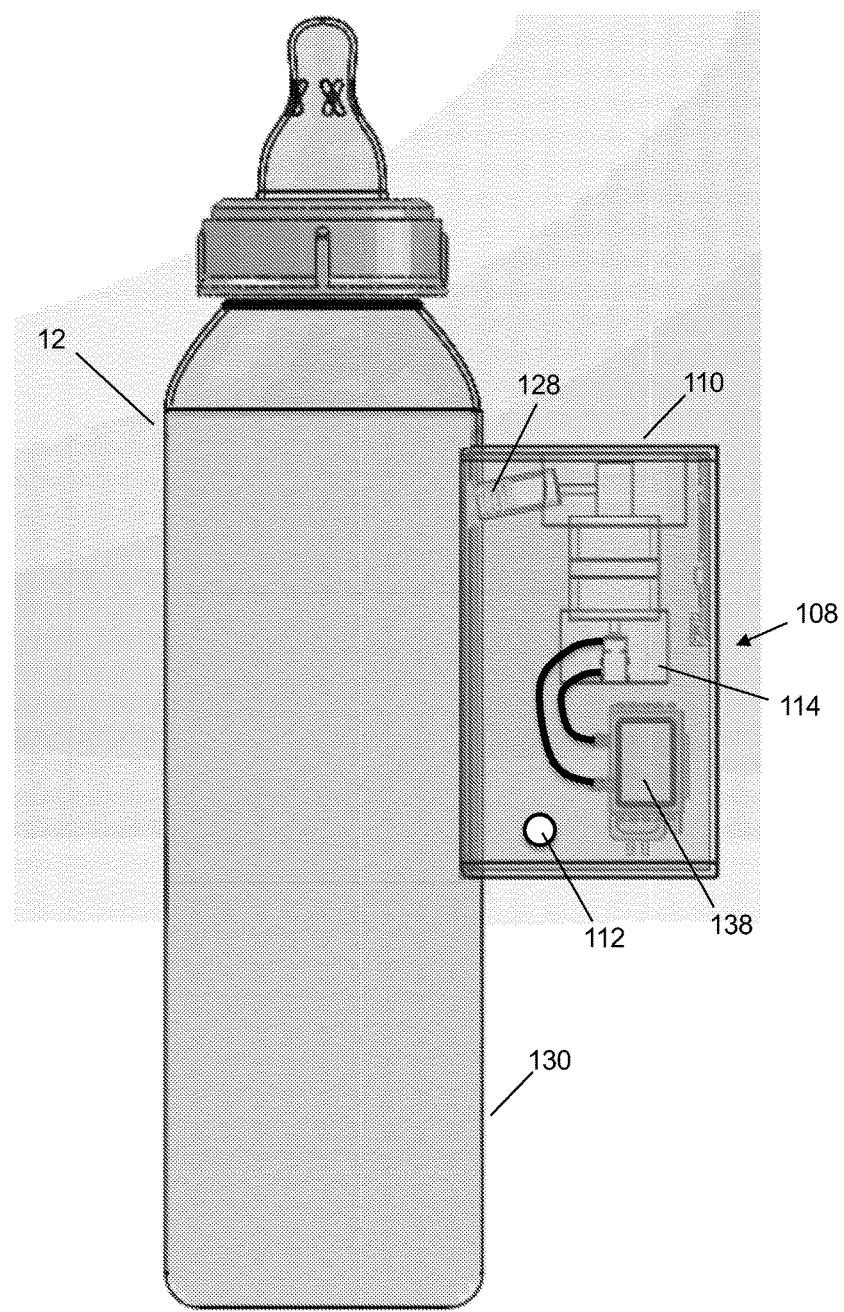

FIG. 28 shows an elevation view of another example of a flow rate sensor disposed inside of an instrumentation module that is mounted to the outside of a feeding bottle, on the bottle's side.

Figure 29:
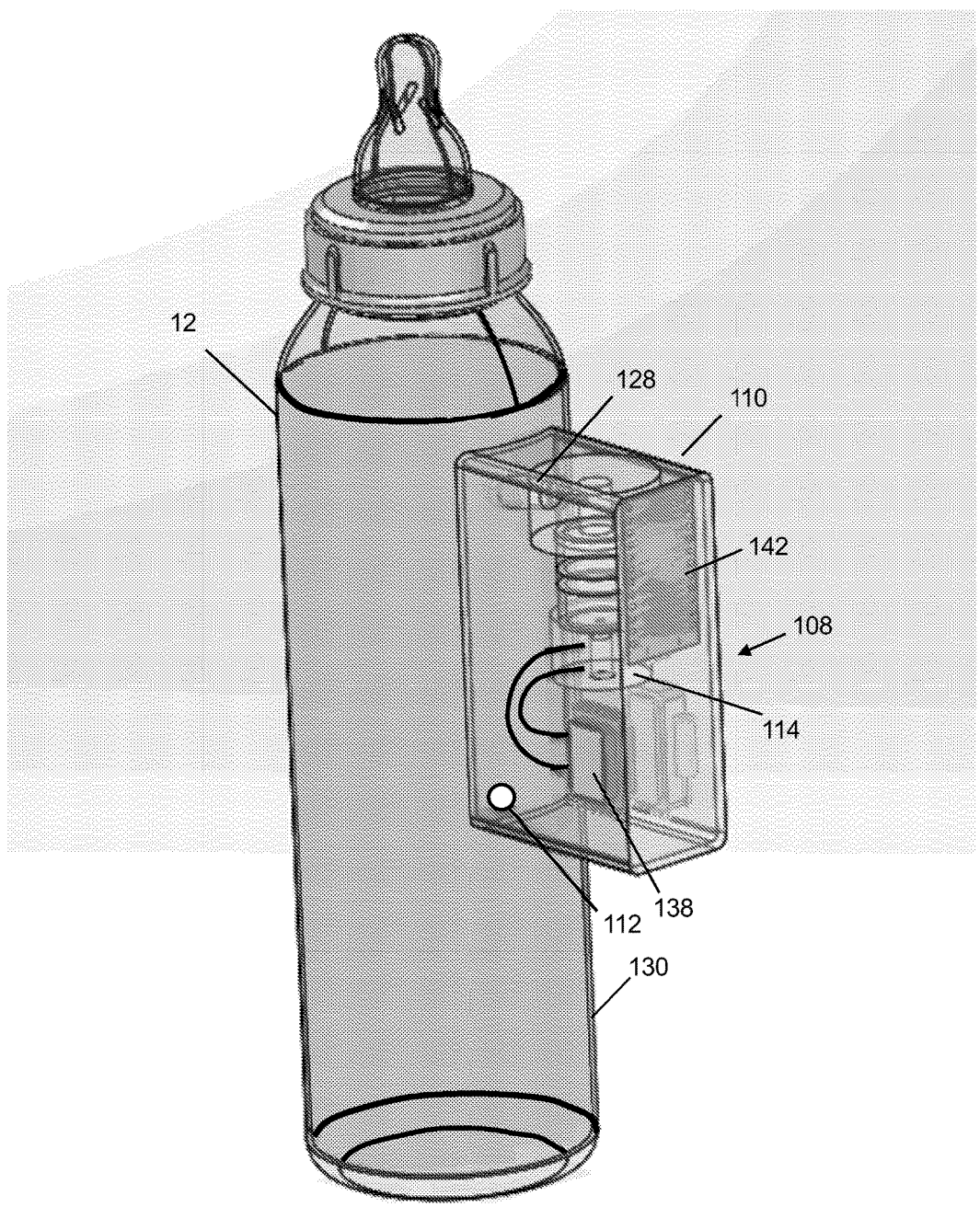

FIG. 29 shows an isometric view of another example of a flow rate sensor disposed inside of an instrumentation module that is mounted to the outside of a feeding bottle, on the bottle's side.

Figure 30:
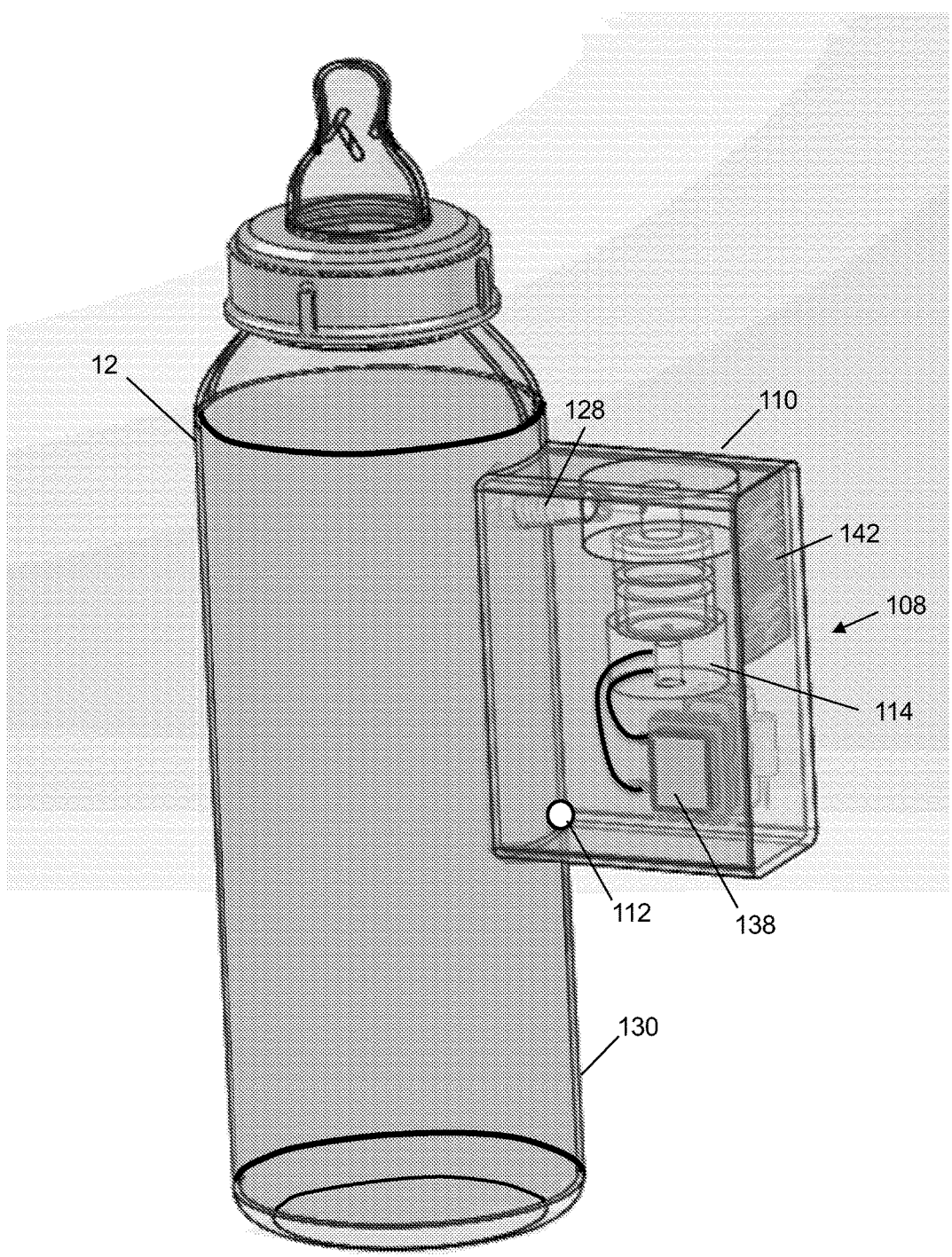

FIG. 30 shows an isometric view of another example of a flow rate sensor disposed inside of an instrumentation module that is mounted to the outside of a feeding bottle, on the bottle's side.

Figure 31:
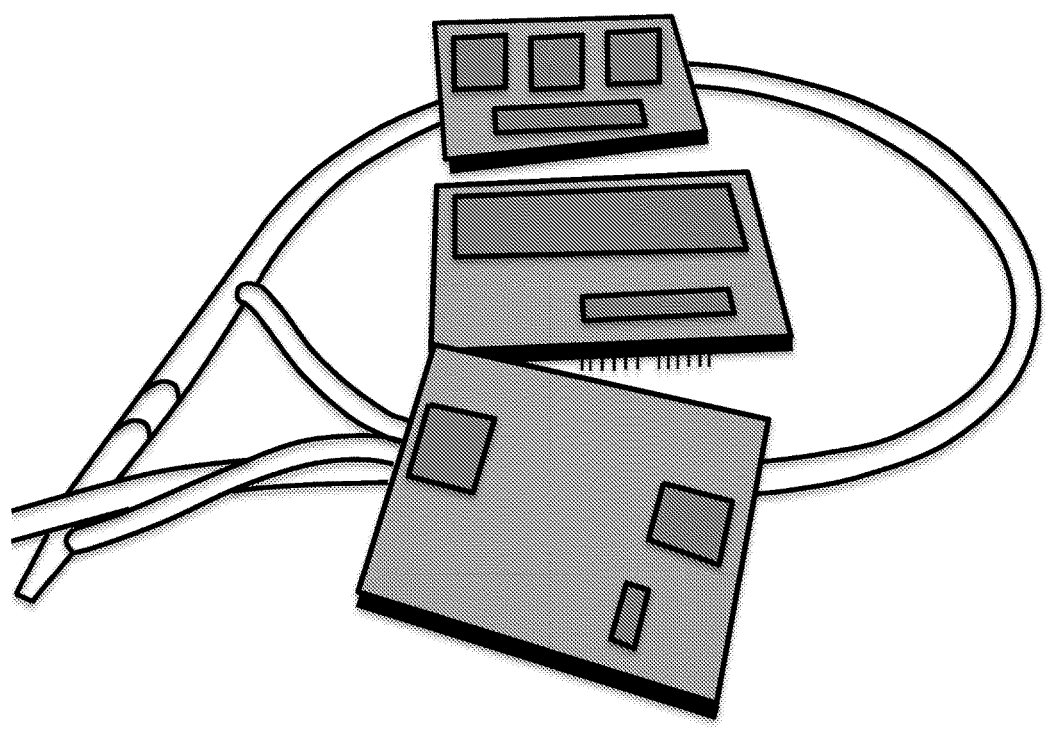

FIG. 31 shows a photograph of a disassembled prototype air flow rate sensing module and associated tubing.

Figure 32:
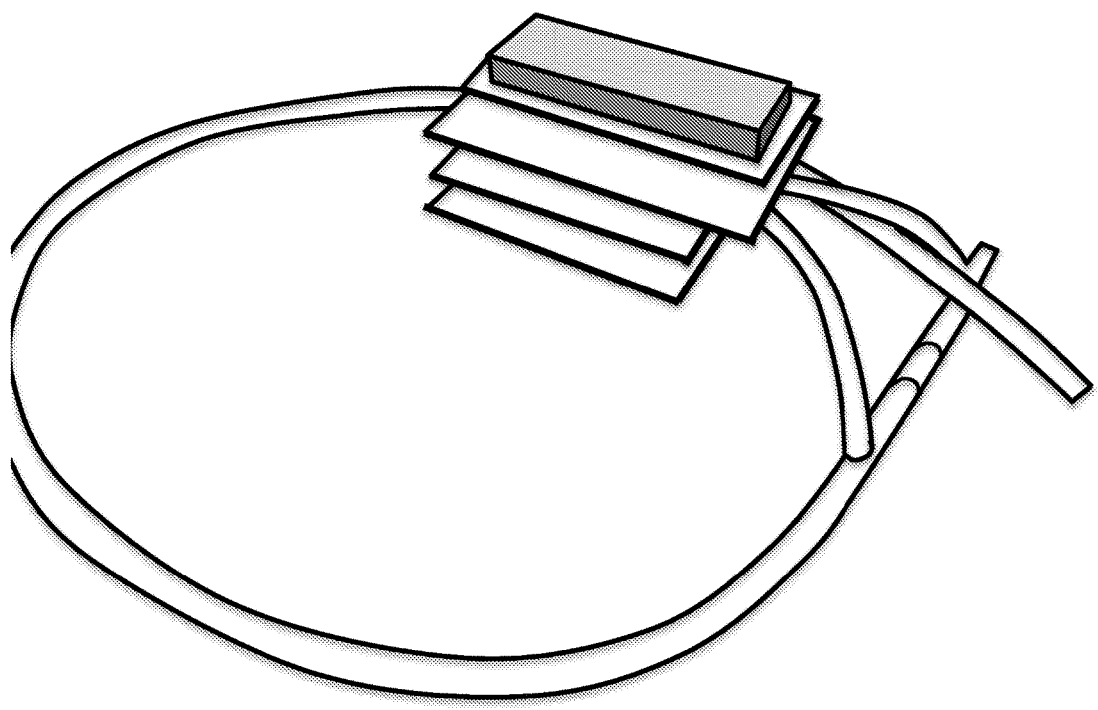

FIG. 32 shows a photograph of an assembled prototype air flow rate sensing module and associated air flow tubing.

Figure 33:
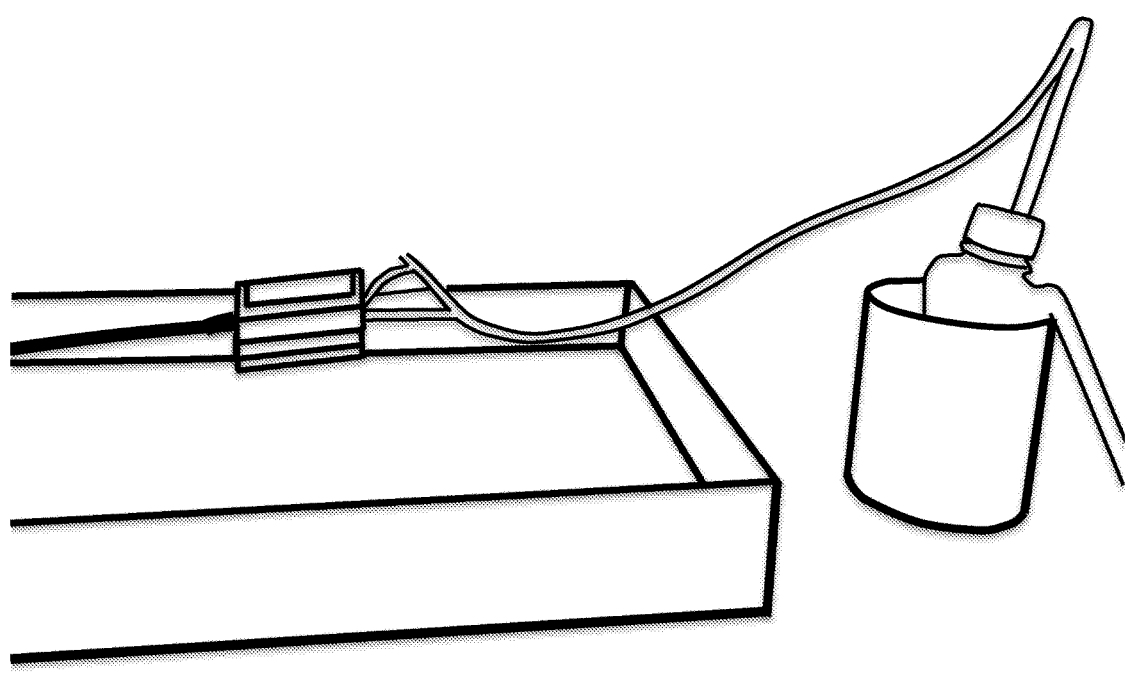

FIG. 33 shows a photograph of an assembled prototype air flow rate sensing module and associated air flow tubing connected to the upper inlet of a water bottle.

Figure 34:
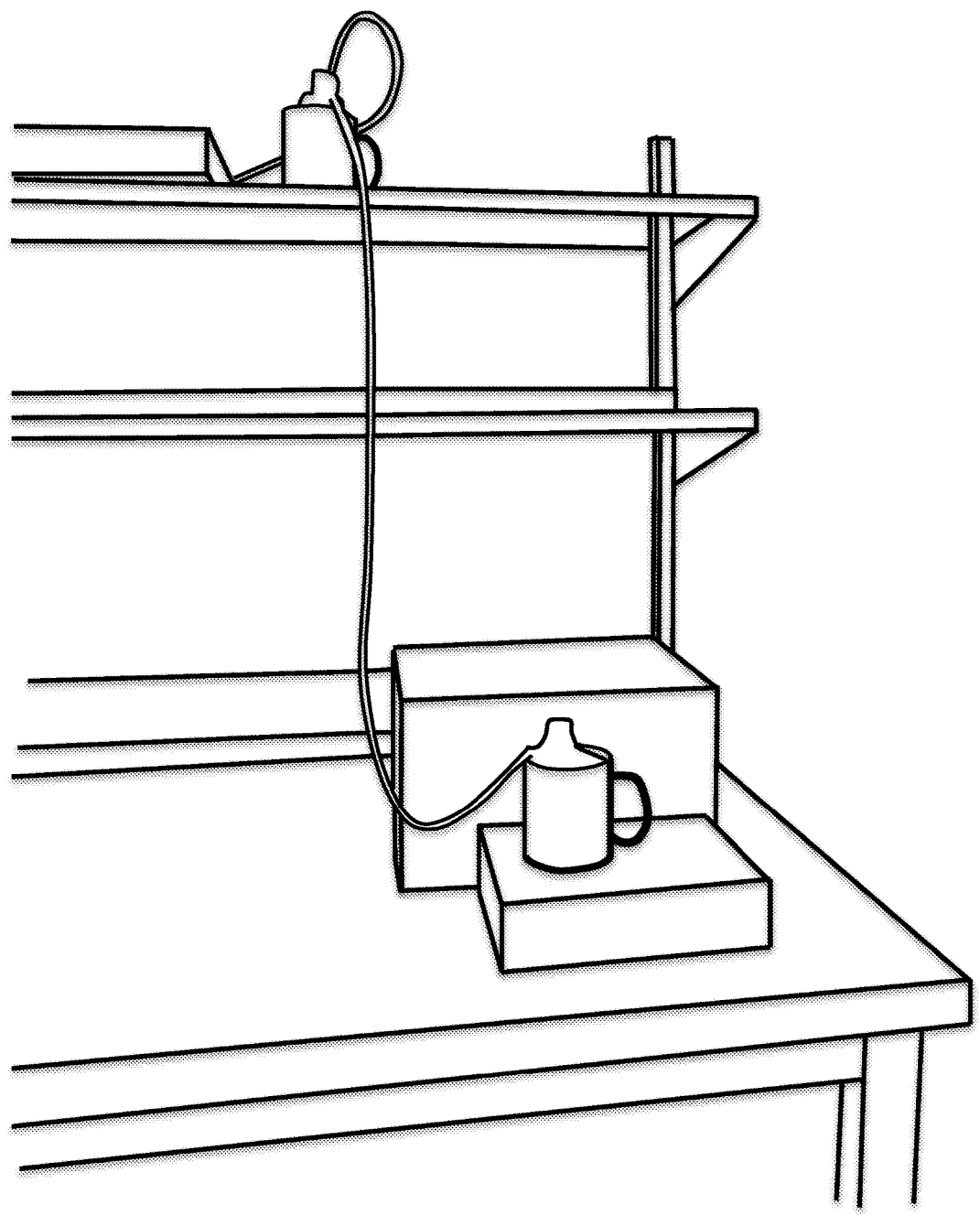

FIG. 34 shows a photograph of an assembled prototype air flow rate sensing module and associated air flow tubing connected to the upper inlet of a water bottle, with a siphon attached to the water bottle for draining water out of the upper bottle down into a lower bottle.

Figure 35:
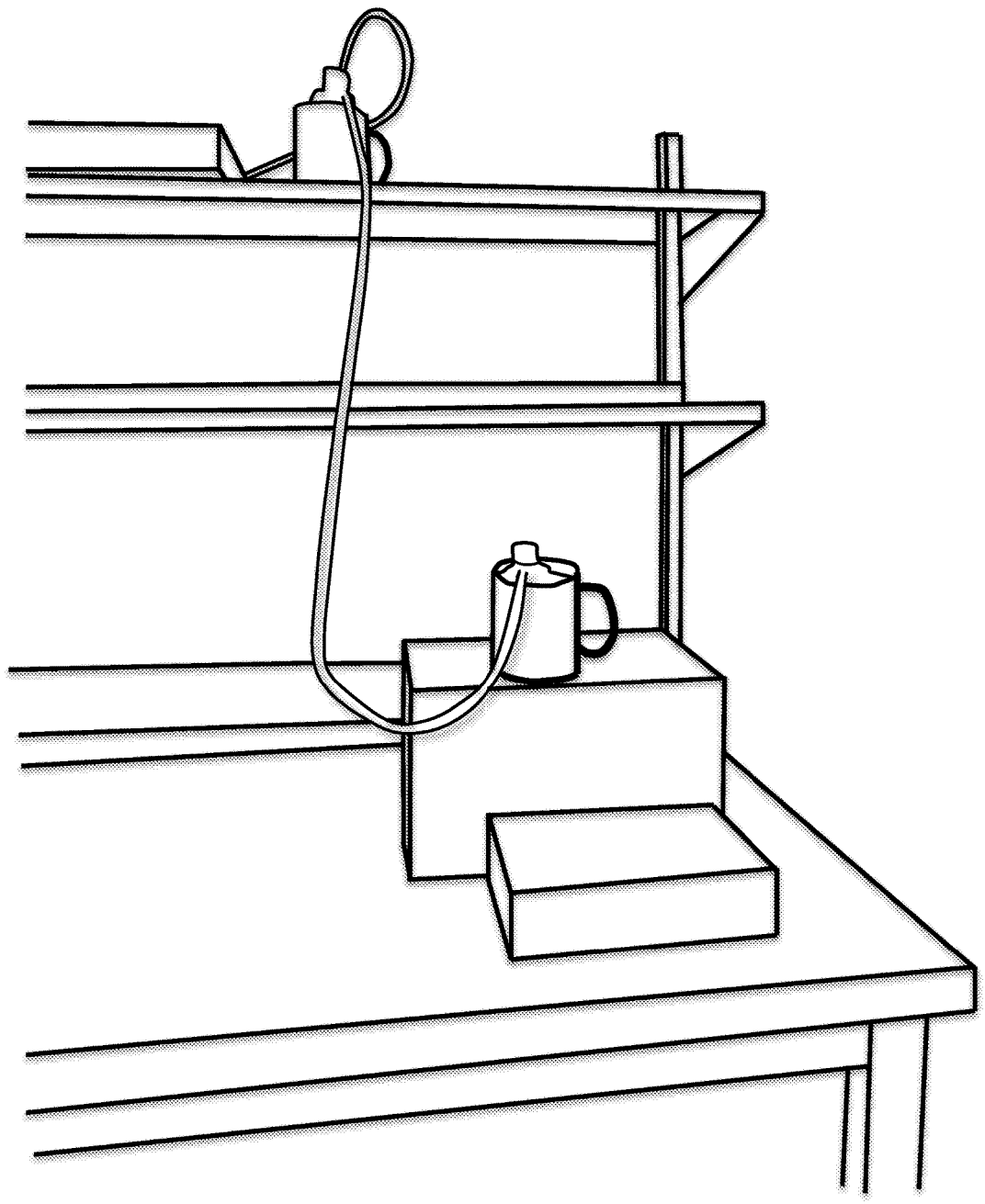

FIG. 35 shows a photograph of an assembled prototype air flow rate sensing module and associated air flow tubing connected to the upper inlet of a water bottle, with a siphon attached to the water bottle for draining water out of the upper bottle down into a lower bottle, with the lower bottle placed at a different height.

Figure 36:
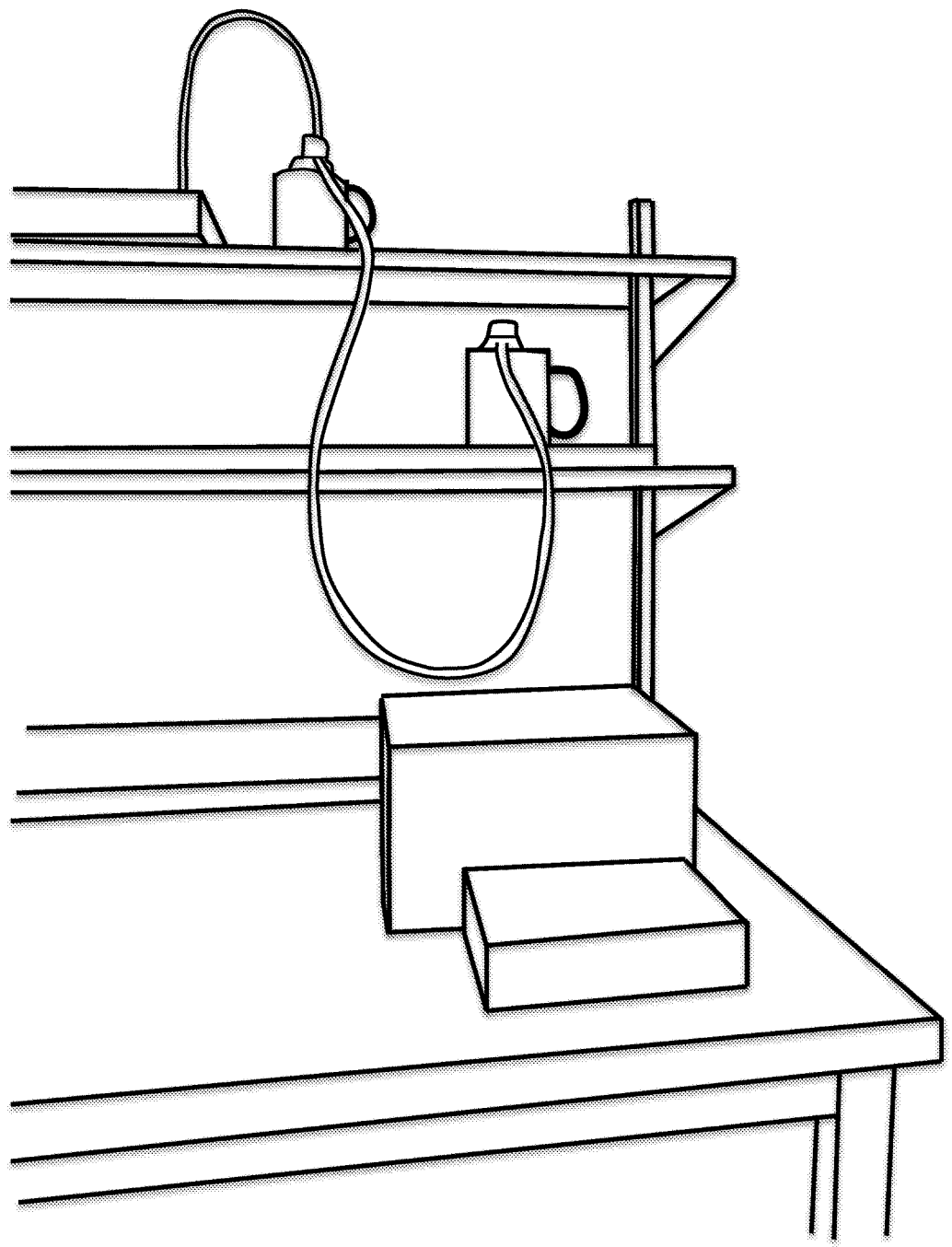

FIG. 36 shows a photograph of an assembled prototype air flow rate sensing module and associated air flow tubing connected to the upper inlet of a water bottle, with a siphon attached to the water bottle for draining water out of the upper bottle down into a lower bottle, with the lower bottle placed at a different height.

Figure 37:
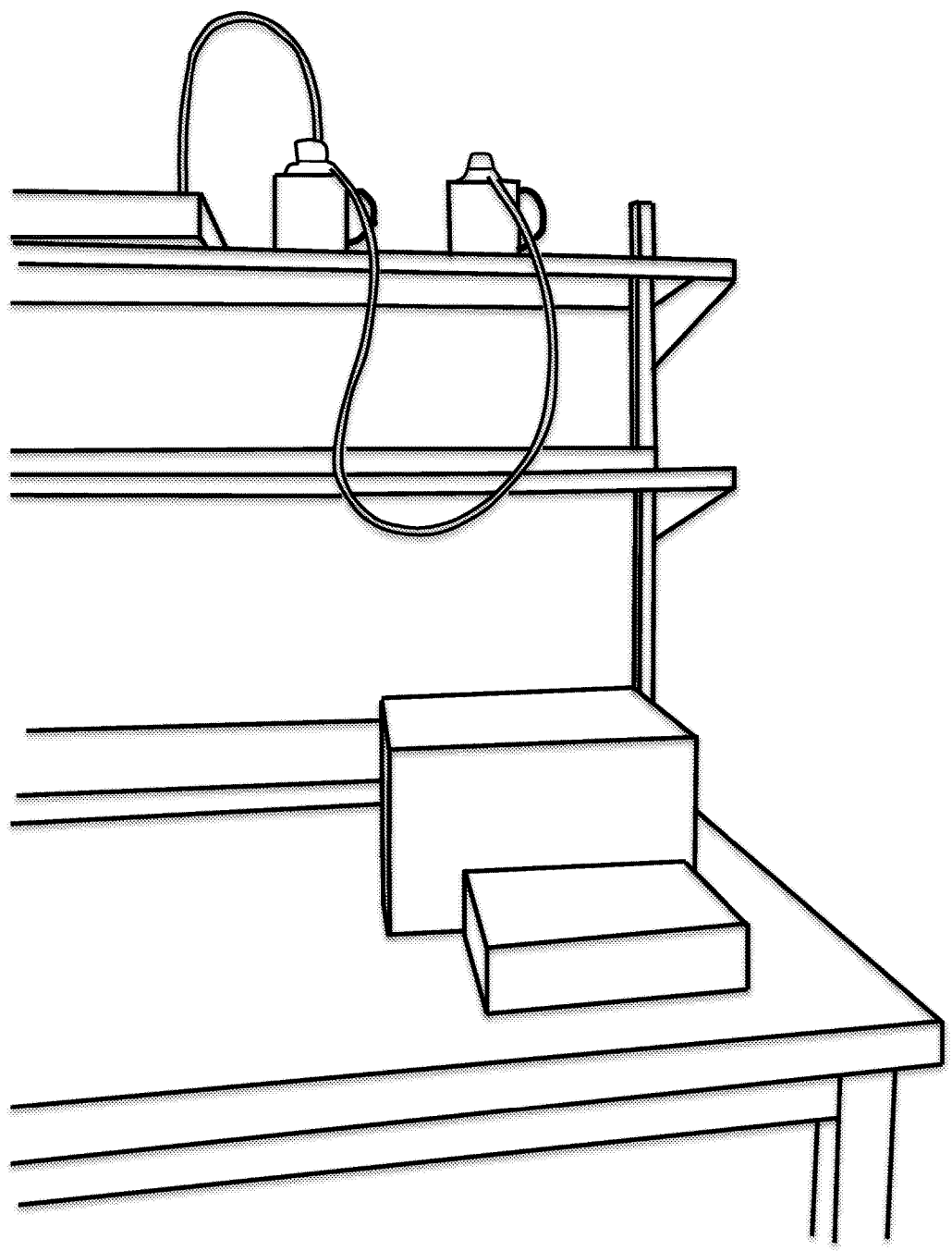

FIG. 37 shows a photograph of an assembled prototype air flow rate sensing module and associated air flow tubing connected to the upper inlet of a water bottle, with a siphon attached to the water bottle for draining water out of the upper bottle down into a lower bottle, with the lower bottle placed at a different height.

Figure 38:
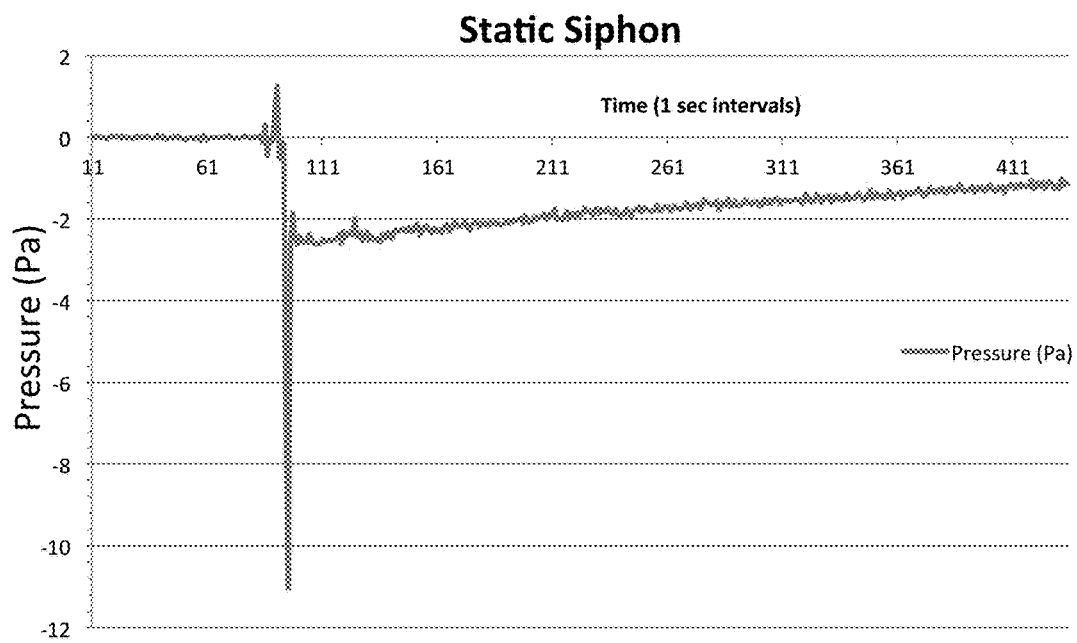

FIG. 38 shows a plot of measured differential pressure (Pa) across the airflow sensor versus time (s) for a static siphon.

Figure 39:
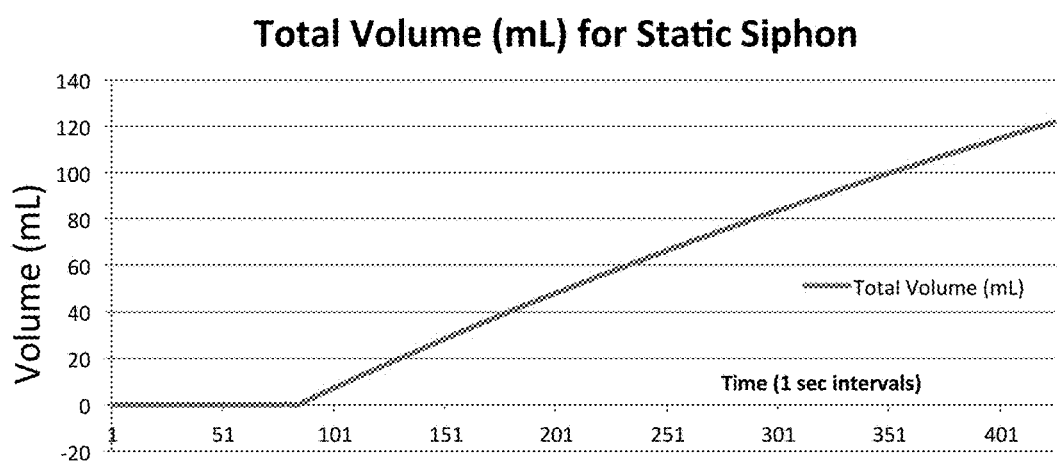

FIG. 39 shows a plot of measured total volume (mL) versus time (s) for a static siphon.

Figure 40:
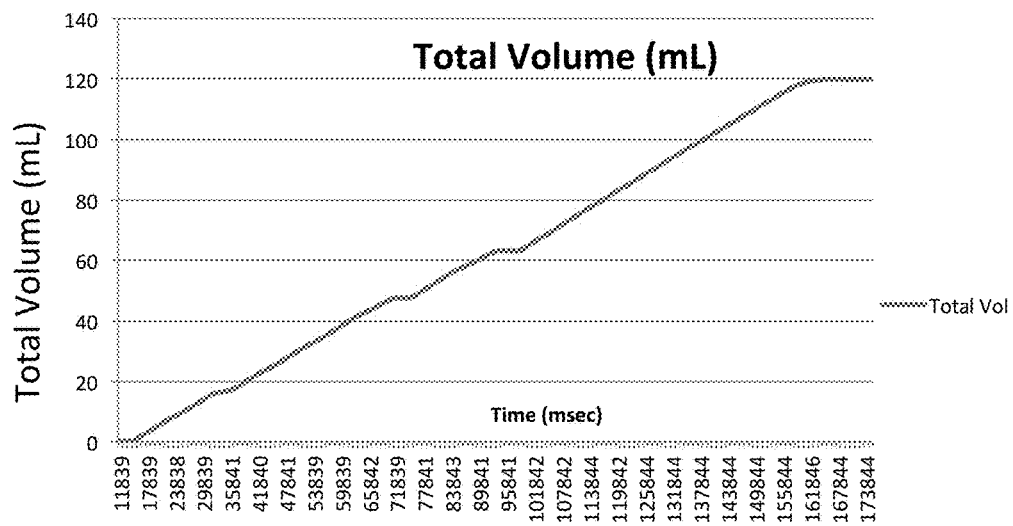

FIG. 40 shows a plot of measured total volume (mL) versus time (msec) for a transient siphon with step changes in height, illustrating the range of dynamic response.

Figure 41:
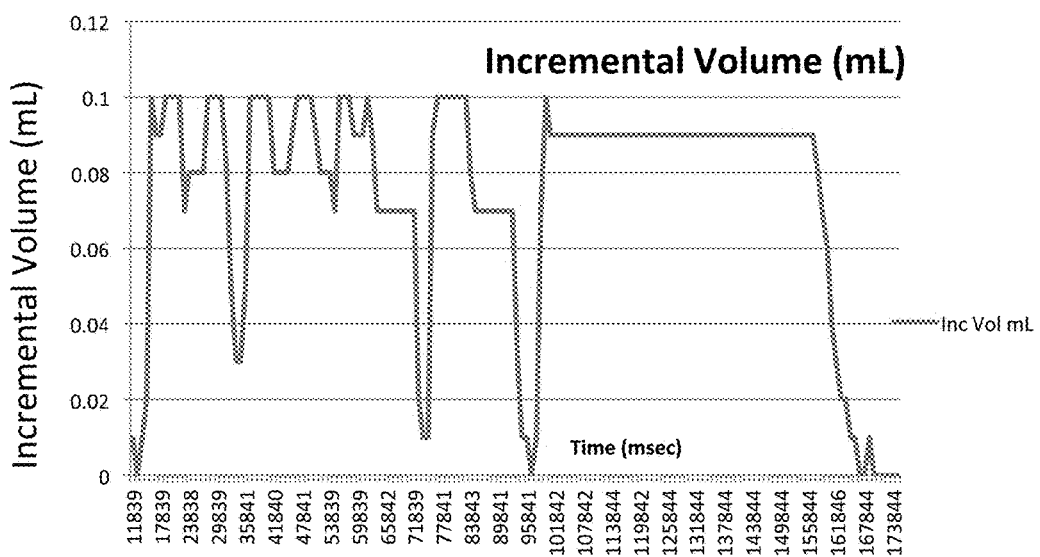

FIG. 41 shows a plot of measured incremental volume (mL) versus time (msec) for a transient siphon with step changes in height, illustrating the range of dynamic response.

Figure 42:
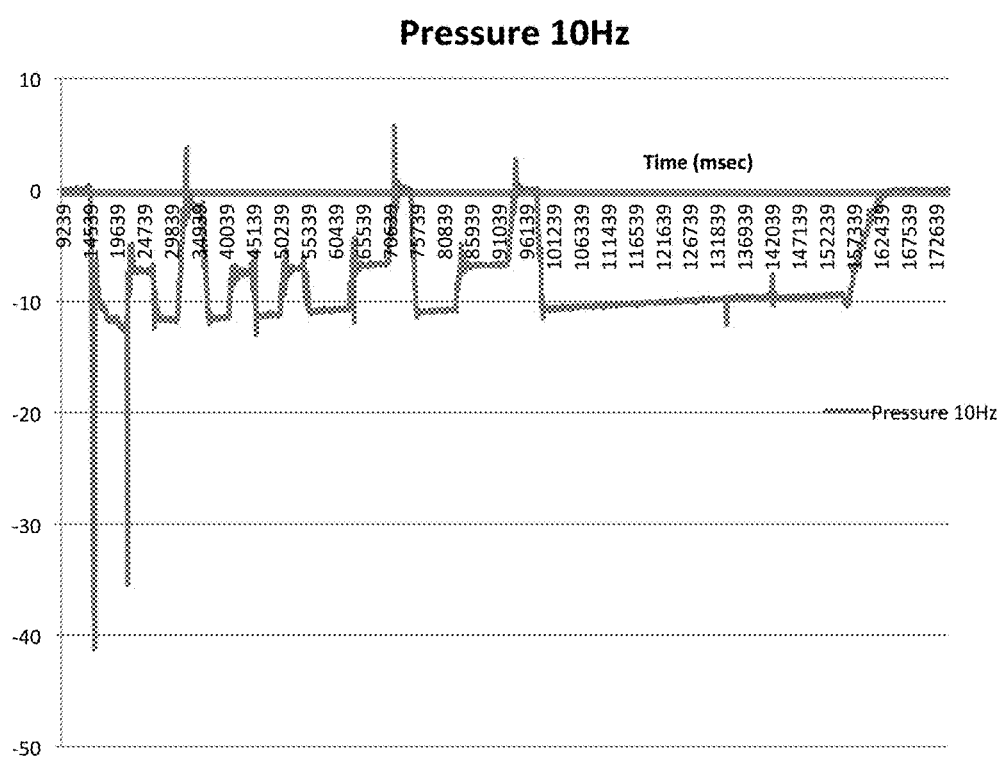

FIG. 42 shows a plot of measured pressure (Pa) versus time (msec) for a transient siphon with step changes in height, illustrating the range of dynamic response.

Figure 43:
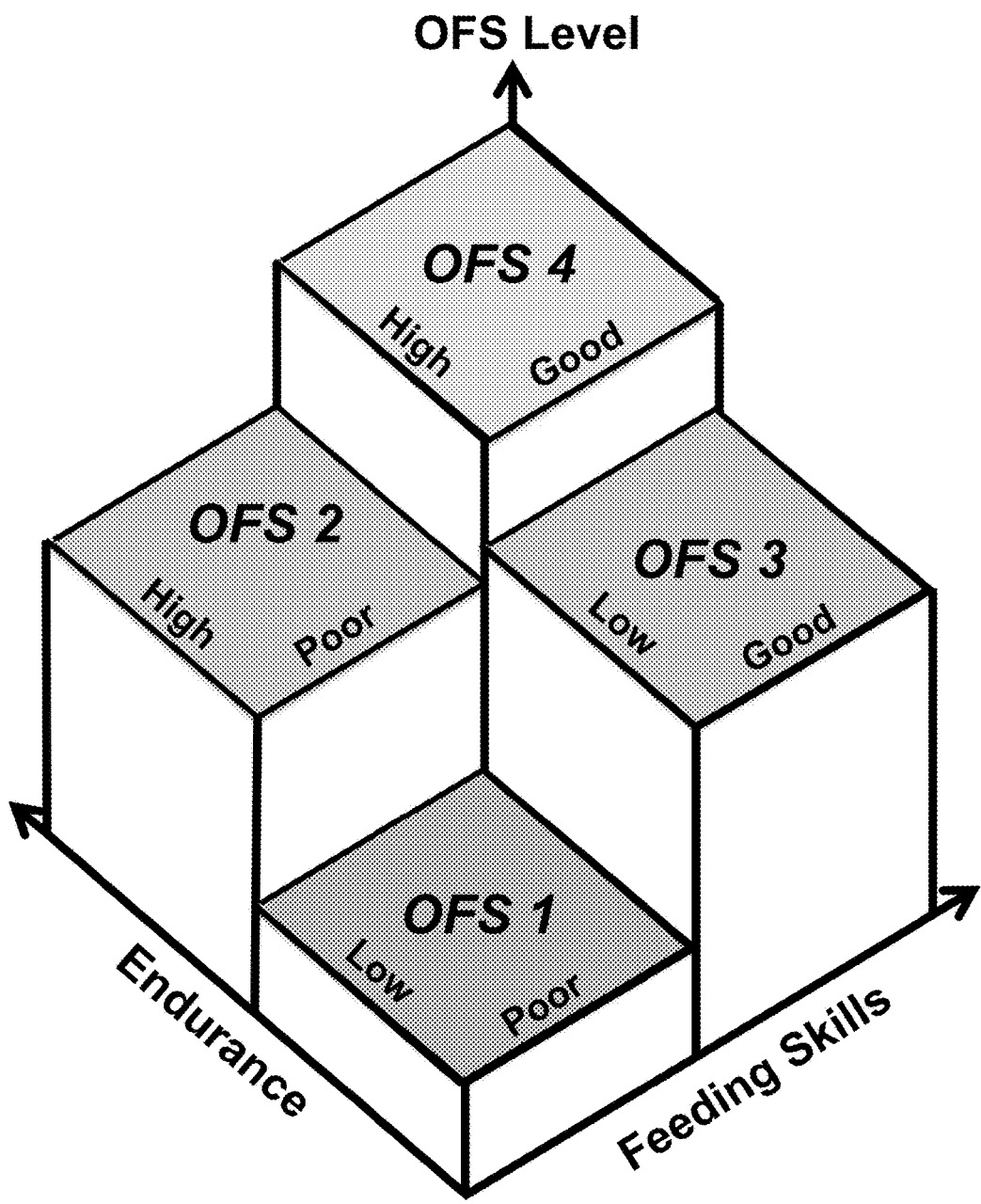

FIG. 43 shows a 3-D map of an example of the partitioning of four oral feeding skill (OFS) levels 1-4 according to a pair of performance parameters: (1) endurance and (2) feeding skills

DETAILED DESCRIPTION OF THE INVENTION

FIGS. 1-43 show examples of various embodiments of the present invention. Note: the term "smart device" or "remote device" refers to any type of wireless or wired smart phone (e.g., iPhone®), smart tablet (e.g. iPad®), laptop, personal computer (PC), or desktop data processing device, such as a Biopac® data collection unit, using a wireless protocol such as Bluetooth®.

Note: Infants may be categorized by their gestational age (GA) or birth weight. Preterm infants are born ≤36 weeks gestational age (GA) and differentiate between extremely preterm (<28 weeks), very preterm (28 to <32 weeks), moderate preterm (32-33 weeks), late preterm (34 to 36 weeks). Full-term infants range between 37 to 42 weeks gestation. By weight, extremely low birth weight infants are born <1000 g, very low birth weight between 1000 g to <1500 g, low birth weight between 1500 g and <2500 g, full term between 2500 and 4200 g.

Infant birth weight (Kg) generally increases with gestational age (weeks), as shown in FIG. 23.

Figure 1:
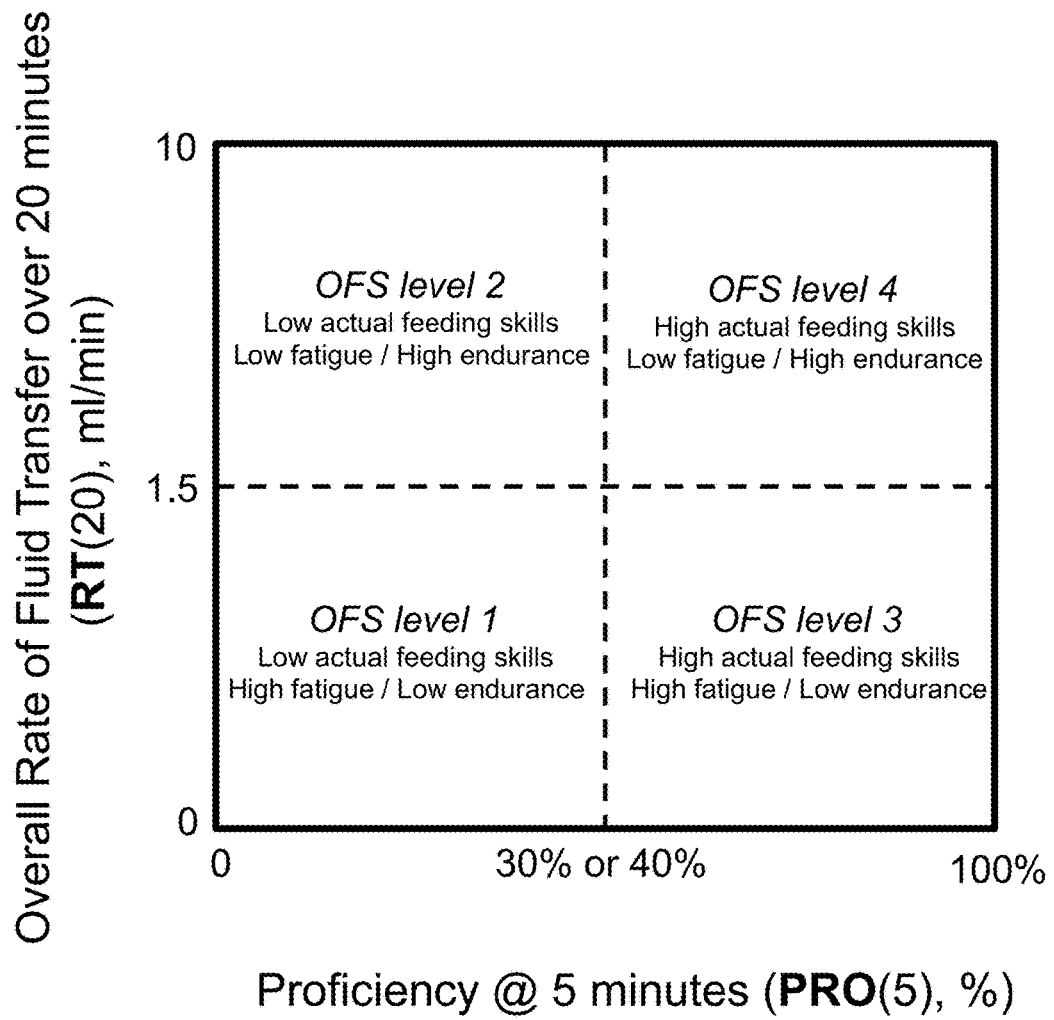

FIG. 1 shows a map of an example of the partitioning of oral feeding skill (OFS) into 4 distinct levels: 1, 2, 3, 4 according to a pair of performance parameters: (1) proficiency ($PRO_5$) and (2) rate of milk transfer ($RT_{20}$). The $PRO_5$ cutoff is defined as the % volume (ml) taken during the first 5 min, i.e., V(5), divided by the total volume (ml) of liquid prescribed, $V_{prescribed}$. $RT_{20}$ is defined as the overall rate of milk transfer (ml/min) averaged over an entire 20-minute feeding session. In this example, which applies to premature infants [Lau, 23], the cutoff (i.e., threshold), $PRO_5$, between 'poor' and 'good' skills is set at $PRO_5$=30% or 40%, depending on whether infants are ≤33 weeks or ≥34 weeks gestation, respectively; and the cutoff, $RT_{20}$, between 'poor' and 'good' endurance is set at $RT_{20}$=1.5 ml/min for gestational ages of 25-36 weeks; $RT_{20}$=3.0 ml/min for gestational ages of 37-42 weeks.

The proficiency parameter ($PRO_5$), which is measured within the first 5 minutes of feeding, is taken as an indirect marker for a baby's inherent oral feeding skills when fatigue is minimal (~0). On the other hand, the overall rate of transfer ($RT_{20}$, ml/min), which is averaged over an entire feeding session, is taken as an indirect marker for an infant's average oral feeding skills when fatigue comes into play. Note: the feeding duration is typically limited to a maximum of no more than 20 minutes for premature infants. For strong feeders (near-term and term babies), however, the feeding time can be as short as 5-10 minutes. Note: The OFS scale can be divided into any different number of levels, e.g., 1, 2, 3, 4, 5, or 6 levels, with appropriate cutoff (threshold) values defining and differentiating the different levels of infants' prematurity.

Figure 2:
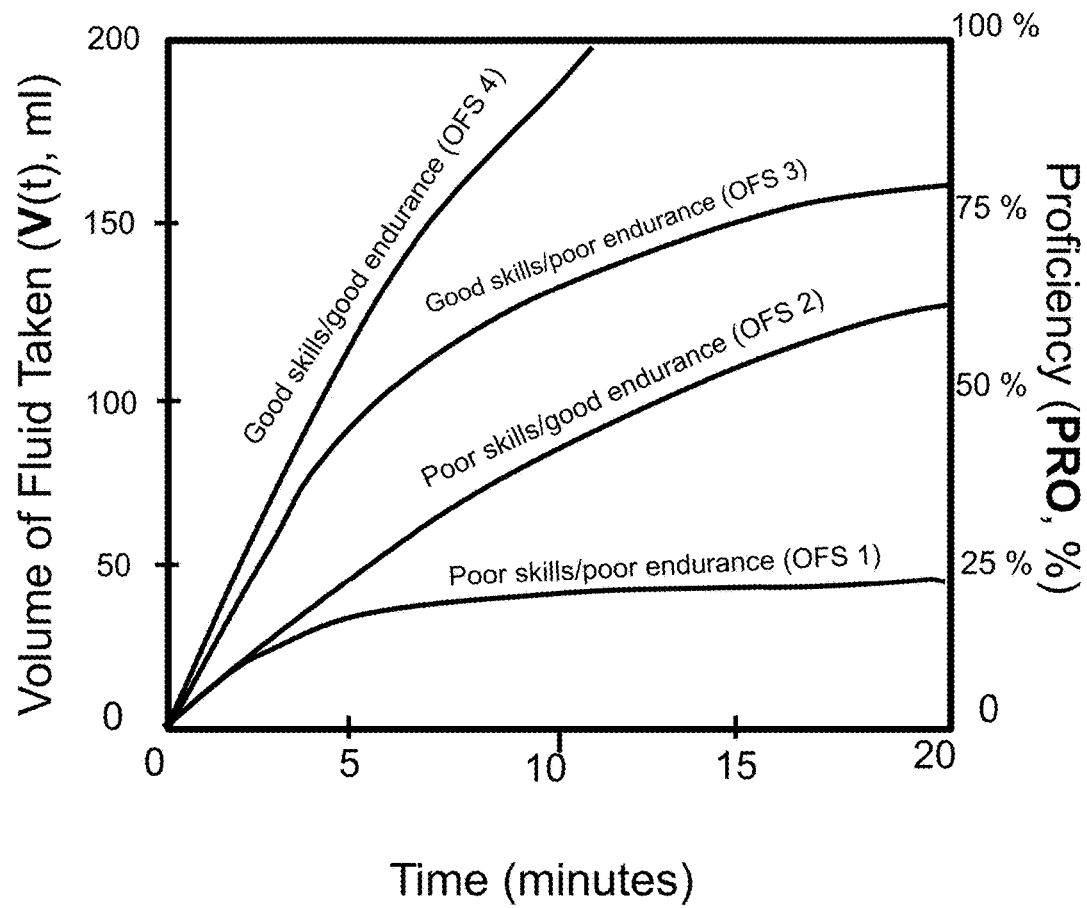
FIG. 2 shows a schematic plot of volume of liquid taken (V(t), ml) and proficiency (PRO, %) versus time (minutes), with four examples indicating the four different OFS performance levels.

FIG. 2 shows a schematic plot of volume of liquid taken (V(t); ml) versus time (minutes), with four examples indicating the four different OFS performance levels: 1, 2, 3, 4. Infants with poor endurance generally transfer (ingest), on average, less than 25% of their prescribed volume, while infants with good endurance generally transfer greater than 60% of the prescribed volume, at the end of a feeding session. Infants with good skills and good endurance generally transfer greater than 90% of the prescribed volume in a session.

Figure 3:
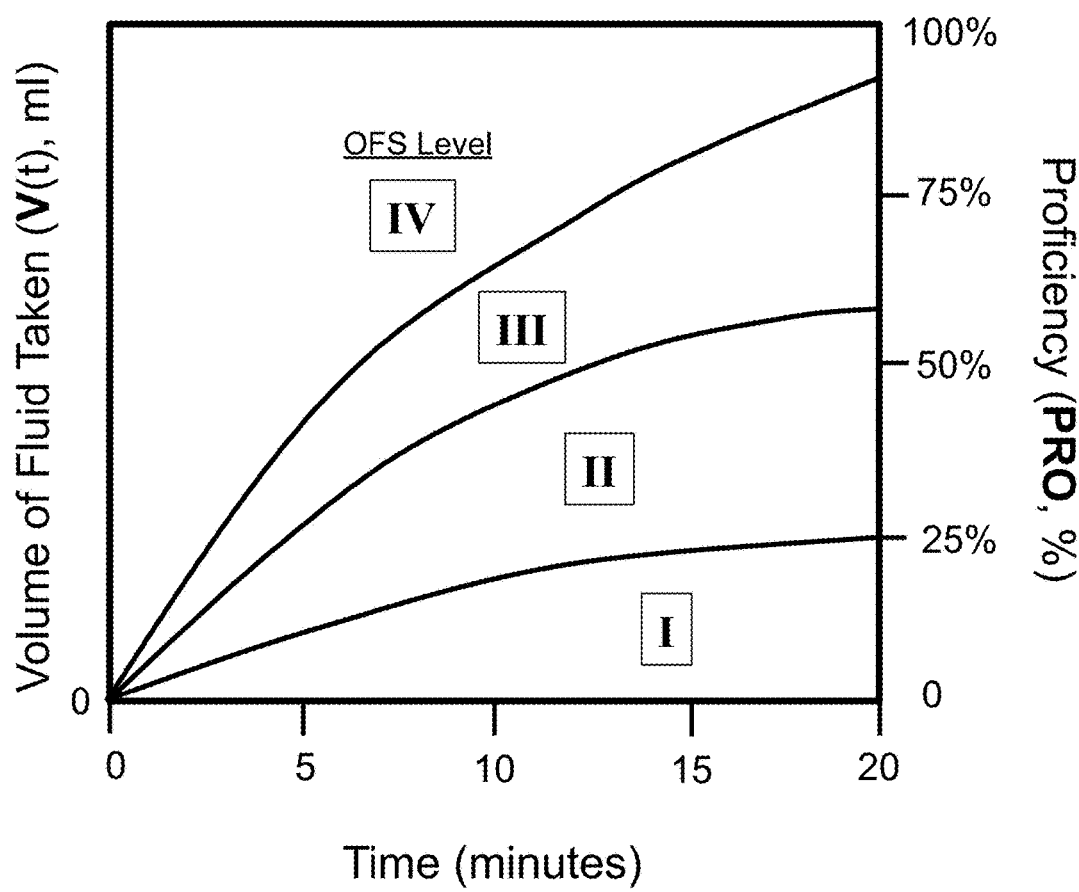
FIG. 3 shows a schematic plot of volume of liquid taken (V(t), (ml) and proficiency (PRO, %) versus time (minutes), for four different examples that illustrate the four different OFS levels.

FIG. 3 shows a schematic plot of volume of liquid taken (V(t); ml) versus time (minutes), also known as "Proficiency" (PRO) in % when normalized to the volume prescribed, $V_{prescribed}$, for four different examples that illustrate the four different OFS levels. The proficiency, in general, can be measured (1) at discrete intervals (e.g., every 5 minutes, or every 1-2 minutes) by weighing the bottle and subtracting the weight from an initial weight and then converting the weight change to a volume change by the liquid's density; or (2) continuously by using an in-situ volume-measuring or weight-measuring sensor disposed inside of, or outside of, the feeding bottle that continuously measures the volume or weight remaining (and subtracting from the initial volume or weight).

Alternatively, the instantaneous volume taken, V(t), can be calculated from measurements of the flow rate (ml/min) by taking the integral of an instantaneous flow rate, FR(t), times a time increment (dt), over a time period from $t=t_1$ to $t=t_2$, according to eq. (1), as follows:

$$V(t) = \text{INTEGRAL}_{[t=t1 \text{ to } t2]}\{FR(t) \cdot dt\}(ml) \quad (1A)$$

The time period $t_1$ to $t_2$ can be as short as a single suck (e.g., 1 second), in which case the integrated volume equals the bolus volume taken for a single suck, or it can be as long as 20 minutes, in which case the integrated volume equal the total volume taken during a feeding session. The instantaneous flow rate, FR(t), is equal to the time derivative of the volume taken, V(t), as follows:

$$FR(t)=dV(t)/dt \text{(ml/min)} \quad (1B)$$

Note, when the experimental data fall below the bottom line in FIG. 3, the OFS level is equal to 1 and the caregiver should stop feeding because of the low rate of milk transfer (OT less than 25% after the maximum allowed period of 20 minutes). Infants with poor skills typically transfer less than 30% of the volume prescribed after 5 minutes, while infants with good skills typically transfer more than 50% of the volume prescribed after 5 minutes. Infants with good skills and good endurance (OFS level 4) can complete a typical feeding in less than 20 minutes (e.g., around 10 minutes, with an Overall Transfer, OT=100%). At the opposite extreme, infants with poor skills and poor endurance (OFS level 1) typically ingest less than 50% of the total volume prescribed over the maximum allowed 20 minutes (e.g., Overall Transfer, OT=20-30%).

Figure 4:
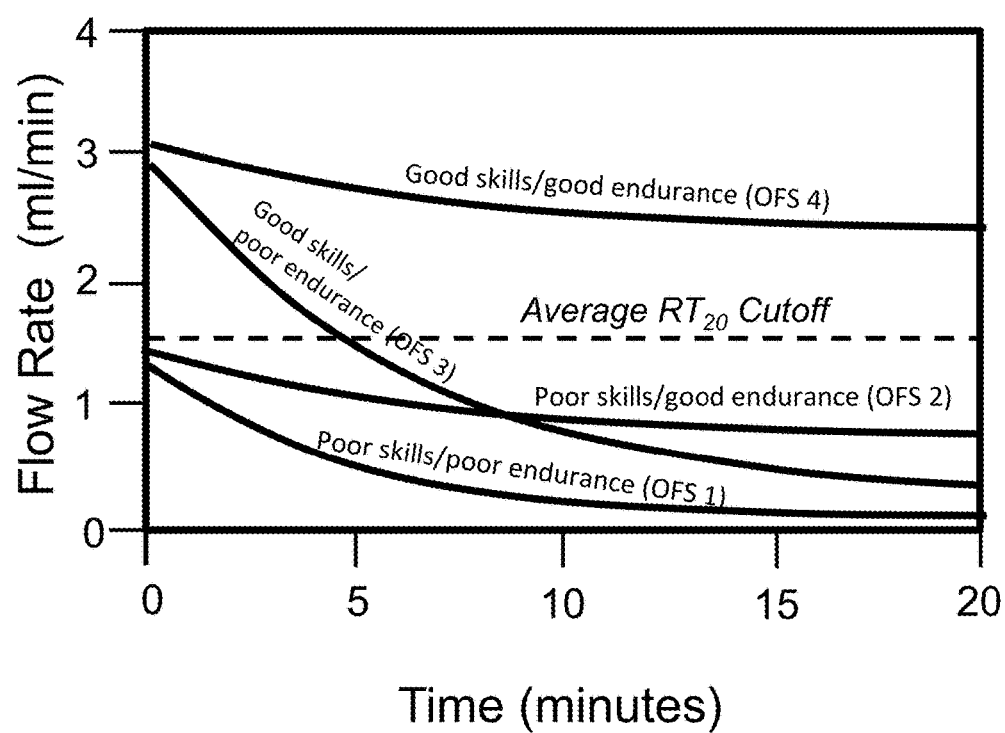
FIG. 4 shows four schematic flow rate profiles of flow rate (ml/min) versus time (minutes) of an infant feeding at four different OFS levels.
Figure 5:
FIG. 5 shows a chart of the recommended nutritional constant, K, in Kcal/Kg/day using 24, 22, and 20 Kcal/oz, respectively for the three individual gestational groups of infants.

FIG. 4 shows a schematic plot of examples of flow rate (ml/min) versus time (minutes) of four different sample flow rate curves. The flow rates naturally declines over time as the infant fatigues and feeding slows down. An average flow rate can be determined in a couple of different ways. It can be calculated by taking the time derivative of the instantaneous curve of volume taken versus time (i.e., FIG. 3). This gives the average flow rate averaged over the period of time corresponding to the period of a single suck. The time derivative can be calculated at discrete intervals (e.g., every 5 minutes, or every 1-2 minutes), or it can be calculated at an essentially continuous rate by using a very small delta-time interval (e.g., 0.1 seconds). The time derivative can be calculated using a variety of approximate formulas, depending on the particular time interval chosen, as is well known in the art, and as is readily available in mathematical functions and statistical programs. The instantaneous flow rate (ml/sec) can also be measured directly in a continuous manner by an in-situ flow rate sensor disposed inside of the feeding bottle (see below). Alternatively, the bottle can be weighed at periodic intervals (e.g., every 5 minutes), and differences taken to get the volume ingested via the liquid's density.

The optimum amount of liquid prescribed to be taken in a single feeding session, $V_{prescribed}$, can optimally be calculated according to an infant's weight, W (kg) using the following nutritional rate constant, K, for premature infants where:

$$K=120 \text{(Kcal/kg/day)} \quad (2)$$

This nutritional rate constant, K, has been selected so that the infant attains an optimum rate of weight gain of about 15 g/Kg/day. Optionally, the nutritional rate constant, K, can range from 100 to 120 Kcal/Kg/day, depending on the infant's gestational age (See FIG. 5). Accordingly, the volume prescribed, $V_{prescribed}$, is given by eq. (3), in terms of Kcal/day.

$$V_{prescribed}(\text{per day})=K \times W \text{(Kcal/day)} \quad (3)$$

Then, assuming a nutritional density of the infant formula as being=0.8 Kcal/ml (which equals 24 Kcal/30 ml or 0.8 Kcal/ml), then eq. (3) can be converted to a daily volumetric intake according to eq. (4):

$$V_{prescribed}(\text{per day})=K \times W/0.8 \text{(ml/day)} \quad (4)$$

Finally, depending on the number of feeding sessions per day, N, the amount of liquid prescribed to be taken in a single feeding session can be calculated by:

$$V_{prescribed}(\text{per session})=1.25 \times K \times W/N \text{(ml/session)} \quad (4A)$$

For example, assuming an infant's weight is 1 Kg (a very low birth weight infant), and N=8 sessions/day, and K=120 Kcal/kg/day, then eq. (5) gives a prescribed volume of:

$$V_{prescribed}=150 \times \tfrac{1}{8} \text{(ml/session)} \quad (5)$$

$$V_{prescribed}=18.75 \text{(ml/session)} \quad (6)$$

Preferably, the nutritional constant, K, is decreased with increased gestational age. Typically, feeding formulas with a high nutritional calorie content (calorie density) of 24 Kcal/oz are used for very low birth weight premature infants. Then, as the infant matures and gains weight appropriately, lower caloric content formula can be used; i.e., transitioning to 22 kcal/oz, and then to 20 kcal/oz formulas when the baby is discharged from the hospital. Note: one can reduce total calories by either using a less caloric-rich formula, or by decreasing the total volume of the original formula offered. However, proper hydration is essential; so the need for hydration must be evaluated at the same time. These changes are factored into FIG. 5, which shows a chart of the nutritional constant, K, in Kcal/Kg/day versus gestational age in weeks.

For late pre-term infants, K=110 Kcal/Kg/day, and equation 4A is modified as follows:

$$V_{prescribed}=137.5 \times W/N \text{(ml/session)} \quad (4B)$$

For full-term infants, K=100 Kcal/Kg/day, and equation 4A is modified as follows:

$$V_{prescribed}=125 \times W/N \text{(ml/session)} \quad (4C)$$

Figure 6:
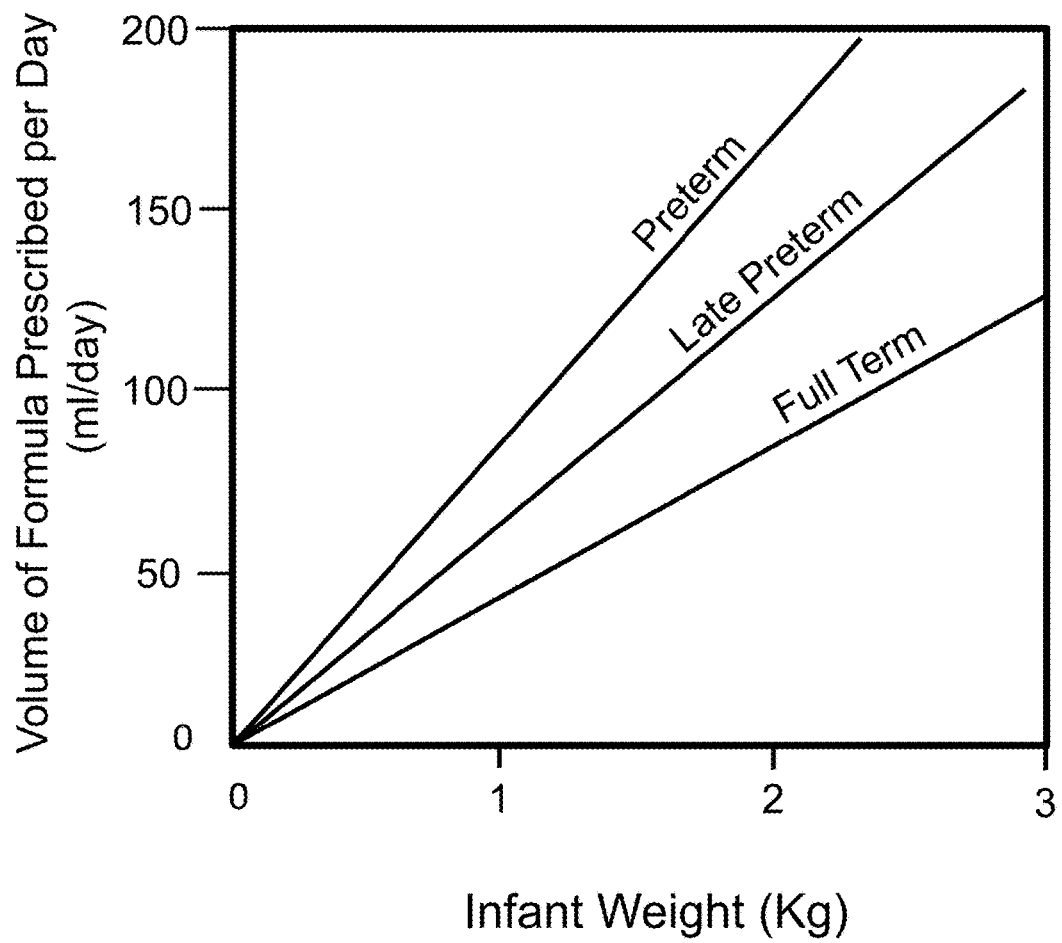
FIG. 6 shows a plot of typical prescribed volumes (ml) as a function of infant weight (Kg), for three different sets of infants: preterm, late preterm, and full term; corresponding to caloric contents of 24 Kcal/oz, 22 Kcal/oz, and 20 Kcal/oz, respectively.

FIG. 6 shows a plot of typical prescribed volumes (ml) per day as a function of infant weight (Kg), for three different sets of infants: Preterm, Late Preterm, and Full Term; corresponding to nutritional caloric contents equal to 24 Kcal/oz, 22 Kcal/oz, and 20 Kcal/oz, respectively. The daily volume prescribed, $V_{prescribed}$, increases linearly with weight (within a selected age group). In clinical practice, regardless of how premature the infants were at birth, when they gain around 3 Kg, and close to discharge, they are transitioned to a 22 Kcal/oz formula, and then to a 20 Kcal/oz formula, especially at the time when they are discharged home. One wants to get back to a 20 Kcal/oz formula when infants are home and feeding ad libitum, i.e., no more than prescribed volume (infants generally eat until they have had enough). Table 1A shows the prescribed volume, $V_{prescribed}$, as a function of Formula Strength (Kcal/oz) and nutritional constant, K (Kcal/kg/day).

TABLE 1A

Prescribed Volume, $V_{prescribed}$, per Kg per day

| Nutritional Constant, K | Formula Strength | | |
|---|---|---|---|
| | 20 Kcal/oz (30 ml) | 22 Kcal/oz (30 ml) | 24 Kcal/oz (30 ml) |
| 120 Kcal/kg/day | 180 ml/kg/day | 164 ml/kg/day | 150 ml/kg/day |
| 110 Kcal/kg/day | 165 ml/kg/day | 150 ml/kg/day | 137 ml/kg/day |
| 100 Kcal/kg/day | 150 ml/kg/day | 136 ml/kg/day | 125 ml/kg/day |

Depending on the gestational age of the premature infant, the OFS cutoff level for proficiency ($PRO_5$) may vary from 25% for very low birth weight infants to 40% for near pre-term infants. In contrast, the OFS cutoff level for rate of transfer, $RT_{20}$, stays relatively constant at 1.5 ml/min for premature infants, independent of the infant's gestational age. For full-term babies, the OFS cutoff level for proficiency ($PRO_5$) may be as high as 50%; and the cutoff for overall flow rate averaged over a feeding session, $RT_{20}$, may be significantly higher, e.g., in the range of 5-10 ml/min.

FIG. 7 plots the proficiency cutoff value, $PRO_5$, as a function of gestational age. Here, the proficiency cutoff, $PRO_5$, increases with increasing gestational age insofar as in-utero maturation increases the longer the gestational period, with $PRO_5$ doubling in value from 25% to 50% for a GA of 25 weeks to 40 weeks. In particular, $PRO_5$=30% for GA in the range of 25-33 weeks; $PRO_5$=40% for GA in the range of 34-36 weeks; $PRO_5$=50% for GA in the range of 33-42 weeks.

FIG. 8 plots the transfer rate cutoff value, $RT_{20}$ (ml/min) as a function of gestational age in weeks. The $RT_{20}$ cutoff value increases with increasing gestational age. In particular, $RT_{20}$=1.5 for GA in the range of 25-33 weeks; $RT_{20}$=1.5 for GA in the range of 34-36 weeks; $RT_{20}$=3.0 for GA in the range of 33-42 weeks.

FIG. 9 shows an example of the percent distribution (percent occurrence) of oral feeding skill levels by gestational age stratum in infants born between 26 and 36 weeks gestation, at their very first oral feeding experience [23]. It can be seen that the more premature the infants (26-29 weeks gestation at birth), the greater the percentile of infants with the most immature oral feeding skills, i.e., OFS level 1. Conversely, the less premature the infants are (34-39 weeks gestation at birth), the greater the percentile of infants with the most mature oral feeding skills, i.e., OFS level 4.

FIG. 10 shows the Overall Transfer (OT, %) of the same group of infants monitored at their very first oral feeding experience, as a function of the respective maturation levels of their oral feeding skills; namely infants with high vs low actual feeding skills (PRO greater/less than 30%) vs. endurance ($RT_{20}$ greater/less than 1.5 ml/min) for very low birth weight (VLBW) infants born between 26 and 36 weeks gestation [23]. Overall Transfer (OT, %) is defined as the ratio of total fluid taken at the end of a feeding session divided by the total volume of liquid prescribed, usually expressed as a percentage. As expected, a low OFS level 1 (poor skills, poor endurance) corresponds to a low Overall Transfer (OT) ratio, averaging around 30%±24% (SD). And, as expected, a high OFS level 4 (good skills, good endurance) corresponds to a high overall transfer ratio, averaging around 96%±12% (SD). What is somewhat surprising is that the intermediate OFS levels 2 and 3 also correspond to a high overall transfer rate, with OFS level 2 averaging 85%±17% and OFS 3 averaging 78%±21%. This indicates that either good skills or good endurance (or both) are important for achieving successful feeding performance (defined as OT≥80%). In summary, according to FIG. 10, the OT value is useful for distinguishing between OFS level 1 and OFS levels 2, 3, and 4, but not particularly useful for distinguishing between OFS levels 2, 3, and 4.

FIG. 11 shows a first example of a high-level methodology for using the smart baby bottle with a smart device and embedded application ("APP"). In step 100, the feeding protocol is defined by the caregiver and smart device application, based on the infant's weight (Step 60) and gestational age (Step 50), for a range of nutritional requirements. In step 70, the volume prescribed ($V_{prescribed}$) is calculated, based on the needed nutritional constant, K, and infant's weight, W. Next, in step 200, the instantaneous feeding performance (e.g., Proficiency, PRO(t), and flow rate, FR(t), is measured over time while feeding by the OMK instrumentation module in the smart (instrumented) bottle. Optionally, the overall rate of transfer, OT, can be measured in step 200. Next, in step 300, the OFS skill levels (1, 2, 3, 4) are determined by using the algorithm(s) built into the smart device's application (APP) (see, e.g., Tables 2, 3, or 4). Then, in step 400, if OFS<3, then maintain the feeding protocol for about 2 days. Next, in step 500, if OFS remains <3, then implement Feeding Interventions for another 2 days. Next, in step 600, if OFS remains <3, then change interventions for another 2 days. Next, in step 700, if there is no change, then consult Pediatric Subspecialties (e.g., Gastroenterology (GI), Ear-Nose-Throat (ENT), etc.). If OFS=4 at any point in time, then the performance is "successful". After feeding is completed, the final level of OFS (1, 2, 3, or 4) is displayed or announced by the smart device, and the application suggests a variety of possible interventions (recommendations) for improving feeding performance if OFS=1, 2, or 3. If OFS=1 (poor skills, poor endurance) at any point in the feeding, then the smart device alerts the caregiver to STOP feeding the infant by displaying or announcing "Stop Feeding" (step 500). If OFS=4, the feeding performance is displayed as "successful", and no interventions are suggested. The performance data are saved by the smart device for future retrospective analyses and longitudinal study.

FIG. 12 shows a second example of an algorithm for determining OFS levels. FIG. 12 follows the simplified algorithm defined in Table 1. Note: the parameter PRO(5) is defined as the % volume (ml) taken during the first 5 min divided by the total volume (ml) of liquid prescribed. The parameter RT(20) is defined as the overall (average) rate of milk transfer (ml/min) averaged over an entire 20 minute feeding session. The algorithm starts with inputting the gestational age (GA), weight (W), of the infant, and the number of feeding sessions in a day, N. Then, using the gestational age, the cutoff values of $PRO_5$, and $RT_{20}$, and K (nutritional constant) are determined by looking up the appropriate values in Table 1 or by evaluating a programmed equation. Then, the prescribed volume of fluid to be taken, $V_{prescribed}$, is calculated using the appropriate eq. (4A or 4B or 4C). Then, feeding begins in step 1000. Next, in step 1050 the volume taken (ingested), V(t), is measured after time=5 and 20 minutes either by direct measurement, or by weighing the bottle and calculating the change in weight, then converting the weight change to volume of liquid taken, V(t) via the density (as milk density is equal to 1.011 g/cc). At time=5 minutes, the proficiency parameter, PRO (%) is calculated, using the measured volume of fluid taken after 5 minutes, V(t=5 min), according to eq. (7A):

$$PRO(5)=V(t=5 \text{ min})/V_{prescribed} \times 100 (\%) \quad (7A)$$

Then, in step 1100 the average flow rate, RT(20), (ml/min) at 20 minutes is calculated or measured according to eq. (7B):

$$RT(20)=V(t=20)/20 (\text{ml/min}) \quad (7A)$$

Next, in step 1200, the measured PRO(5) value is compared to the $PRO_5$ cutoff (i.e., $PRO_5$=30% for VLBW infants or 40% for late preterm and term infants, respectively). Then, in step 1300 and 1600, the measured Flow Rate, RT(20), is compared to the cutoff value of $RT_{20}$=1.5 ml/min. Depending on the results of the comparisons in steps 1400, 1500, 1700 and 1800, the intermediate OFS level is determined according to Table 2, 3, or 4 below (depending on the gestational age), and displayed on a display unit (e.g., smartphone, tablet, or computer monitor), along with the elapsed time since start of feeding. If the OFS level is equal to 1, then the baby is having significant difficulty feeding and feeding should STOP and be assessed. Note that the Overall Transfer (OT, %), given by eq. (8), is equal to the final value of the calculated proficiency parameter PRO (i.e., at time=20 minutes):

$$OT = PRO(t=20) = V(t=20)/V_{prescribed} \times 100 (\%) \qquad (8)$$

The average rate of transfer, RT(20), is typically less than the initial rate of transfer, RT(0), because of the development of fatigue during feeding.

Once RT(20) is calculated, this can be compared with the cutoff value, $RT_{20}$, for making a final determination of the overall OFS level, depending on the Gestational Age of the infant.

TABLE 1

OFS Algorithm #1 for very low birth weight infants
Overall Performance:

If PRO(5) ≥ 30% → OFS level = 3 or 4;
  If RT(20) ≥ 1.5 ml/min → OFS 4;
  If RT(20) < 1.5 ml/min → OFS 3;
If PRO(5) < 30% → OFS level = 1 or 2;
  If RT(20) ≥ 1.5 ml/min → OFS 2;
  If RT(20) < 1.5 ml/min → OFS 1 → STOP feeding.

Depending on the results of the comparisons, the OFS level is finally determined according to the logic listed in Table 2, 3, or 4, and displayed on a display unit (e.g., smartphone, tablet, or computer monitor). Note: PRO(5)=proficiency at t=5 min, and RT(20)=average rate of transfer after t=20 min. For infants that are pre-term, then Table 2 should be used.

TABLE 2

Determination of OFS Level for GA = 25-33 weeks

If PRO(5) ≥ 30% and RT(20) ≥ 1.5 ml/min, then OFS = 4;
If PRO(5) ≥ 30% and RT(20) < 1.5 ml/min, then OFS = 3;
If PRO(5) < 30% and RT(20) ≥ 1.5 ml/min, then OFS = 2;
If PRO(5) < 30% and RT(20) < 1.5 ml/min, then OFS = 1.

For infants that are late pre-term, Table 3 should be used.

TABLE 3

Determination of OFS Level for GA = 34-36 weeks

If PRO(5) ≥ 40% and RT(20) ≥ 1.5 ml/min, then OFS = 4;
If PRO(5) ≥ 40% and RT(20) < 1.5 ml/min, then OFS = 3;
If PRO(5) < 40% and RT(20) ≥ 1.5 ml/min, then OFS = 2;
If PRO(5) < 40% and RT(20) < 1.5 ml/min, then OFS = 1.

For infants that are term, Table 4 should be used.

TABLE 4

Determination of OFS Level for GA = 37-42 weeks

If PRO(5) ≥ 50% and RT(20) ≥ 3 ml/min, then OFS = 4;
If PRO(5) ≥ 50% and RT(20) < 3 ml/min, then OFS = 3;
If PRO(5) < 50% and RT(20) ≥ 3 ml/min, then OFS = 2;
If PRO(5) < 50% and RT(20) < 3 ml/min, then OFS = 1.

FIG. 13 shows a flow chart of a third example of an algorithm for sorting feeding performance into the four OFS levels 1, 2, 3, 4. This algorithm is based on measuring the flow rate at 5 minute intervals (e.g., based on weighing the bottle every 5 minutes). The cutoff ranges of Flow Rate, FR, (e.g., 0-4, and 5-9, and ≥10 ml/min), are appropriate for pre-term and late pre-term infants. OFS levels 2 and 3 are grouped together into the "Yellow" group, since their overall volumetric transfer (OT, %) are roughly the same in both groups (80-90%).

FIG. 14 shows Table 5 with 9 different scenarios (possible histories), based on the flow chart of FIG. 13. The following parameters are defined in Table 6:

TABLE 6

Parameter Definitions

FR(5) = FR(0-5) = average flow rate from 0-5 minutes;
FR(10) = FR(6-10) = average flow rate from 6-10 minutes;
FR(15) = FR(11-15) = average flow rate from 11-15 minutes;
FR(20) = FR(16-20) = average flow rate from 16-20 minutes.

Referring still to FIG. 14, the following visual scale is defined as being associated with a particular flow rate and OFS level (Table 7):

TABLE 7

Visual Symbol Associations

Green = G = "good" = flow rate ≥ 10 ml/min = OFS level 4;
Yellow = Y = "be watchful" = flow rate = 5-9 ml/min = OFS level 2 or 3;
Red = R = "stop" = flow rate = 0-4 ml/min = OFS level 1;
Stop = S.

The OT range, Comments, and Recommendations listed in FIG. 14 are based on our studies [23,31].

At each measurement point in time (e.g., 5, 10, 15, or 20 minutes), the volume of fluid taken (ingested) is measured (e.g., by weighing the bottle, or by using an instrumented flow monitoring system), and a calculation of the average flow rate during the preceding 5 minutes is performed. This value is sorted into one of three possible bins: (≥10 ml/min, 5-9 ml/min, or 0-4 ml/min), and a color is assigned (green, yellow, red), which can be displayed to the caregiver on a display unit on the bottle or on a remote device. At the same time, an optional audible alert can be given by the display unit, using the following scale (Table 8):

TABLE 8

Audio Associations (soft sounds)

Green = good = OFS 4 = one "bip";
Yellow = be watchful = OFS 2 or 3 = two bips: "bip-bip";
Red = stop = OFS 1 = three bips: "bip-bip-bip".

Alternatively, a visual scale can be displayed on a display unit that shows vertical bars (similar to multiple bars for signal strength of a wireless phone or wireless network), according to the following scale (Table 9):

TABLE 9

Visual Bar Associations

Green = good = OFS 4 = three vertical bars;
Yellow = be watchful = OFS 2 or 3 = two vertical bars;
Red = stop = OFS 1 = one vertical bars.

Alternatively, an opposite type of visual scale can be displayed, which correlates the number of vertical bars to the OFS scale, according to Table 10:

TABLE 10

Alternative Option for Visual Bar Display Associations

OFS level 4 = 4 vertical bars;
OFS level 3 = 3 vertical bars;
OFS level 2 = 2 vertical bars;
OFS level 1 = 1 vertical bar.

Alternatively, a computer synthesized set of audio instructions (statements) can be "spoken" by the monitor, smartphone, tablet, or computer, according to Table 11:

TABLE 11

Audio Statements (soft sounds)

Green = good = OFS 4 = "Baby is feeding well";
Yellow = be watchful = OFS 2 or 3 = "Baby is started to tire";
Red = stop = OFS 1 = "Baby needs to stop feeding".

Optionally, the user can turn off the audio announcements and/or audio statements, in order to have a quiet environment.

FIG. 15 shows an example of a fourth algorithm for determining OFS levels. FIG. 15 follows the simplified algorithm in Table 12.

TABLE 12

OFS Algorithm #3
Overall Performance:

If PRO(t) ≥ 6 · t (%) → OFS level = 3 or 4;
If RT(20) ≥ 1.5 ml/min → OFS 4;
If RT(20) < 1.5 ml/min → OFS 3;
If PRO(t) < 6 · t (%) → OFS level = 1 or 2;
If RT(20) ≥ 1.5 ml/min → OFS 2;
If RT(20) < 1.5 ml/min → OFS 1 → stop feeding; and
If PRO(t) < 2 · t (%) → OFS 1 → stop feeding;

In this scheme, Table 12, the first cutoff for OFS determination is based on a constant rate of volumetric transfer equal to 6% per minute (which equates to 30% after 5 minutes of feeding). Using the instantaneous volumetric rate of fluid transfer (i.e., %/min) allows for a more generalized assessment to be performed at any time, t, (e.g., every 1 minute), rather than doing it only at a fixed time (e.g., at t=5 minutes). This would be useful in conjunction with an instrumented smart bottle, for example. Assuming the infant transfers fluid at a constant rate of about 6%/minute initially without any fatigue, this means that they can transfer 100% of the prescribed volume in about 17 minutes. Strong feeders transfer fluid at a much faster volumetric rate, e.g. at 12%/min; which means that they can transfer 100% of the prescribed volume in about 8 minutes without fatigue.

In this scheme shown in FIG. 15, the parameter V(t) is the volume taken (ingested) by the infant as a function of time, t. The parameter PRO(t) is defined as the volumetric proficiency (as a function of time, t), which is equal to the ratio of volume taken (from beginning to time=t) divided by the prescribed volume (from Eq. 4A, 4B, or 4C), as follows:

$$PRO(t) = V_{taken}(t)/V_{prescribed} \times 100 (\%) \quad (9)$$

Here, we note that at t=5 minutes, the proficiency is equal to PRO(5):

$$PRO(t=5) = PRO(5) \quad (10)$$

In a similar fashion, the average rate of transfer, RT(t) can be defined as the secant average feeding rate (flow rate) averaged over the period of time, t, (i.e., from 0 to t minutes), and is given by equation (12) as follows:

$$RT(t) = V(t)/t = PRO(t) \times V_{prescribed}/t \, (\text{ml/min}) \quad (11)$$

Note that by using eq. 9, eq. (11) can be rewritten as:

$$RT(t) = PRO(t) \times V_{prescribed}/t \, (\text{ml/min}) \quad (12)$$

Note that the value at t=20 minutes, RT(20), is equal to the average overall transfer rate value, as follows:

$$RT(t=20) = PRO(20) \times V_{prescribed}/20 \quad (13)$$

In summary, the use of OFS levels can offer a more objective, real time indicator of infants' ability to feed by mouth than Gestational Age (GA) or other tools currently available. It does not claim to provide the ultimate answer for solving infants' oral feeding difficulties, as the latter are multi-factorial. However, it does offer the ability to differentiate between feeding aptitude and endurance/fatigue, which are both equally important for oral feeding success.

The use of an OFS scale coupled with an assessment algorithm offers several features. (1) It is easy to measure, as caregivers need only collect the volume reading at, for example, 5 minutes into the feeding session (in addition to the routine information routinely collected, i.e., volume prescribed, volume taken, and feeding duration). (2) No special equipment is required. (3) It provides an objective rather than subjective assessment of infants' feeding skills during a feeding session. (4) As infants of similar GA differ in OFS, evaluating their levels prior to the introduction of oral feeding can help identify infants' ability when oral feeding is initiated. (5) Measuring OFS levels does not only pertain to infants' first oral feeding. Monitoring OFS longitudinally (i.e., over a period of weeks) as infants wean from tube feeding provides information on their maturation process. (6) It can be used as an indicator of whether oral feeding should be advanced or held back. (7) Additionally, if an infant is receiving a particular intervention, monitoring over time can help determine the intervention's efficacy.

OFS levels may also assist caregivers to identify whether infants' oral feeding issues relate to skill levels or to endurance (or both). For instance, if an infant exhibits an OFS level of 1, with low skill and endurance, he/she may benefit from both oral feeding therapy and 'endurance training' (see below, and FIG. 14). An OFS level 2 infant with low skill and high endurance would likely only require oral feeding therapy; whereas an OFS level 3 infant with high skill and low endurance would benefit primarily from 'endurance training'. An infant at OFS level 4 would need no intervention.

An important purpose, therefore, of monitoring an infant's feeding performance and then sorting the infant's performance into one of four oral feeding skill (OFS) levels, is to provide useful feedback information to the caregiver to allow him/her to implement pertinent interventions aimed at improving the feeding performance. Overall, if an infant's Overall Transfer rate (OT, ml/min) is ≥80%, then the feeding is generally considered "successful" and 1-2 days are allowed for maturation to occur. However, if OT<80%, intervention should be considered. Table 10 lists potential interventions that can be considered, based on the specific OFS level:

TABLE 10

Suggested Interventions to Consider

| OFS Levels | Feeding skills (PRO) | Endurance (RT) | Potential interventions |
|---|---|---|---|
| 1 | Poor | Poor | Appropriate evidence-based directed intervention(s) + "oral endurance feeding training" |
| 2 | Poor | Good | Appropriate evidence-based directed intervention(s) |
| 3 | Good | Poor | "oral endurance feeding training" |
| 4 | Good | Good | none |

In order to prevent negative oral feeding experiences and/or excessive fatigue [22], an endurance training program may be implemented. This may consist of daily, shortened feeding sessions, the total duration of which equals the duration corresponding to the number of oral feedings per day ordered (prescribed). For instance, if an infant is allowed to feed once a day for a maximum of 20 min, but at the first feeding on that day, he/she exhibits signs of fatigue, disorganization, and/or unstable behavioral state after 5 min, the 'endurance training' may consist of four, 5-min feedings on that particular day (for the same total of 20 min.). Feeding duration can be gradually increased on a daily basis as the above symptoms decrease. This type of training is based on the general acceptance that 'practice makes perfect', in the absence of adverse events or chronic conditions.

For OFS level 2, another example of an evidence-based feeding intervention can comprise performing non-nutritive oral motor therapy (NNOMT). The NNOMT protocol [Fucile, 19] comprises stroking the cheeks, lips, gums and tongue for 12 minutes, concluding with a 3-minute active sucking on a pacifier. Other time intervals can be used, as well. See also references [20] and [21].

Figure 21C:
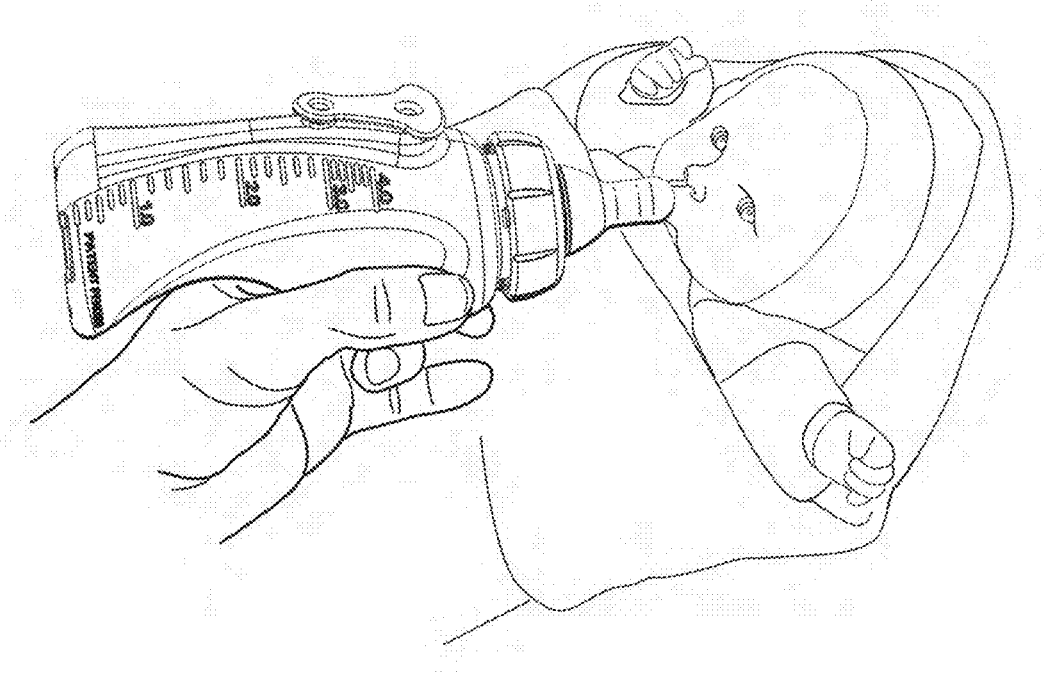

Another example of an evidence-based feeding intervention can additionally (or optionally) comprise using a self-paced feeding bottle [24]. This type of bottle design has a vent hole for preventing the undesirable buildup of internal vacuum as the fluid empties from the bottle. Also, the self-paced bottle has a unique liquid-feeding setup that prevents the development of positive hydrostatic pressure, which builds up when the bottle is tilted at too great an angle to the horizontal, leading to a continual dripping of milk into the infant's mouth. If the infant is not ready to feed, such dripping may lead to adverse events such as choking, fluid aspiration into the lungs. It was shown in [24] that very low birth weight infants significantly improved their OFS levels, from mostly OFS 1 to mostly OFS 4, when a self-paced feeding bottle was substituted for a standard (non-vented) feeding bottle. FIGS. 21A, 21B, and 21C shows different views of an example of a self-paced, ergonomic feeding bottle, according to the present invention.

Another example of an evidence-based feeding intervention can comprise performing non-nutritive sucking exercises using pacifiers. This can be achieved by gently moving the pacifier in a rhythmic up/down posterior/anterior motion that stimulates the infants' non-nutritive sucking. However, research has shown that this particular intervention is not especially effective.

Another example of an evidence-based feeding intervention can comprise performing swallowing exercises. This can comprise placing a bolus of 0.05-0.2 mL of the type of milk the infant was receiving at the time (that is, mother's milk or formula) via a 1-mL syringe directly on the medial-posterior part of the tongue approximately at the level of the hard and soft palate junction (close to the site where the bolus rests prior to entering the pharynx). The infants are started with 0.05 mL, and the volume increased in increments of 0.05 mL to a maximum of 0.2 mL, until the swallowing reflex was observed or as tolerated, (i.e., the intervention was halted at any sign of adverse events, e.g., unstable vitals, choking, fatigue, or disorganization). Once the minimal volume necessary to initiate the swallow reflex is visually identified, it is used for the remaining duration of the exercise. The exercise can be provided every 30 seconds over a 15-minute programme, or as tolerated. In general, it was found that the use of these specific swallowing exercises caused more rapid maturation of oral feeding skills than the use of sucking exercises using pacifiers, as evidenced by the improvement in OFS levels from 1 to 4 among the population studied [25].

Another example of an evidence-based feeding intervention can comprise performing infant massage therapy (iMT). This intervention can comprise stroking the head, neck, back, arms and legs for 10 minutes, combined with passive range of motion applied to the limbs for 5 minutes [27]. Optionally, both NNOMT and iMT therapies can be combined. The studies found that infants who received the NNOMT and/or iMT interventions demonstrated a faster rate of OFS maturation than their control counterparts, and with fewer occurrences of the lowest OFS level, level 1 [26, 28]. Another example of an evidence-based feeding intervention can include changing feeding positions from among supine, sidelying, prone, and upright.

Differences between the effectiveness of the different intervention programs can be attributed to the observation that different neuro-physiologic and -motor functions mature at different rates and times. In fact, the efficacy of a particular type of intervention may depend on the particular developmental stage an infant is at when that intervention is offered (as there are evidence that different physiologic functions are more receptive to "change" at specific times).

The aforementioned decision algorithms and methods of data analyses can be performed using the previously-described "smart" baby bottle system.

Table 11 shows the experimental data from Lau & Smith [23], showing the average (mean) values; standard deviation and Coefficient of Variation (COV)=[(SD/mean)*100], for a range of Gestational Ages from 21-36 weeks (n=66 infants), with the study being done at the first oral feeding experience. COV is a measure of the variability relative to the mean of the subjects' respective outcomes

TABLE 11

Experimental Values of OT, PRO, and RT from Lau [23] for a range of Gestational Ages from 21-41 weeks (n = 89 infants), study done at first oral feeding experience.

| OFS level | OT (%)* [% COV]† | $PRO_5$(%) [% COV] | $RT_{20}$ (ml/min) [% COV] |
|---|---|---|---|
| 1 | 30.3 ± 23.6 [78%] | 12.5 ± 7.3 [58%] | 0.6 ± 0.4 [67%] |
| 2 | 84.8 ± 16.5 [20%] | 23.1 ± 3.6 [16%] | 1.9 ± 0.3 [16%] |
| 3 | 77.9 ± 21.1 [27%] | 47.3 ± 20.2 [43%] | 1.0 ± 0.2 [20%] |
| 4 | 96.3 ± 12.3 [13%] | 64.4 ± 22.8 [35%] | 2.6 ± 1.0 [39%] |

*mean ± SD
†[% Coefficient of Variation]

FIG. 22 shows the range of Overall Transfer, OT (%) as a function of OFS level (also shown in Table 11 [23]. Here, endurance is described by an alternative measure, i.e., OT (Overall Transfer, %), where OT is defined by eq. (14) as:

$$OT = \text{total volume taken at 20 minutes}/V_{prescribed} \times 100 \text{ (in \%)} \quad (14)$$

Here, we see from Lau & Smith [23] that OT may range between 0% to 55% for OFS level 1; 68% to 100% for OFS level 2; 68% to 99% for OFS level 3; and 80% to 100% for OFS level 4.

FIG. 23 shows a chart of infant birth weight (Kg) versus Gestational Age (weeks), for a variety of percentiles commonly used in NICUs. Females and Male infants have basically the same set of curves.

Sensor Systems

FIG. 16 shows a schematic perspective view of a smart infant feeding bottle system communicating wirelessly with a smart device (e.g., smart phone, tablet, personal computer, or desktop data processing box). Such a system 10 is also referred to as an Oral Motor Kinetics (OMK) monitoring system 10, where the OMK system comprises an infant feeding bottle 12 and a battery-powered sensor module 14 that can communicate wirelessly with a smart device 16 via a standardized Bluetooth® type of communications protocol. Sensor module 14 is removable, and can be disposed inside of bottle 12, or attached to the outside of the bottle. Sensor module 14 can also be disposed at the bottom of the bottle 12 (not illustrated), which would be useful for weighing the contents of liquid when the bottle is oriented vertically, or for measuring the height of the liquid column above the bottom using an ultrasonic probe or laser optical fiber(s) oriented along the length of the bottle. Additional details of the sensing elements and sensor instrumentation modules are contained in pending U.S. patent application Ser. No. 14/416,039 to C. Lau, "Systems for Monitoring Infant Oral Motor Kinetics During Nutritive and Non-Nutritive Feeding", filed Jan. 20, 2015, which is incorporated herein by reference in its entirety. In this application, systems and methods are disclosed for: (1) using a miniature pressure transducer mounted near the nipple's tip to monitor the intraoral pressure pulse during an individual suck, and (2) using a pair of pressure transducers mounted front-to-back on the sidewall of the nipple to monitor the speed and intensity of an infant's tongue when stripping the nipple (which relates to the expression component of sucking) during an individual suck. A feeding bottle with such a set of pressure transducers is called an "OMK bottle" (Oral Motor Kinetics Monitoring System). Pressure transducers can also be mounted on a pacifier, to make an "OMK Pacifier"; or mounted on a glove, to make an "OMK Glove".

The sensor module 14 can have sensors that measure pressure (mm Hg), and also the fluid flow rate (ml/min) through the nipple, among other parameters (temperature, etc.). The module's means for measuring an instantaneous fluid flow rate ("flow rate sensor") can utilize or comprise any of a wide variety of methods, devices, and structures that measure/respond to a variety of physical properties of a moving fluid (e.g., velocity, and, hence, volumetric or mass flow rate; pressure; density; etc.), including, but not limited to: airflow sensor, pressure differential or pressure drop across a flow discontinuity or restriction (e.g., a Venturi section, calibrated orifice plate), ultrasonic techniques, thermal properties technique (e.g., Resistance Temperature Detectors (RTD) thermistor, hot-wire technique, thermal flow sensor), MEMS micro flow sensor, electrochemical techniques (electrolytes, electrical admittance, "Lab-on-a-Chip"), MEMS Coriolis-effect flowmeter (resonant tube), semiconductor field effect, Particle Image Velocimetry (PIV), ultrasonic flow detectors, and flow-based laser or optical techniques, as described below. The volume of liquid (bolus, in ml) passing through the flow sensor as a function of time can be calculated by integrating over time the instantaneous measured flow rate (ml/s). The time period for integration can equal, for example, the duration of the single suck; or it can be a longer fixed duration (e.g., a 1 minute or 5 minute time period).

A first class of flow rate sensors comprises one or more sensing elements that are integrated with or reside within the nipple itself (bottle nipple or nipple shield). With the use of miniature/micro-sized transducers (e.g., micro-pressure transducers) and MEMS manufacturing techniques, it is possible to fabricate fluid flow sensors that are small enough to fit inside a nipple, or even inserted into the nipple's exit hole. This is particularly useful, because the fluid flow properties (e.g., velocity, density, mass flow rate, volumetric flow rate) are preferably measured right at the point where the fluid leaves the nipple (i.e., at or near the nipple exit hole).

A second class of flow rate sensors comprise one or more sensing elements and associated electronics contained inside a stand-alone flow rate module that is separate from the nipple, and is positioned somewhere in-between the fluid reservoir (i.e., body of feeding bottle) and the nipple (e.g., in the neck region, or attached to the side of the bottle on the outside of the bottle). Preferably, the flow rate module can measure, as a function of time, the instantaneous velocity or volumetric (or mass) flow rate of fluid flowing into (or out of) the interior volume/space of the nipple. Allowing for changes in the internal volume of the nipple when compressed during expression by the tongue, the flow rate module should be able to measure negative fluid velocities (i.e., milk travelling in the opposite/backwards direction). Likewise, any numerical integration algorithm used to calculate the bolus volume per suck should be able to account for some period of time during a suck when the fluid velocity may be negative.

The flow rate module can utilize any of the wide variety (presented earlier) of methods, devices, and structures that are capable of measuring properties of a fluid in motion (and, hence, volumetric or mass flow rate), including, but not limited to: pressure differential/drop across a flow discontinuity/restriction (e.g., a Venturi section, calibrated orifice (AP), ultrasonic, thermal flow technique (e.g., RTD thermistor, hot-wire technique), MEMS micromachines, electrochemical techniques (electrolytes, electrical admittance, Lab-on-a-Chip), MEMS Coriolis-effect flowmeter (resonant tube), semiconductor field effect, Particle Image Velocimetry (PIV), ultrasonic, and flow-based laser/optical techniques.

A stand-alone flow rate module can have a generally cylindrical shape, and comprises at least one flow channel connecting a back end to a front end for transferring fluid from the bottle to the nipple. The stand-alone module can also comprise a flow rate sensing means for measuring the fluid's velocity and/or flow rate inside the at least one flow channel. The flow channel can have a necked-down or compressed (smaller-diameter) region with a higher fluid velocity where pressure drop measurements are made with, e.g., a pair of micro-pressure transducers. The flow rate module can optionally comprise electronic means for wirelessly transmitting the measured and/or transformed data to a remote receiver (e.g., a laptop computer, a smart phone, or tablet).

FIGS. 17A, 18A, 19A illustrate cross-sectional plan exploded views of different examples of integrating a self-contained, stand-alone sensor module 14 into a feeding bottle 12 using various types of elongated neck pieces 16.

FIG. 17A shows a cross-section, exploded view of an embodiment of a flow rate module for an OMK system, according to the present invention. FIG. 17B shows a cross-section view of the assembled components. An elongated crown ring 18 screws onto the neck 13 of the bottle 12, thereby compressing the nipple 17, the flow rate module 14, and an O-ring seal 15, against the flat end 11 of the bottle's neck.

FIG. 18A shows a cross-section, exploded view of another embodiment of a flow rate module for an OMK system. The flow rate module 14 sits inside of transition piece/adaptor 24 that has internal screw threads 20 at the back end, which mates with the bottle's external threads 13. Adaptor piece 24 has external screw threads 22 at the front end, which mates to the nipple 17 (held by the crown ring 18). FIG. 18B shows a cross-section view of the assembled components.

FIG. 19A shows a cross-section, exploded view of another embodiment of a flow rate module for an OMK system. The flow rate module 14 has an integral circular flange 19 at the front end that mates with the nipple 17 (held by the crown ring 18). The flow rate module 14 has a slightly smaller outer diameter than the inner diameter of the bottle's neck 13, which allows the flow rate module to slip inside of the bottle's neck. An O-ring seal 15 is disposed in-between the module's circular flange 19 and the flat end 11 of the bottle's neck 13. FIG. 19-B shows the assembled components, which is a very compact assembly.

Other techniques can be used, in addition to, or in place of, a stand-alone or nipple-integrated flow rate sensor module or instrumentation device. For example, the change in weight of liquid inside the reservoir (bottle) can be measured before and after a single suck, to get the bolus volume per suck. Or, the change in height of the liquid column inside the reservoir (bottle) can be measured, with the difference being proportional to the volume (bolus) of liquid lost during a single suck. The change in weight ($\Delta W$) can be measured by using a sensitive pressure transducer located at the bottom of the bottle to measure small changes in pressure (weight of the fluid above the pressure transducer) when liquid is removed from the bottle during feeding.

Alternatively, the change in internal air pressure (increase in vacuum level) inside of a sealed bottle (i.e., with no anti-vacuum valve) can be measured with a sensitive pressure transducer placed at or near the top of the bottle. The removal of a bolus of liquid during a single suck creates an incremental change in the vacuum air pressure level (via the relationship Pressure×Volume=constant, at constant temperature), which can be measured, in real-time, by a pressure transducer. Once a particular bottle's geometry has been calibrated (and assuming a bottle with a constant cross-section along it's length), then the drop in internal air pressure measured by the pressure transducer, in real-time, will correlate directly to the volume of liquid removed, in real-time, from the nipple.

FIG. 20 shows a schematic cutaway view of an example of a micro-sensor printed circuit board assembly for use inside of an infant feeding bottle (cover removed for clarity). FIG. 20 shows an instrumented nipple 60 comprising a compact, miniaturized, integrated wireless instrumentation module 62 that fits snugly into the base of a standard nipple 17. The wireless module 62 can comprise one or more of the following components: a flow rate sensor 50, pressure transducers 31, 32, 33 and electrical leads to the module, microprocessor 36, battery 42, transmitter 38, antenna 40, and mounting plate 54. The wireless IM 62 can transmit data via, for example, Bluetooth®, to a BioPac® data collection unit 66, an iPad® or iPhone® smart phone/tablet 66, or laptop computer, etc. A flexible metal bellows 48 can be used to permit flexing (bending) of a tube 46 connecting the flow rate sensor 50 with the exit hole 56 at the nipple's tip.

The flow rate sensor 50 can comprise a pair of pressure transducers arranged to measure a pressure drop along the flow channel 44. The pressure transducer can be a pair of laser fiber optic pressure sensors can be, for example, a model No. OPP-M25, manufactured by OpSens, Inc., in Quebec, Canada (www.opsens.com). This model has an outer diameter of the sensing head of 0.25 mm (250 microns), a pressure range of −50 to +300 mm Hg, a precision of +/−2 mm Hg, and a resolution of 0.5 mm Hg. OpSens also makes a larger fiber optic pressure sensor, OPP-M40, with a 0.4 mm (400 microns) OD of the sensing head. The smaller model, OPP-M25, is the smallest MEMS based optical pressure sensor available on the market today, and is used in a wide variety of medical applications, including: cardiovascular, intracranial, intrauterine, intraocular, intervertebral disc, urodynamic, and compartment pressure measurements. An optical sensor is immune to interference from radio frequency (RF) fields, magnetic resonance imaging (MRI) fields, and electromagnetic radiation from electro-surgery tools.

An instrumentation module (i.e., sensor module) can be used with any type of infant feeding bottle. Optionally, such a module can be used with an "Optima" type of feeding bottle, which is described in more detail in pending U.S. patent application Ser. No. 14/549,519 to C. Lau, et. al, "Self-Paced Ergonomic Feeding Bottle", filed Nov. 20, 2014 which is incorporated herein by reference in its entirety.

FIG. 21A shows a cross-sectional view of a "self-paced" ergonomic feeding bottle, according to the patent application mentioned above. Self-paced bottle 12 comprises a open air vent hole 126; a straight spine segment 130 running down along the upper outside of the bottle; a recessed thumb grip section 152; an overall ergonomically-shaped bottom side profile of the bottle which allows the bottle to rest comfortably in an open hand without requiring a rigid grip; and a plurality of visual and tactile, raised anti-drip markers 150 which serve to guide the caregiver in holding the bottle at the appropriate angle with respect to the horizon, depending on the amount of formula remaining in the bottle, which prevents the buildup of hydrostatic pressure during feeding and stops unnecessary dripping.

FIGS. 21B and 21C show isometric views of the same self-paced ergonomic feeding bottle, illustrating how the bottle is well-balanced and how it rests comfortably in an open hand with minimal gripping strength required. The present invention can use this type of feeding bottle.

FIG. 24 shows a chart detailing the components of an Advanced Feeding Device, according to the present invention. The Advanced Feeding Device (AFD) comprises three main components: a baby (infant feeding) bottle, an instrumentation/sensing (monitor) module, and a data management software application. The baby bottle mates to the monitor module. The monitor module (i.e., instrumentation/sensor module) can have the following functions: (1) it captures feeding data; (2) it displays current feeding performance; (3) it provides an alarm when feeding performance drops below a safe threshold; and (4) it stores and transmits feeding data to the software application, which can reside on a remote device, such as an iPad®, iPhone® or desktop computer. The data management software application can have the following functions: (1) it records feeding data history; (2) it displays the history; (3) it provides analysis of progress and trends over time; (4) and it can transmit feeding data to clinical experts and EMR (electronic medical record) systems.

A detailed minute by minute feeding history can be collected, alongside with the heart rate, blood pressure and other vital sign histories. Vital signs make up what is commonly known as the patient's "Chart". Hospitals could add the feeding history to the Chart for the good reason that baby health events frequently tie in to feeding, so that it helps diagnosis. The method is to upload the data in a standard format defined by the hospital system and according to HIPAA rules. Secondly, we could help by sending data to a doctor or therapist from the smart device APP to their system for review. The smart application sees signs of trouble, arranges for a consultation, and sends data.

Air Flow Rate Sensor

In a preferred embodiment, the amount of air flowing into a bottle with an open air vent can be measured (i.e., by a micro-sized differential pressure measurement or thermal-response flow sensor technique) and set equal to the change in liquid volume exiting the bottle through the nipple (assuming that the inflowing air is essentially incompressible, which is reasonable since the temperature and pressure changes are very small inside and outside of the bottle). A similar technique was used by Jain, et. al. [29], which used a large (non-miniaturized) air flow rate detector unit.

Alternatively, the volumetric rate of incoming air flow can be determined by measuring the change in temperature of an electrically resistively-heated strip or thin film of deposited metal or wire suspended in the stream of air (or, by measuring the power required to maintain a constant temperature in such a heated strip or wire of metal). This is called a micro thermal flow rate sensor, and it has an output signal that changes linearly with corresponding changes in the velocity of fluid flowing through/over the thermal flow sensor. Because the metal strip/film is very thin (typically it is manufactured using MEMS-based technology), it has a very fast thermal response rate (e.g., 1-10 ms response time), and can record very fast changes in fluid velocity (air or liquid) over time. This would allow detailed measurement of the flow velocities as a function of time during an single, individual suck by the infant (ml/sec), assuming that the data collection rate is sufficiently fast to catch the transient velocity pulse (e.g., greater than 10 Hz collection rate).

FIG. 25 shows a side cross-section view of an example of an air flow rate sensor disposed inside of an instrumentation module that is mounted to the outside of the bottle, on the bottle's sidewall. FIG. 26 shows a side, cross-section, exploded view of the example shown in FIG. 25. Module 108 comprises a hollow plastic case (rectangular box 110) that encases the air flow sensor unit 138, flow tube 114, and associated electronics, battery, etc. Case 110 is removably attached to the upper side (spine 130) of bottle 12. Module 108 can be attached by any number of well-known ways, including plastic/elastomeric latches, screws, magnets, sliding rails, rotating latches, elastic members, etc. When liquid is drawn out through the nipple by the infant during feeding, module 110 measures the volumetric rate of replacement air flowing into the module through entrance aperture 112, passing through flow tube 114, past flow rate sensor unit 138, and finally exiting out of module 110 through exit aperture 124. The exiting air continues flowing through anti-vacuum valve 128, eventually dumping into the upper, open internal volume 132 of bottle 12, where it exactly replaces the volume of liquid dispensed/taken through the nipple during feeding. The sensor signals generated by flow rate sensor unit 138 are passed on to circuit board 142, which contains a microprocessor unit (MCU) and other associated electronics for converting the sensor's output to a digital data stream, which is then transmitted wirelessly 146 to a remote device, such as a iPad® or other type of remote computer (not shown) for analysis and display. Note that bottle 12 can be used as a regular feeding bottle when instrumentation module 110 is removed. The volume of fluid taken, V(t) can be easily calculated by integrating the measured rate of volumetric flow over a period of time.

FIG. 27 shows a cross-section view of another example of an air flow rate sensor chip disposed inside of an instrumentation module that is mounted to the outside wall of the bottle, on the bottle's upper side. Module 108 comprises a hollow case 110 with an entrance aperture 112 and exit aperture 124, which are fluidically connected to each other by tube 114 disposed within case 110. During feeding, air flows into the entrance aperture 112 of case 110. A coarse, replaceable particle filter 113 is provided in the flowstream near the entrance aperture 112 to screen out large particulates, dust, etc. The coarse filter can have a pore size of about 5-10 microns, for example. Tube 114 can be made of medical grade silicone or polyethylene, for example, and can have an inner diameter of approximately 1/8" (ranging from 1/16" to 1/4"). Tube 114 is held securely to the sidewall of case 110 using a plurality of integrally-molded web support brackets 121, 121', 121" that the tubing snaps into. Module 110 further comprises a pair of hydrophobic, fine disc filters: upstream filter 117 and downstream filter 119, which are held in place with upstream filter housing 116 and downstream filter housing 120, respectively. The pore size of the fine filters is selected to pass air, but stop water or formula from passing through the filter. For example, the pore size can be 2 microns. The fine filters can be made of a hydrophobic material, preferably transparent, so that visual determination of bacterial contamination can be made. Fine filters 117 and 119 prevent liquid (formula or water) from entering the micro-sized air flow passages in air flow rate sensor chip 138.

FIG. 27 further shows a calibrated flow orifice plate (disc) 118 held inside the flow tubing 114 by orifice holder 115. The purpose of orifice plate 118 is to create a defined pressure difference (pressure drop, $\Delta P=P_1-P_2$)) between the upstream location ($P_1$) and the downstream location ($P_2$) on either side of the orifice. The diameter of the hole in the orifice plate 118 can be in the range of 0.010" to 0.020" diameter. Short segments of bypass tubing 134 and 136 fluidically connect pressure taps at upstream and downstream locations ($P_1$, $P_2$) of tube 114 (above and below the orifice plate 118), to the input and outlet ports of airflow rate sensor chip 138, respectively. Airflow rate sensor chip 138 is a micro/MEMS thermal flow sensor comprising a thin-metallic film sensing element 140 (e.g., thin platinum film) that is resistively-heated by electricity. Air flowing across the surface of the sensing element 140 is heated, and the difference in temperature of the stream of air before and after (upstream and downstream of) the heating element 140 is measured, which provides a signal that is directly proportional to the velocity of the air flow, which is also proportional to the pressure drop $\Delta P$ across the inlet/outlet ports of sensor chip 138. Knowing the velocity of air flow, the volumetric flow rate can be easily calculated via the density of air and cross-sectional area of the flow. Alternatively, it is known that the volumetric flow rate for a precision orifice of known diameter is directly proportional to the square root of the pressure drop across the orifice, $\Delta P$. Once the system has been calibrated, the constant of proportionality can be programmed into the data analysis program, and the air flow rate calculated (sccm). Once the air flow rate is known, at any point in time, the equivalent rate of liquid (formula) flowing out of the nipple can be calculated by using the ratio of density between air and liquid (formula). The electrical output of sensor chip 138 is provided to electronics circuit board 142, which contains a microprocessor control unit (MCU), associated electronics, and transmission circuitry for transmitting a wireless data signal 146. Rechargeable batteries 144 provide electric power to the module, and an input/output port is provided to provide for programming/software changes and data input/output.

Not shown in FIG. 27 are optional design features: LED power/system status lights; USB interface port for holding, e.g., a flash drive; or micro-USB programming interface port; ON/OFF switch; and LED data/message display screen; and piezoelectric loudspeaker; charging cord plug. Batteries 144 can be recharged from a charging station using a wireless inductive charging technique and induction coils embedded within the module 110. Module 110 can optionally comprise a tip/tilt MEMS sensor for sensing the angle of tilt of the module, which can be used to turn the unit ON/OFF, depending upon it's orientation. Module 110 can optionally comprise an optical fiber interface port for downloading digital data optically from the module to memory storage located in a charging station, so that data history is automatically downloaded into the charged station when the module is charged.

FIG. 28-30 show isometric views of another example of an air flow rate sensor disposed inside of an instrumentation module that is mounted to the outside of a feeding bottle, mounted on the bottle's sidewall. Module 108 comprises a case 110 with entrance aperture 112; airflow rate sensor chip 138; electronic circuit board 142; air flow chambers 114; and exit aperture 128.

Prototype Sensor Design, Fabrication and Initial Testing

The maximum air flow that the sensor should see should be in the range of 30 sccm. Accuracy of 5% or better is preferred. Due to the desirable requirements that formula contamination not be permitted in any part of the sensor assembly, it is clear that the small sensing channels and elements typically associated with low pressure flows (e.g., in the 30 sccm range) should not be exposed to the formula. This is because they cannot be easily decontaminated, sterilized, or serviced (disassembly/reassembly). The implication is that the volumetric flow rate measurement must be done indirectly without contact with the liquid formula itself. Measurement approaches are thus directed to measuring the amount of air volume that enters the bottle in order to maintain a stable atmospheric pressure equilibrium when the same volume of liquid is removed from the bottle by the infant. The fluid flow exiting from the bottle should be equivalent to the air flow into the bottle (assuming quasi-static conditions), as guaranteed by the ideal gas law, PV=nRT. Instead of measuring the fluid flow directly, we can measure the air that must come into fill the volume of the fluid that has left the bottle.

There are many air flow sensors available in the marketplace. Most are not commercially available in miniature packages suitable for use in the very limited physical space available in the bottle's spine. However, a MEMS-based technology from SensorTechnics, Inc. was identified that was suitable. After some study, it was determined that the "LDE" series of differential pressure sensors could be used with a calibrated bypass orifice as a suitable flow sensor covering range of 0-30 sccm. This sensor has a low power requirement, small size, robust mechanical properties, and an efficient microprocessor interface, along with excellent sensitivity and range. The model "LDES050U 50 Pa" full-scale sensor was chosen for use in the proof-of-principle demonstration prototype. SensorTechnics can produce custom versions (smaller packaging and plumbing connections—possibly integrated with other components as a microfluidic assembly).

Orifice sizing calculations were performed that indicated an orifice size of 0.010" to 0.020" diameter for a 25 Pa drop across the sensor. The prototype actually used a 0.020" diameter orifice with a 50 Pa sensor, with resulting flow resolution of approximately 0.01 sccm and a full scale of about 100 sccm. Precision orifices of several sizes were sourced, with convenient barb fittings, to permit exploration of the parameter space.

In operation, flow rate measurements will be made at about 10 Hz. At each sampling interval the flow rate, along with a timestamp, will be stored in NVRAM (a flash drive has been used to some extent on the proof-of-principle unit). Algorithms specified herein will be on the MCU to look at this data stream in real-time to generate simple feedback signals to the user. It is anticipated that, if available, a GPS location and timestamp can be stored along with the data for each feeding.

Note that the flow rate scaling using pressure drop across an orifice to flow through the orifice requires a square-root operation (note: volumetric air flow rate is proportional to the square root of the pressure drop, $P_1$-$P_2$, across the orifice. This can be expensive in terms of computational resources and power, so it will need to be carefully implemented using either lookup tables or an approximation technique. A strongly suggested method is via CORDIC rotations. In the proof-of-principle/prototype unit this was done using standard floating-point calculations.

A means is required to keep the formula out of the sensor itself when the bottle is not in use (such as when lying in the bottom of a baby bag during a car trip). The fluid must be also kept out of the sensor plumbing during a shock event (accidentally dropping the bottle), inversion, or other unfortunate circumstance. A means should be provided for the user to visually inspect the state of the plumbing and sensor, and if contaminated it should be disposed of and replaced easily.

To accomplish this, several concepts were employed, as shown in the following figures. Several layers of defense against infiltration of the formula into the sensor can be used:

(1) Use the existing silicone slit check valve (anti-vacuum valve 128) to greatly impede the backflow of formula from the bottle back into the instrumentation module 110 (sensor assembly). The cracking pressure (first leakage of fluid through the valve) of the slit valve is about 0.1 inches of $H_2O$, i.e., very low. Commercial micro-checkvalves were found not to come even close to approaching the performance or price of the silicon slit valve, so it was retained. This is convenient, as well because it enables the same bottle to be used with or without the smart feeding module. Some mechanical work will be required to reliably connect the checkvalve to the bottle and the sensor plumbing. Twist-lock mechanisms such as a Luer-Lock are very mature, reliable, and cost effective and should be considered for use in later design work. The initial work was done with an interference fit between silicone tubing and the ID of the checkvalve.

(2) Use an inlet labyrinth consisting of small volumes separated by orifices as means to impede the flow of fluid that has traveled past the slit checkvalve. For the proof-of-principle unit, a small transparent acrylic assembly was designed and fabricated with two internal volumes separated by a 0.035" orifice. The idea is that after filling the first volume, fluid would be restricted by the small orifice and must still fill the second volume before getting further into the sensor. The assembly was easily inspected visually for the presence of contamination. In production, a similar type arrangement could easily be included in a small integrated microfluidic assembly, along with the sensor and other components. The pressure drop across this assembly was found to be insignificant at the flow rates required. However, it was found that over a relatively short time (few tens of minutes) water was able to get through the labyrinth, rendering this approach ineffective.

(3) A hydrophobic pore filter can be interposed between the inlet labyrinth and the flow sensor. If the pore size is below about 0.2 microns, then this filter can also desirably trap bacteria that might flow from into the bottle from the outside air (a sterilizing filter), a useful property. Practically, the filter must not exhibit more than about 0.25 inch $H_2O$ pressure drop at 30 sccm flow. This is a serious issue for small pore size filters, forcing the face area of the filter to be large—easily 5 or more sq. cm. This could be accommodated in the microfluidic assembly, but for the proof-of-principle unit this was done using 25 mm dia Luer-Lock disc filters.

At the very low backpressures encountered in this device, these filters were found to completely block the flow of water. Unfortunately there was also significant pressure drop, in the range of 2 in $H_2O$. Pressure drop data are extremely rare for these devices and is not commonly supplied by the manufacturers. To avoid having to go to very large face area, we should go with larger pore size filters in the next phase, likely 2 microns or so, which are still hydrophobic. We will no longer have sterile air flowing in, but that is not a critical requirement. We will need to re-verify the fluid blocking property at that time.

These filters can be transparent for ease of inspection, and should be easily removable and replaced (disposable) at an economic price if one should be determined to be contaminated. These filters can be had as COTS units in large quantity for about $0.30, with Luer-Lock fittings. With appropriate design (possibly including custom inlet-outlet geometry) such a filter could be an easily replacement part of the bottle spine module, as required.

In summary, it was found that the silicone slit microcheckvalve in conjunction with an appropriately sized poredisc filter(s) can provide adequate protection of the sensor from fluid in the bottle. Optionally, a pair of filter discs can be placed on either side of the flow rate sensor, i.e., both upstream and downstream of the sensor, to protect it from sources of liquid entering the instrumentation module from either direction.

The SensorTechnics LDE series sensors are surprisingly robust to the presence of particulates in the air. The orifice used as a bypass is not, unfortunately, and will require a second filter be placed upstream of the sensor assembly to prevent larger dust, lint, or other particles in the environment from entering the sensor assembly. This filter can be a large pore filter, easily 5 microns or so, and will not present a pressure drop issue even if used in smaller diameter formats (16 mm or so). This coarse filter is not required to have hydrophobic properties. These filters are readily available, but may require custom inlet and outlet fitting geometries for the production unit, unless integrated directly into the microfluidic assembly.

The entire sensor assembly is integrated in the form of a module that attaches (e.g., snaps/latches) to the bottle, effectively forming the upper spine of the bottle. This implies a maximum radial thickness of around 1 cm, a width of around 3 cm, and a length of around 10 cm. Such a package, or closely related constant-volume scalings of it, forms a conveniently sized unit that should present an attractive appearance when attached to the bottle.

Initial considerations indicate that a rectangular 850 maH LiPo battery pack (3 cm×8 cm×0.6 cm) should provide sufficient power for the module. This should leave enough space for a small custom PCB to hold the MCU, interface circuits, sensor circuits, and user indicators, along with the microfluidic assembly containing the sensors, filters, microcheckvalve, and the fittings for connection to the bottle.

This assembly will likely need to be nearly fully encapsulated or potted for mechanical robustness and sealing against the inevitable multiple water submersion events the device will see in a typical household. Potting eliminates the requirement for a housing or an internal frame/bracket assembly. Ergonomic features can be molded into the surface of the final article. For large production, individual potting may be too time-consuming and this issue may need to be revisited.

The spine module is expected to operate for a total duration of approximately 6-8 hours during the course of a day. Given that the unit will be a fully encapsulated module, the battery is required to be of the rechargeable type. The best power density in COTS units today is provided by Lithium-Polymer cells (LiPo). These units require special charging and protection circuits for consumer use, however. Fortunately, there are a number of suppliers of these devices, complete with onboard protection circuitry.

An initial power budget indicated that an 850 maH battery should be sufficient to operate the module for the required 8 hours, subject to reasonable power consumption by the user indicators (Note: extra LEDs, light ring, etc.—have not been addressed at this time).

A special consideration established early on is that the unit should not have any form of electrodes exposed on the surface of the module. These present a reliability and surface contamination issue. Battery charging must be non-contact. We evaluated a simple proximity-inductive charging approach and found that with two coils approximately 3 cm in diameter, we were able to transfer sufficient power to recharge the battery in a few hours at coil separations up to about 8 mm. This provides sufficient design leeway to develop a convenient charging cradle for the module (potentially with a bottle attached).

LiPo batteries also require special charging procedures. Several manufacturers now provide integrated circuits specifically for this task that can easily be designed into the custom spine PCB. Furthermore, we anticipate that we will require a boost converter to bring the LiPo voltage (3.7V) up to 5V to operate the sensors. Devices for this task are also readily available and easily integrated.

A key aspect to maximizing battery life is minimization of standby operating current. To accomplish this task, we anticipate using embedded power control circuits to remove power from all non-essential devices during each phase of operation. This is done using control lines from the MCU to individual FET switches on the power line to the devices (unless the devices have built-in shutdown pins). The MCU itself will have a great deal of built-in power management functionality and will be operated in low power sleep mode when the bottle is not in use. This approach effectively has the battery running at near leakage-current levels when the bottle is idle.

To bring the bottle to life, we can use passive orientation sensors to detect the transition of the bottle from any orientation into the feeding orientation. The feeding orientation is nearly horizontal (to within about +/−15 degrees) with the spine of the bottle on top. We found that this orientation can be easily detected passively using a pair of tilt switches that monitor the axial and azimuthal orientation of the bottle. When this condition is sensed, the MCU will be brought out of sleep mode, immediately initialize the sensors, and being monitoring and recording the flow through the bottle. A timer will also be triggered to turn the bottle off after one hour, or after 15 minutes without any further indication of motion.

This approach allows the bottle to remain in an extremely low power state for long periods of time until the user wants to put it into service, and at that point the transition to operation is completely transparent to the user who is unaware of the process.

Cost is a primary concern in any consumer device. For this unit, we anticipate needing to keep the cost of the sensor and spine board down to a total of less than $50. The most expensive individual part on this unit is the LDE sensor, and the most expensive subassembly is expected to be the integrated microfluidic assembly that carries the micro-checkvalve, inlet hydrophobic filter, sensor, orifice, particulate filter, and connection fittings. With suitable large volumes it is expected that this assembly can be procured for around $27. The electronics and battery will be about another $16. The customer replacement parts (inlet filter, micro-checkvalve, and connection fitting) should be integrated into a single disposable component, which should be producible for less than $1.50 ea.

It is anticipated that the SmartBottle will normally be kept in a wall-mounted cradle for storage and wireless battery charging. The cradle has greatly reduced constraints on power and size and can easily be operated using a wall-mounted low voltage power supply, similar to a wireless telephone. The cradle is expected to incorporate a battery charge state indicator.

The cradle is also expected to serve as a hub for collecting the flow rate histories from the bottle. We anticipate implementing an optical data link between an MCU in the cradle and the spine board MCU. The optical transmitter and receiver on both sides can be coupled via short transparent plastic light guides to an area hidden from view when the bottle is in the cradle. With suitable arrangement of the light guides there should be no issue with alignment of the bottle to the cradle or presence of surface contaminants (easily remove with a damp cloth if it should occur). The encapsulant on the spine module should fully seal the light guides, so there should also be no opportunity for bacterial accumulation in that area.

An initial survey of devices that might serve as a convenient optical data link revealed an IrDA device, Vishay TFBS4711, which can conveniently by driven from the MCU on each side of the data link. We anticipate implementing a simple serial protocol using this device to retrieve and manage flow measurement data, usage statistics, battery life, charge state information, and diagnostic information. These data can be further analyzed by the cradle MCU or could be transmitted via Wi-Fi or other mechanism for further use by the user. This functionality was not investigated in this work as it is a well-developed body of knowledge.

The proof-of-principle unit was assembled using an Arduino Uno equipped with a GPS shield, flash drive shield, LCD shield (for immediate observation of flow measurements), and a custom shield containing the LDE sensor circuitry. Firmware was developed to collect the data and either store it on the flash drive or transmit via USB to the host PC for capture into spreadsheets.

The plumbing was implemented using silicone tubing and barb fittings for the orifice, a Luer-Lock pore-disc filter, the inlet labyrinth assembly, and a graduated dispensing bottle serving as a surrogate for the feeding bottle. A siphon tube was used to establish flow from the dispensing bottle, with the replacement air being pulled through the sensor assembly.

The following photographs (FIGS. 31-33) show the proof-of-principle test assembly used to take the initial experimental measurements.

The following sequence of photos (FIGS. 33-37) shows the use of the siphon to simulate different extraction pressures from the surrogate bottle. Note that since the fluid is water, the pressure in inches of water (in $H_2O$) is simply given by the difference in height (in inches) between the nozzle on the surrogate bottle and the end of the siphon tube (shown attached to an empty dispenser bottle for convenience).

Uniform Flow, Low Flow Rate

The data, shown in FIG. 38-39, were taken to show the measurement of flow when the siphon was set at a constant height, with the surrogate bottle allowed to empty during the run (which changes the height differential). The data were collected at 1 sample per second (1 Hz) using a 0.025" orifice and an LDES050UF6S (50 pa) sensor. The small positive transient is due to the cap being placed on the surrogate bottle. The following large negative transient is the siphon being started. The upward slope on the pressure is due to the water level in the surrogate bottle dropping during the run (as expected). The surrogate bottle was filled to 120 mL as measured using one of the original Optima feeding bottles. The volume is not fully calibrated but is a representative indicator.

High Flow, Varying Rate and Extraction Pressure

For these data, shown in FIGS. 40-41, the flow rate was much higher and was set up to simulate the time varying extraction pressure that might be applied by a feeding infant. The pressure was set to one of four levels by moving the end of siphon to different heights.

Here the steps in the integrated volume are visible as the flow rate changes. The four pressure levels are also clearly visible (there are four quantized levels seen). The integrated volume ceases to increase as the surrogate bottle fully drains (incremental volume goes to zero).

The following chart, in FIG. 42, shows the raw 10 Hz pressure data corresponding to the above charts. These data are filtered in real-time on the Arduino to produce the incremental volume. The transients occur as the siphon hose is quickly moved from one level to another. Note that there is significant fine detail present that may be of interest in clinical work. All of these data is expected to be stored and transmitted to the cradle for further processing in the production units.

In summary, regarding the prototype, the most critical areas of concern regarding design elements for the Optima SmartBottle have been investigated. Sufficient information and data have been collected to indicate that the identified approaches will meet the requirements. There are yet other approaches that were not investigated in this work; they should be considered when doing the initial product design. The most critical issue, that of flow sensing with very limited power and physical space, appears to be handily addressed with the SensorTechnics LDE device.

Alternative Sensor Means

Alternatively, the change in height (ΔH) of the liquid column inside the bottle can be measured by a laser beam liquid level sensing system, or by an ultrasonic liquid level sensing system, along with the appropriate electronics and hardware/software data analysis equipment. To get more accurate measurements of change in height of the liquid column, the system can optionally include: 1) an anti-slosh structure inside the bottle (e.g., a bundle of straws or small diameter tubes, or a porous sponge, which damps unwanted waves/sloshing), and/or 2) a MEMS-based horizontal level detector/indicator mounted to the side of the bottle, for indicating when the bottle is being held vertically (via a buzzing sound, or via LED signal lights, or via a liquid crystal numeric display indicating the bottle's tilt angle in degrees).

Using Integrated Chip (IC) semiconductor technology available today, it is possible to fabricate a compact, miniaturized, integrated wireless instrumentation module (IM) that fits snugly into/inside of the base of a standard nipple, (or attached to the outside of a bottle) which incorporates an integrated microprocessor, A/D converters, flow sensor and pressure transducer electronics, battery, transmitter, and antenna.

LIST OF REFERENCES

[1] American Academy of Pediatrics. Hospital discharge of the high-risk neonate. Pediatrics 2008; 122:1119-1126.

[2] Lau C, Hurst N. Oral feeding in infants. Curr Probl Pediatr 1999; 29:105-24.

[3] Burklow K A, McGrath A M, Kaul A. Management and prevention of feeding problems in young children with prematurity and very low birth weight. Inf Young Children 2002; 14:19-30.

[4] Palmer M M, Crawley K, Blanco I A. Neonatal Oral-Motor Assessment scale: a reliability study. J Perinatol 1993; 13:28-35.

[5] Thoyre S M, Shaker C S, Pridham K F. The early feeding skills assessment for preterm infants. Neonatal Netw 2005; 24:7-16.

(6) da Costa S P, van der Schans C P. The reliability of the Neonatal Oral-Motor Assessment Scale. Acta Paediatr 2008; 97:21-26.

[7] da Costa S P, van dE-H, Bos A F. Sucking and swallowing in infants and diagnostic tools. J Perinatol 2008; 28:247-257.

[8] Als H, Lawhon G, Duffy F H, McAnulty G B, Gibes-Grossman R, Blickman J G. Individualized developmental care for the very low-birth-weight preterm infant. Medical and neurofunctional effects [see comments]. JAMA 1994; 272:853-858.

[9] Rommel N, De Meyer A M, Feenstra L, Veereman-Wauters G. The complexity of feeding problems in 700 infants and young children presenting to a tertiary care institution. J Pediatr Gastroenterol Nutr 2003; 37:75-84.

[10] Premji S S, McNeil D A, Scotland J. Regional neonatal oral feeding protocol: changing the ethos of feeding preterm infants. J Perinat Neonatal Nurs 2004; 18:371-384.

[11] Medoff-Cooper B, Rankin K, Zhuoying L, Liu L, White-Traut R, Multisensory Intervention for Preterm Infants Improves sucking Organization, Advances in Neonatal Care, Vol. 15, No. 2 (2015) pp 142-149.

[12] Lau C, Alagugurusamy R, Schanler R J, Smith E O, Shulman R J. Characterization of the developmental stages of sucking in preterm infants during bottle feeding. Acta Paediatr 2000; 89:846-852.

[13] Poore M, Zimmerman E, Barlow S M, Wang J, Gu F. Patterned orocutaneous therapy improves sucking and oral feeding in preterm infants. Acta Paediatr 2008; 97:920-927.

[14] Gewolb I H, Vice F L. Maturational changes in the rhythms, patterning, and coordination of respiration and swallow during feeding in preterm and term infants. Dev Med Child Neurol 2006; 48:589-594.

[15] Lau C, Smith E O, Schanler R J. Coordination of suck-swallow and swallow respiration in preterm infants. Acta Paediatr 2003; 92:721-727.

[16] Lau C, Sheena H R, Shulman R J, Schanler R J. Oral feeding in low birth weight infants. J Pediatr 1997; 130:561-569.

[17] McCain G C. An evidence-based guideline for introducing oral feeding to healthy preterm infants. Neonatal Netw 2003; 22:45-50.

[18] Scheel C E, Schanler R J, Lau C. Does the choice of bottle nipple affect the oral feeding performance of very-low-birthweight (VLBW) infants? Acta Paediatr 2005; 94:1266-1272.

[19] Fucile S, Gisel E, Lau C. Oral stimulation accelerates the transition from tube to oral feeding in preterm infants. J Pediatr 2002; 141:230-236.

[20] Fucile S, Gisel E G, Lau C. Effect of an oral stimulation program on sucking skill maturation of preterm infants. Dev Med Child Neurol 2005; 47:158-62.

[21] Rocha A D, Moreira M E, Pimenta H P, Ramos J R, Lucena S L. A randomized study of the efficacy of sensory-motor-oral stimulation and non-nutritive sucking in very low birthweight infant. Early Hum Dev 2007; 83:385-388.

[22] Lau C. Oral Feeding in the Preterm Infant. NeoReviews 2006; 7:e19-e27.

[23] Lau C., Smith E O. A Novel Approach to Assess Oral Feeding Skills of Preterm Infants, Neonatology 2011; 100:64-70.

[24] Lau C., et. al. A self-paced oral feeding system that enhances preterm infants' oral feeding skills, J Neonatal Nursing 2014; 08.004.

[25] Lau C., Smith E O. Interventions to improve the oral feeding performance of premature infants, Acta Paediatrica 2012; 101:e269-e274.

[26] Fucile S, Gisel E G, Mcfarland D H, and Lau C, Oral and non-oral sensorimotor interventions enhance oral feeding performance in preterm infants, Dev. Med. Child Neurology, 2011; 53:829-835.

[27] Field T, et al., Tactile/kinesthetic stimulation effects on preterm neonates. Pediatrics 1986; 77:654-658.

[28] Lau C., Fucile S., Gisel E G, Impact of nonnutritive oral motor stimulation and infant massage therapy on oral feeding skills of preterm infants, J Neonatal-Perinatal Medicine 2012; 5:311-317.

[29] Jain, Lucky. et. al, Energetics and mechanics of nutritive sucking in the preterm and term neonate, J of Pediatrics 1987; 111:6, part 1, 894-898.

[30] Rasch S, Sangild P T, Gregersen H, Schmidt M, Omari T, Lau C., The preterm piglet—a model in the study of esophageal development in preterm neonates. Acta Paediatr 2010; 99: 201-208 (doi:10.1111/j.1651-2227.2009.01564.x)

[31] Lau C, Bhat J, Potak D, Schanler R J., Oral Feeding Skills of Late Preterm Infants are correlated with Hospital Length of Stay. J Ped Moth Care 2015; 1:102.

[32] Nyengele G, Zemel J, The Neonur: a Mobile System to Monitor Neonatal Nursing Characteristics, U. Penn, "SUNFEST", July, 2013.

[33] Nyengele G, Zemel J, A Mobile System to Monitor Neonatal Nursing Characteristics, U. Penn, "SUNFEST", July, 2013.

[34] Amaizu N, Shulman R J, Schanler R J, Lau C, Maturation of oral feeding skills in preterm infants, Acta Paediatrica August, 2007, 97, pp. 61-67.

[35] Fusile S, Gisel E, Schanler R J, A controlled-flow vacuum free bottle system enhances preterm infants' nutritive sucking skills, Dysphagia (2009) 24:145-151.

[36] Lau C, Smith E O, Interventions to improve the oral feeding performance of preterm infants, Acta Paediatrica, February, 2012, 101, pp e269-274.

[37] Lau C, Is there an advantage for preterm infants to feed orally in an upright or sidelying position?, Neonatal Nurses Association, April, 2012, pp. 28-32

[38] Lau C, Fucile S, Schanler R J, A self-paced oral feeding system that enhances preterm infants' oral feeding skills, Jnl. Neonatal Nursing, August, 2014, http://dx. doi. org/10.1016/j.jnn.2014.08.004.

[39] Lau C, Smith E O, A novel approach to assess oral feeding skills of preterm infants, Neonatology, January, 2011; 100:64-70.

[40] Kron R E, Ipsen J, Goddard K E, Consistent Individual Differences in the Nutritive Sucking Behavior of the Human Newborn, Psychosomatic Medicine, Vol. XXX, No. 2, 1968, pp. 151-161.

[41] Lau C, Bhat K, Potak D, Schanler R J, Oral feeding assessment predicts length of hospital stay in late preterm infants, J. Ped. Moth. Care, Vol. 1, Issue 1:102, April, 2015, pp. 1-4.

[42] Wicklund E, New sensors help NICU clinicians measure an infant's feeding ability, http://www.nfant.com/#about, Oct. 20, 2015.

[43] Fucile S, McFarland D H, Gisel E G, Lau C, Oral and nonoral sensorimotor interventions facilitate suck-swallow-respiration functions and their coordination in preterm infants, Early Human Development 88 (2012) 345-350.

[44] Lau C, Schanler R J, Oral Motor Function in the Neonate, Neonatal Gastroenterology, Vol. 23, No. 2, June, 1996. pp 161-178.

[45] Waterland A, Berkowitz R I, Stunkard A J, Stallings V A, Calibrated-orifice nipples for measurement of infant nutritive sucking, J. Pediatrics March, 1998; 132:523-526.

[46] Tamilia E, Taffoni F, Formica D, Ricci L, Schena E, Keller F, Guglielmelli E, Technological solutions and main indices for the assessment of newborns' nutritive sucking: A Review, Sensors January, 2014, 14, 634-658; doi:10.3390/s 140100634.

[47] Wang Y L, Hung J S, Wang L Y, Ko M J, Chou W, Kuo H C, Lin B S, Development of a wireless oral-feeding monitoring system for preterm infants, IEEE Jnl. Biomedical and Health Informatics, Vo. 19, No. 3, May, 2015, pp 866-873.

[48] Wang Y H, Lee C Y, Chiang C M, A MEMS-based air flow sensor with a free-standing micro-cantilever structure, Sensors 2007, 7, 2389-2401.

[49] Selley W G, Ellis R E, Flack F C, Brooks W A, Coordination of sucking, swallowing and breathing in the newborn: Its relationship to infant feeding and normal development, British Jnl. of Disorders of Communication, 25, 311-327 (1990).

[50] Goldfield E C, Wolff P H, Schmidt R C, Dynamics of oral-respiratory coordination in full-term and preterm infants: 1. Comparisons at 38-40 weeks postconceptual age, Developmental Science 2:3 (1999), pp 363-373.

[51] Picker R H, Reyna B A, Effects of non-nutritive sucking on nutritive sucking, breathing and behavior during bottle feedings of preterm infants, Advances in Neonatal Care, Vol. 4, No. 4 (August, 2004), pp 226-234.

[52] Lau C, Henning S J, A noninvasive method for determining patterns of milk intake in the breast-fed infant, Jn. of Pediatric Gastroenterology and Nutrition 9:481-487 (1989).

[53] Lau C, Hurst N, Oral Feeding in Infants, Curr Probl Pediatr, April, 1999, pp 105-124.

[54] Lau C, Kusnierczyk I, Quantitative evaluation of infant's nonnutritive and nutritive sucking, Dysphagia 16:58-67 (2001).

[55] Sameroff A J, The Components of Sucking in the Human Newborn, Jnl. of Experimental Child Psychology 6, (1998) pp 607-623.

[56] Tamura Y, Horikawa Y, Yoshida S, Co-ordination of tongue movements and peri-oral muscle activities during nutritive sucking, Developmental Medicine and Child Neurology, 1996 38, pp 503-510.

[57] da Costa S P, Van der Schans C P, The reliability of the neonatal oral-motor assessment sale, Acta Paediatrica, October, 2007, (2008) 97, pp. 21-26.

[58] da Costa S P, Van der Schans C P, The reliability of the neonatal oral-motor assessment sale, Acta Paediatrica, October, 2007, (2008) 97, pp. 21-26, Supplementary Tables.

What is claimed is:

1. A method for assessing a person's oral feeding skills and improving the person's feeding performance, comprising:
   (a) a caregiver providing a person with a feeding container containing a prescribed volume of nutrient liquid, $V_{prescribed}$ (ml);
   (b) measuring a volume of liquid, V(t), dispensed from the container as a function of time, t, during a feeding session;
   (c) determining, using a computer processing unit (CPU), and using the measured volume of liquid taken, V(t), one or more levels of Oral Feeding Skills (OFS) calculated to be 1, 2, 3, or 4, at any point in time during the feeding session, according to the following OFS scale:
      OFS level=1 indicating low oral feeding skills and low endurance;
      OFS level=2 indicating low oral feeding skills and high endurance;
      OFS level=3 indicating high oral feeding skills and low endurance; and
      OFS level=4 indicating high oral feeding skills and high endurance;
   (d) notifying the caregiver to "STOP FEEDING" if OFS=1 at any point during the feeding session;
   (e) notifying the caregiver of "INTERVENTION NEEDED" if OFS=2 or 3 at any point during the feeding session; and
   (f) notifying the caregiver to "CONTINUE FEEDING" if OFS=4 at any point during the feeding session;
   wherein the step (b) of measuring the volume of liquid dispensed from the container as a function of time during the feeding session includes directly measuring a volumetric flow rate of airflow passing through an open air vent hole in a sidewall of the feeding container using a Micro-Electro-Mechanical Systems (MEMS) air flow rate sensor chip; and then setting the average volumetric flow rate of fluid leaving the container during feeding to be equal to the measured average volumetric flow rate of air flowing into the open air vent hole, for a given time interval.

2. The method of claim 1, further comprising communicating data from a sensor means wirelessly from an instrumented container to a remote computing device that comprises computer processing means for processing said sensor data, wherein computer processing comprises: (1) calculating the volume of fluid, V(t), taken by the person as a function of time, and (2) calculating the rate of volumetric flow, FR(t), as a function of time.

3. The method of claim 1, wherein the notifying steps (d)-(f) comprise displaying a message or other visual indication on a display screen placed on the container in direct view of the caregiver who does not lose sight of a feeding person.

4. The method of claim 1, wherein the notifying steps (d)-(f) comprise audibly notifying the caregiver with an audible message or sound containing status information based on the calculated OFS level.

5. The method of claim 1, further comprising:
(g) performing the suggested feeding intervention; thereby improving the person's feeding performance.

6. The method of claim 1, wherein determining the OFS level comprises calculating two parameters: (1) a Proficiency parameter, PRO(5), in percent (%), that is equal to a percentage of volume (ml) taken during the first 5 minutes of feeding divided by a total volume (ml) of liquid that is initially prescribed, $V_{prescribed}$; and (2) a Rate of Transfer parameter, RT(20), that is equal to an overall average rate of liquid transfer (ml/min) averaged over the entire length of the feeding session, which is equal to a total volume of liquid taken, $V_{total}$, over an entire feeding session divided by a length of time of the feeding session.

7. The method of claim 6, further comprising determining the OFS level in step (c) by performing the following logical comparisons at an end of the feeding session:
(a) If PRO(5)≥$PRO_5$ and RT≥$RT_{total}$ ml/min, then OFS=4;
(b) If PRO(5)≥$PRO_5$ and RT<$RT_{total}$ ml/min, then OFS=3;
(c) If PRO(5)<$PRO_5$ and RT≥$RT_{total}$ ml/min, then OFS=2; and
(d) If PRO(5)<$PRO_5$ and RT<$RT_{total}$ ml/min, then OFS=1;
wherein:
$PRO_5$=30% and $RT_{total}$=1.5 ml/min for an infant with a Gestational Age (GA) in the range of 25-33 weeks;
$PRO_5$=40% and $RT_{total}$=1.5 ml/min for an infant with a Gestational Age (GA) in the range of 34-36 weeks; and
$PRO_5$=50% and $RT_{total}$=3.0 ml/min for an infant with a Gestational Age (GA) in the range of 37-42 weeks.

8. The method of claim 7, wherein the feeding duration is equal to 20 minutes; and $RT_{total}$=$RT_{20}$.

9. The method of claim 6, wherein a computer processing unit (CPU) is programmed for calculating the OFS level by performing the following logical comparisons at a specific time=t after start of feeding, wherein time is measured in minutes:
(a) if PRO(t)≥6·t (%), then OFS=3 or 4; wherein
(i) if RT(total)≥1.5 ml/min, then OFS=4, and
(ii) if RT(total)<1.5 ml/min, then OFS=3;
(b) if PRO(t)<6·t (%), then OFS=1 or 2; wherein
(i) if RT(total)≥1.5 ml/min, then OFS=2, and
(ii) if RT(total)<1.5 ml/min, then OFS=1; and
(c) if PRO(t)<2·t (%), then OFS=1.

10. The method of claim 1, further comprising calculating an overall volumetric competency, defined as OT (Overall Transfer, %), which is equal to a total volume of liquid taken by the person during a feeding session, $V_{total}$, divided by the volume initially prescribed, $V_{prescribed}$, with the ratio OT being expressed in terms of a percentage (%).

11. The method of claim 10, wherein a computer processing unit (CPU) is programmed for calculating the OFS level by comparing the OT (Overall Transfer, %) to pre-selected limits according to the following logical comparisons:
(a) OFS=1 when 0≤OT≤13%;
(b) OFS=2 when 13%<OT<60%;
(c) OFS=3 when 60%<OT<90%; and
(d) OFS=4 when 90%<OT≤100%.

12. The method of claim 1, further comprising calculating the prescribed initial volume, $V_{prescribed}$, for a single feeding session, as a function of an infant's weight, W (in Kg) and a number of feeding sessions per day, N, according to Eq (1):

$$V_{prescribed}=C \times W/N \text{(ml/session)} \qquad (1)$$

wherein C=150 ml/Kg for infants born <34 weeks gestation, C=137.5 ml/Kg for infants born between 34 to 36 weeks gestation, and C=124 ml/Kg for infants born between 37 to 42 weeks gestation.

13. The method of claim 1, further comprising calculating an integrated volume of fluid, V(t), taken by the person, as a function of time, by calculating an integral of the following quantity: a measured instantaneous volumetric flow rate, FR(t), (ml/min) times a small time increment (dt) integrated over a period of time from t=0 to t=t, according to Eq. (2):

$$V(t)=\text{INTEGRAL}_{[t=0 \text{ to } t]}\{FR(t) \cdot dt\} \qquad (2).$$

14. The method of claim 1, wherein the nutrient liquid is selected from a group consisting of mothers' milk, infant formula, nutritional drinks, and water.

15. The method of claim 1, wherein a computer processing unit (CPU) is programmed for calculating the OFS level by calculating at every minute an average liquid flow rate, FR(t), based on analyzing measured sensor data, and concurrently performing the following logical comparisons:
(a) if FR(t)=0-4 ml/min, then setting OFS=1;
(b) if FR(t)=5-9 ml/min, then setting OFS=2-3; and
(c) if FR(t)>10 ml/min, then setting OFS=4;
wherein an OFS level=1 is associated with a display color "RED", and a visual or audible indicator provided to the caregiver="STOP FEEDING";
wherein an OFS level=2-3 is associated with a display color "YELLOW", and a visual or audible indicator provided to the caregiver is "BE WATCHFUL";
wherein an OFS level=4 is associated with a display color "GREEN", and a visual or audible indicator provided to the caregiver is "GOOD FEEDING".

16. A method for assessing a person's oral feeding skills and improving the person's feeding performance, comprising:
(a) a caregiver providing a person with a feeding container containing a prescribed volume of nutrient liquid, $V_{prescribed}$ (ml);
(b) measuring with a volumetric sensor means a volume of liquid, V(t), dispensed from the container as a function of time, t, during a feeding session;
(c) determining, using a computer processing unit (CPU), and using the measured volume of liquid taken, V(t), one or more levels of Oral Feeding Skills (OFS)

calculated to be 1, 2, 3, or 4, at any point in time during the feeding session, according to the following OFS scale:

OFS level=1 indicating low oral feeding skills and low endurance;

OFS level=2 indicating low oral feeding skills and high endurance;

OFS level=3 indicating high oral feeding skills and low endurance; and

OFS level=4 indicating high oral feeding skills and high endurance;

(d) notifying the caregiver to "STOP FEEDING" if OFS=1 at any point during the feeding session;

(e) notifying the caregiver of "INTERVENTION NEEDED" if OFS=2 or 3 at any point during the feeding session; and (f) notifying the caregiver to "CONTINUE FEEDING" if OFS=4 at any point during the feeding session;

wherein the volumetric sensor means for measuring the volume of liquid dispensed from the container comprises a stand-alone, battery-powered, wireless instrumentation module removably attached to an outside surface of the feeding container; an inlet in the instrumentation module for admitting air; and an outlet in the instrumentation module that is in fluid communication with an open air vent hole disposed on in the container's sidewall; and a Micro-Electro-Mechanical Systems (MEMS) air flow rate sensor chip for measuring a volumetric flow rate of air passing through the inlet in the instrumentation module during feeding.

17. The method of claim 16, wherein the instrumentation module comprises a one-way, anti-vacuum valve in fluid communication with, and mounted in, the container's air vent hole, whereby any buildup of negative pressure inside the container during feeding is prevented by allowing air to flow into the container through the one-way valve, while also preventing leakage of fluid in the opposite direction out through the one-way valve.

18. The method of claim 16, wherein the feeding container comprises a self-paced, ergometrically-shaped bottle with a one-way, anti-vacuum valve disposed in an air-vent hole disposed on a sidewall of the bottle; and further wherein the bottle or a nipple crown comprises one or more tactile or visual display markers for guiding the caregiver to tilt the bottle at an optimum angle such that a hydrostatic pressure within the bottle is substantially equal to zero during feeding.

19. The method of claim 16, wherein the instrumentation module further comprises a pair of filters capable of filtering viruses or microorganisms present in the surrounding environment from a stream of air flowing into the instrumentation module during the feeding session, with one filter being disposed upstream of the Micro-Electro-Mechanical Systems (MEMS) air flow rate sensor chip, and the other filter being disposed downstream of the Micro-Electro-Mechanical Systems (MEMS) air flow rate sensor chip.

20. The method of claim 16, wherein the instrumented module comprises an outer case; a segment of main airflow tubing connecting the inlet with the outlet; a precision orifice plate disposed inside the main tubing; a pair of filters that filters our harmful particles or microorganisms present in the surrounding environment from a stream of air flowing into the instrumentation module during the feeding session; a pair of pressure taps that bypass a stream of airflow from the main tubing to a pair of inlet/outlet ports on the Micro-Electro-Mechanical Systems (MEMS) airflow rate sensor chip; a dedicated microprocessor for signal conditioning and digital signal generation; associated electronics; a wireless transmitter for transmitting a stream of digital data; a rechargeable battery; and a data input/output port; wherein one filter is disposed upstream of the Micro-Electro-Mechanical Systems (MEMS) air flow rate sensor chip, and the other filter is disposed downstream of the Micro-Electro-Mechanical Systems (MEMS) air flow rate sensor chip; and wherein the method further comprises measuring, with the Micro-Electro-Mechanical Systems (MEMS) air flow rate sensor chip, a change in temperature of an electrically resistively-heated strip or thin film of deposited metal or wire suspended in the incoming stream of airflow; or, by measuring a power required to maintain a constant temperature in such a heated strip or wire of metal.

21. The method of claim 16, wherein steps (b)-(f) are performed by a computer processing unit (CPU) that is contained within the instrumentation module.

22. The method of claim 21, further comprising wireless communication means for wirelessly communicating results data from the CPU to a remote device that comprises a graphical utility application for displaying sensor data and the OFS level.

23. A method for assessing a person's oral feeding skills and improving the person's feeding performance, comprising:

(a) a caregiver providing a person with an instrumented feeding container containing a prescribed volume of liquid, $V_{prescribed}$ (ml); the instrumented container comprising volumetric sensor means for measuring a volume of liquid dispensed from the container;

(b) measuring with the volumetric sensor means a volume of liquid, V(t), passing through an attached nipple over one or more periods of time, t, during a feeding session;

(c) communicating volumetric sensor data wirelessly from the instrumented container to a remote device that comprises a computer processing unit (CPU) for processing said sensor data;

(d) determining, using the CPU, and using the measured volume of liquid taken, one or more levels of Oral Feeding Skills (OFS) calculated to be 1, 2, 3, or 4, according to the following OFS scale:

OFS level=1 indicating low feeding skills and low endurance;

OFS level=2 indicating low feeding skills and high endurance;

OFS level=3 indicating high feeding skills and low endurance; and

OFS level=4 indicating high feeding skills and high endurance;

(e) notifying the caregiver to "STOP FEEDING" if OFS=1 at any point during the feeding session;

(f) notifying the caregiver of "INTERVENTION NEEDED", and making suggested feeding interventions, if OFS=2 or 3 at any point during the feeding session;

(g) notifying the caregiver of "CONTINUE FEEDING" if OFS=4 at any point during the feeding session; and (h) performing the suggested feeding intervention; thereby improving the person's feeding performance;

wherein the volumetric sensor means for measuring the volume of liquid passing through a nipple comprises a stand-alone, battery-powered, wireless, removable instrumentation module removably attached to an outside surface of the feeding container; an inlet in the module for admitting air; and an outlet in the module which is in fluid communication with an open air vent hole disposed in the container's sidewall;

wherein the instrumentation module comprises a Micro-Electro-Mechanical Systems (MEMS) air flow rate sensor chip for measuring a volumetric flow rate of air flowing through the module during the feeding session;

wherein the instrumentation module further comprises a pair of filters that filters out harmful particles or microorganisms present in the environment; and wherein one filter is disposed upstream of the Micro-Electro-Mechanical Systems (MEMS) air flow rate sensor chip, and the other filter is disposed downstream of the Micro-Electro-Mechanical Systems (MEMS) air flow rate sensor chip.

24. The method of claim 23, wherein the remote computing device is selected from the group consisting of a smart phone, smart tablet, laptop, personal computer, and a dedicated desktop data processing device.

25. The method of claim 23, wherein performing the suggested feeding intervention if OFS≤3 comprises performing a technique selected from the group consisting of:

Evidence-Based Feeding Intervention plus Endurance Training if OFS=1;
Evidence-Based Feeding Intervention if OFS=2; and
Endurance Training if OFS=3.

26. The method of claim 25, wherein performing the Evidence-Based Feeding Intervention comprises performing a technique selected from the group consisting of:

Non-Nutritive Oral-Motor Training (NNOMT);
using a Self-Paced feeding bottle with AV-valve and zero-hydrostatic markers;
changing feeding positions from among supine, sidelying, prone, and upright;
doing Endurance Training by increasing the number of oral feedings/day, but shortening these feedings, so that the allowed daily duration of oral feedings remain the same;
doing Non-Nutritive Sucking Exercises;
doing Swallowing Exercises; and
performing Massage Techniques.

\* \* \* \* \*